US009206093B2

(12) United States Patent
Waycuilis

(10) Patent No.: US 9,206,093 B2
(45) Date of Patent: Dec. 8, 2015

(54) PROCESS FOR CONVERTING GASEOUS ALKANES TO LIQUID HYDROCARBONS

(71) Applicant: GTC Technology US, LLC, Houston, TX (US)

(72) Inventor: John J Waycuilis, Cypress, TX (US)

(73) Assignee: GTC Technology US, LLC, Houston, TX (US)

(*) Notice: Subject to any disclaimer, the term of this patent is extended or adjusted under 35 U.S.C. 154(b) by 0 days.

(21) Appl. No.: 14/255,549

(22) Filed: Apr. 17, 2014

(65) Prior Publication Data

US 2014/0228603 A1 Aug. 14, 2014

Related U.S. Application Data

(63) Continuation of application No. 13/679,600, filed on Nov. 16, 2012, now abandoned, and a continuation of application No. 12/957,036, filed on Nov. 30, 2010, now abandoned, and a continuation of application No.

(Continued)

(51) Int. Cl.
*C07C 1/30* (2006.01)
*C07C 1/00* (2006.01)
*C01B 7/09* (2006.01)

(Continued)

(52) U.S. Cl.
CPC . *C07C 1/30* (2013.01); *C01B 7/093* (2013.01); *C01B 7/096* (2013.01); *C01B 9/04* (2013.01); *C07C 1/26* (2013.01); *C07C 1/321* (2013.01); *C07C 17/07* (2013.01); *C07C 17/10* (2013.01); *C07C 17/35* (2013.01); *C10G 29/205* (2013.01); *C10G 29/26* (2013.01); *C10G 50/00* (2013.01); *C10G 50/02* (2013.01); *C07C 2529/40* (2013.01); *C10G 2400/02* (2013.01); *C10G 2400/20* (2013.01)

(58) Field of Classification Search
None
See application file for complete search history.

(56) References Cited

U.S. PATENT DOCUMENTS

| 2,168,260 A | 8/1939 | Heisel et al. |
| 2,246,082 A | 6/1941 | Vaughan et al. |

(Continued)

FOREIGN PATENT DOCUMENTS

| CA | 1099656 | 4/1981 |
| CA | 1101441 | 5/1981 |

(Continued)

OTHER PUBLICATIONS

Indian First Examination Report for Indian Application No. 7955/DELNP/2010 Dated Jul. 21, 2014.

(Continued)

*Primary Examiner* — Tam M Nguyen
(74) *Attorney, Agent, or Firm* — Tumey L.L.P.

(57) ABSTRACT

Embodiments disclose a process for converting gaseous alkanes to higher molecular weight hydrocarbons, olefins or mixtures thereofs wherein a gaseous feed containing alkanes may be reacted with a dry bromine vapor to form alkyl bromides and hydrobromic acid vapor. The mixture of alkyl bromides and hydrobromic acid then may be reacted over a synthetic crystalline alumino-silicate catalyst, such as a ZSM-5 or an X or Y type zeolite, at a temperature of from about 250° C. to about 500° C. so as to form hydrobromic acid vapor and higher molecular weight hydrocarbons, olefins or mixtures thereof. Various methods are disclosed to remove the hydrobromic acid vapor from the higher molecular weight hydrocarbons, olefins or mixtures thereof and to generate bromine from the hydrobromic acid for use in the process.

21 Claims, 15 Drawing Sheets

Related U.S. Application Data

12/123,924, filed on May 20, 2008, now abandoned, and a continuation-in-part of application No. 12/112,926, filed on Apr. 30, 2008, now Pat. No. 8,008,535, and a continuation of application No. 11/254,438, filed on Oct. 19, 2005, now abandoned, and a continuation-in-part of application No. 11/101,886, filed on Apr. 8, 2005, now Pat. No. 7,348,464, and a continuation-in-part of application No. 10/826,885, filed on Apr. 16, 2004, now Pat. No. 7,244,867.

(51) Int. Cl.

| | |
|---|---|
| *C01B 9/04* | (2006.01) |
| *C07C 1/26* | (2006.01) |
| *C07C 17/10* | (2006.01) |
| *C10G 29/20* | (2006.01) |
| *C10G 29/26* | (2006.01) |
| *C10G 50/00* | (2006.01) |
| *C10G 50/02* | (2006.01) |
| *C07C 1/32* | (2006.01) |
| *C07C 17/35* | (2006.01) |
| *C07C 17/07* | (2006.01) |

(56) References Cited

U.S. PATENT DOCUMENTS

| | | |
|---|---|---|
| 2,320,257 A | 5/1943 | Beekhuis |
| 2,488,083 A | 11/1949 | Gorin et al. |
| 2,536,457 A | 1/1951 | Mugdan |
| 2,666,024 A | 1/1954 | Low et al. |
| 2,677,598 A | 5/1954 | Crummett et al. |
| 2,809,930 A | 10/1957 | Miller |
| 2,941,014 A | 6/1960 | Rothweiler et al. |
| 3,076,784 A | 2/1963 | Schulte-Huemann et al. |
| 3,172,915 A | 3/1965 | Borkowski et al. |
| 3,181,934 A | 5/1965 | Davis |
| 3,233,972 A | 2/1966 | Walker et al. |
| 3,240,564 A | 3/1966 | Uffelmann et al. |
| 3,246,043 A | 4/1966 | Rosset et al. |
| 3,254,023 A | 5/1966 | Miale et al. |
| 3,273,964 A | 9/1966 | Rosset |
| 3,291,708 A | 12/1966 | Juda |
| 3,294,846 A | 12/1966 | Livak et al. |
| 3,310,380 A | 3/1967 | Lester |
| 3,314,762 A | 4/1967 | Hahn |
| 3,346,340 A | 10/1967 | Louvar et al. |
| 3,353,916 A | 11/1967 | Lester |
| 3,353,919 A | 11/1967 | Stockman |
| 3,379,506 A | 4/1968 | Massonne et al. |
| 3,468,968 A | 9/1969 | Baker et al. |
| 3,496,242 A | 2/1970 | Berkowitz et al. |
| 3,562,321 A | 2/1971 | Borkowski et al. |
| 3,598,876 A | 8/1971 | Bloch |
| 3,615,265 A | 10/1971 | Gartner |
| 3,642,447 A | 2/1972 | Hahn et al. |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,816,599 A | 6/1974 | Kafes |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,927,111 A | 12/1975 | Robinson |
| 3,928,483 A | 12/1975 | Chang et al. |
| 3,959,450 A | 5/1976 | Calloue et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,819 A | 9/1977 | Schmerling |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Givens et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,604 A | 8/1980 | Kakimi et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,379,734 A | 4/1983 | Franzen |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |

(56) References Cited

U.S. PATENT DOCUMENTS

| | | |
|---|---|---|
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,626,607 A | 12/1986 | Jacquinot et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,725,425 A | 2/1988 | Lesher et al. |
| 4,735,747 A | 4/1988 | Ollivier et al. |
| 4,737,594 A | 4/1988 | Olah |
| 4,748,013 A | 5/1988 | Saito et al. |
| 4,762,596 A | 8/1988 | Huang et al. |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |
| 4,788,377 A | 11/1988 | Chang et al. |
| 4,792,642 A | 12/1988 | Rule et al. |
| 4,795,732 A | 1/1989 | Barri |
| 4,795,737 A | 1/1989 | Rule et al. |
| 4,795,843 A | 1/1989 | Imai et al. |
| 4,795,848 A | 1/1989 | Teller et al. |
| 4,804,797 A | 2/1989 | Minet et al. |
| 4,804,800 A | 2/1989 | Bortinger et al. |
| 4,808,763 A | 2/1989 | Shum |
| 4,814,527 A | 3/1989 | Diesen |
| 4,814,532 A | 3/1989 | Yoshida et al. |
| 4,814,535 A | 3/1989 | Yurchak |
| 4,814,536 A | 3/1989 | Yurchak |
| 4,849,562 A | 7/1989 | Buhs et al. |
| 4,849,573 A | 7/1989 | Kaefing |
| 4,851,602 A | 7/1989 | Harandi et al. |
| 4,851,606 A | 7/1989 | Ragonese et al. |
| 4,886,925 A | 12/1989 | Harandi |
| 4,886,932 A | 12/1989 | Leyshon |
| 4,891,463 A | 1/1990 | Chu |
| 4,895,995 A | 1/1990 | James, Jr. et al. |
| 4,899,000 A | 2/1990 | Stauffer |
| 4,899,001 A | 2/1990 | Kalnes et al. |
| 4,899,002 A | 2/1990 | Harandi et al. |
| 4,902,842 A | 2/1990 | Kalnes et al. |
| 4,925,995 A | 5/1990 | Robschlager |
| 4,929,781 A | 5/1990 | James, Jr. et al. |
| 4,939,310 A | 7/1990 | Wade |
| 4,939,311 A | 7/1990 | Washecheck et al. |
| 4,939,314 A | 7/1990 | Harandi et al. |
| 4,945,175 A | 7/1990 | Hobbs et al. |
| 4,950,811 A | 8/1990 | Doussain et al. |
| 4,950,822 A | 8/1990 | Dileo et al. |
| 4,956,521 A | 9/1990 | Volles |
| 4,962,252 A | 10/1990 | Wade |
| 4,973,776 A | 11/1990 | Allenger et al. |
| 4,973,786 A | 11/1990 | Karra |
| 4,982,024 A | 1/1991 | Lin et al. |
| 4,982,041 A | 1/1991 | Campbell |
| 4,988,660 A | 1/1991 | Campbell |
| 4,990,696 A | 2/1991 | Stauffer |
| 4,990,711 A | 2/1991 | Chen et al. |
| 5,001,293 A | 3/1991 | Nubel et al. |
| 5,004,847 A | 4/1991 | Beaver et al. |
| 5,013,424 A | 5/1991 | James, Jr. et al. |
| 5,013,793 A | 5/1991 | Wang et al. |
| 5,019,652 A | 5/1991 | Taylor et al. |
| 5,026,934 A | 6/1991 | Bains et al. |
| 5,026,937 A | 6/1991 | Bricker |
| 5,026,944 A | 6/1991 | Allenger et al. |
| 5,034,566 A | 7/1991 | Ishino et al. |
| 5,043,502 A | 8/1991 | Martindale et al. |
| 5,055,235 A | 10/1991 | Brackenridge et al. |
| 5,055,625 A | 10/1991 | Neidiffer et al. |
| 5,055,633 A | 10/1991 | Volles |
| 5,055,634 A | 10/1991 | Volles |
| 5,059,744 A | 10/1991 | Harandi et al. |
| 5,068,478 A | 11/1991 | Miller et al. |
| 5,071,449 A | 12/1991 | Sircar |
| 5,071,815 A | 12/1991 | Wallace et al. |
| 5,073,656 A | 12/1991 | Chafin et al. |
| 5,073,657 A | 12/1991 | Warren |
| 5,082,473 A | 1/1992 | Keefer |
| 5,082,816 A | 1/1992 | Teller et al. |
| 5,085,674 A | 2/1992 | Leavitt |
| 5,087,779 A | 2/1992 | Nubel et al. |
| 5,087,786 A | 2/1992 | Nubel et al. |
| 5,087,787 A | 2/1992 | Kimble et al. |
| 5,093,533 A | 3/1992 | Wilson |
| 5,093,542 A | 3/1992 | Gaffney |
| 5,096,469 A | 3/1992 | Keefer |
| 5,097,083 A | 3/1992 | Stauffer |
| 5,099,084 A | 3/1992 | Stauffer |

(56) References Cited

U.S. PATENT DOCUMENTS

| | | |
|---|---|---|
| 5,105,045 A | 4/1992 | Kimble et al. |
| 5,105,046 A | 4/1992 | Washecheck |
| 5,107,032 A | 4/1992 | Erb et al. |
| 5,107,051 A | 4/1992 | Pannell |
| 5,107,061 A | 4/1992 | Ou et al. |
| 5,108,579 A | 4/1992 | Casci |
| 5,118,899 A | 6/1992 | Kimble et al. |
| 5,120,332 A | 6/1992 | Wells |
| 5,132,343 A | 7/1992 | Zwecker et al. |
| 5,138,112 A | 8/1992 | Gosling et al. |
| 5,139,991 A | 8/1992 | Taylor et al. |
| 5,146,027 A | 9/1992 | Gaffney |
| 5,157,189 A | 10/1992 | Karra |
| 5,160,502 A | 11/1992 | Kimble et al. |
| 5,166,452 A | 11/1992 | Gradl et al. |
| 5,175,382 A | 12/1992 | Hebgen et al. |
| 5,178,748 A | 1/1993 | Casci et al. |
| 5,185,479 A | 2/1993 | Stauffer |
| 5,188,725 A | 2/1993 | Harandi |
| 5,191,142 A | 3/1993 | Marshall et al. |
| 5,194,244 A | 3/1993 | Brownscombe et al. |
| 5,202,506 A | 4/1993 | Kirchner et al. |
| 5,202,511 A | 4/1993 | Salinas, III et al. |
| 5,208,402 A | 5/1993 | Wilson |
| 5,210,357 A | 5/1993 | Kolts et al. |
| 5,215,648 A | 6/1993 | Zones et al. |
| 5,223,471 A | 6/1993 | Washecheck |
| 5,228,888 A | 7/1993 | Gmelin et al. |
| 5,233,113 A | 8/1993 | Periana et al. |
| 5,237,115 A | 8/1993 | Makovec et al. |
| 5,243,098 A | 9/1993 | Miller et al. |
| 5,243,114 A | 9/1993 | Johnson et al. |
| 5,245,109 A | 9/1993 | Kaminsky et al. |
| 5,254,772 A | 10/1993 | Dukat et al. |
| 5,254,790 A | 10/1993 | Thomas et al. |
| 5,264,635 A | 11/1993 | Le et al. |
| 5,268,518 A | 12/1993 | West et al. |
| 5,276,226 A | 1/1994 | Horvath et al. |
| 5,276,240 A | 1/1994 | Timmons et al. |
| 5,276,242 A | 1/1994 | Wu |
| 5,284,990 A | 2/1994 | Peterson et al. |
| 5,300,126 A | 4/1994 | Brown et al. |
| 5,306,855 A | 4/1994 | Periana et al. |
| 5,316,995 A | 5/1994 | Kaminsky et al. |
| 5,319,132 A | 6/1994 | Ozawa et al. |
| 5,334,777 A | 8/1994 | Miller et al. |
| 5,345,021 A | 9/1994 | Casci et al. |
| 5,354,916 A | 10/1994 | Horvath et al. |
| 5,354,931 A | 10/1994 | Jan et al. |
| 5,358,645 A | 10/1994 | Hong et al. |
| 5,366,949 A | 11/1994 | Schubert |
| 5,371,313 A | 12/1994 | Ostrowicki |
| 5,382,704 A | 1/1995 | Krespan et al. |
| 5,382,743 A | 1/1995 | Beech, Jr. et al. |
| 5,382,744 A | 1/1995 | Abbott et al. |
| 5,385,650 A | 1/1995 | Howarth et al. |
| 5,385,718 A | 1/1995 | Casci et al. |
| 5,395,981 A | 3/1995 | Marker |
| 5,399,258 A | 3/1995 | Fletcher et al. |
| 5,401,890 A | 3/1995 | Parks |
| 5,401,894 A | 3/1995 | Brasier et al. |
| 5,406,017 A | 4/1995 | Withers, Jr. |
| 5,411,641 A | 5/1995 | Trainham, III et al. |
| 5,414,173 A | 5/1995 | Garces et al. |
| 5,430,210 A | 7/1995 | Grasselli et al. |
| 5,430,214 A | 7/1995 | Smith et al. |
| 5,430,219 A | 7/1995 | Sanfilippo et al. |
| 5,433,828 A | 7/1995 | van Velzen et al. |
| 5,436,378 A | 7/1995 | Masini et al. |
| 5,444,168 A | 8/1995 | Brown |
| 5,446,234 A | 8/1995 | Casci et al. |
| 5,453,557 A | 9/1995 | Harley et al. |
| 5,456,822 A | 10/1995 | Marcilly et al. |
| 5,457,255 A | 10/1995 | Kumata et al. |
| 5,464,799 A | 11/1995 | Casci et al. |
| 5,465,699 A | 11/1995 | Voigt |
| 5,470,377 A | 11/1995 | Whitlock |
| 5,480,629 A | 1/1996 | Thompson et al. |
| 5,486,627 A | 1/1996 | Quarderer, Jr. et al. |
| 5,489,719 A | 2/1996 | Le et al. |
| 5,489,727 A | 2/1996 | Randolph et al. |
| 5,500,297 A | 3/1996 | Thompson et al. |
| 5,510,525 A | 4/1996 | Sen et al. |
| 5,523,503 A | 6/1996 | Funk et al. |
| 5,525,230 A | 6/1996 | Wrigley et al. |
| 5,538,540 A | 7/1996 | Whitlock |
| 5,563,313 A | 10/1996 | Chung et al. |
| 5,565,092 A | 10/1996 | Pannell et al. |
| 5,565,616 A | 10/1996 | Li et al. |
| 5,571,762 A | 11/1996 | Clerici et al. |
| 5,571,885 A | 11/1996 | Chung et al. |
| 5,599,381 A | 2/1997 | Whitlock |
| 5,600,043 A | 2/1997 | Johnston et al. |
| 5,600,045 A | 2/1997 | Van Der Aalst et al. |
| 5,609,654 A | 3/1997 | Le et al. |
| 5,633,419 A | 5/1997 | Spencer et al. |
| 5,639,930 A | 6/1997 | Penick |
| 5,653,956 A | 8/1997 | Zones |
| 5,656,149 A | 8/1997 | Zones et al. |
| 5,661,097 A | 8/1997 | Spencer et al. |
| 5,663,465 A | 9/1997 | Clegg et al. |
| 5,663,474 A | 9/1997 | Pham et al. |
| 5,674,464 A | 10/1997 | Van Velzen et al. |
| 5,675,046 A | 10/1997 | Ohno et al. |
| 5,675,052 A | 10/1997 | Menon et al. |
| 5,679,134 A | 10/1997 | Brugerolle et al. |
| 5,679,879 A | 10/1997 | Mercier et al. |
| 5,684,213 A | 11/1997 | Nemphos et al. |
| 5,693,191 A | 12/1997 | Pividal et al. |
| 5,695,890 A | 12/1997 | Thompson et al. |
| 5,698,747 A | 12/1997 | Godwin et al. |
| 5,705,712 A | 1/1998 | Frey et al. |
| 5,705,728 A | 1/1998 | Viswanathan et al. |
| 5,705,729 A | 1/1998 | Huang |
| 5,708,246 A | 1/1998 | Camaioni et al. |
| 5,720,858 A | 2/1998 | Noceti et al. |
| 5,728,897 A | 3/1998 | Buysch et al. |
| 5,728,905 A | 3/1998 | Clegg et al. |
| 5,734,073 A | 3/1998 | Chambers et al. |
| 5,741,949 A | 4/1998 | Mack |
| 5,744,669 A | 4/1998 | Kalnes et al. |
| 5,750,801 A | 5/1998 | Buysch et al. |
| 5,770,175 A | 6/1998 | Zones |
| 5,776,871 A | 7/1998 | Cothran et al. |
| 5,780,703 A | 7/1998 | Chang et al. |
| 5,782,936 A | 7/1998 | Riley |
| 5,798,314 A | 8/1998 | Spencer et al. |
| 5,814,715 A | 9/1998 | Chen et al. |
| 5,817,904 A | 10/1998 | Vic et al. |
| 5,821,394 A | 10/1998 | Schoebrechts et al. |
| 5,847,224 A | 12/1998 | Koga et al. |
| 5,849,978 A | 12/1998 | Benazzi et al. |
| 5,866,735 A | 2/1999 | Cheung et al. |
| 5,882,614 A | 3/1999 | Taylor, Jr. et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,928,488 A | 7/1999 | Newman |
| 5,952,538 A | 9/1999 | Vaughn et al. |
| 5,959,170 A | 9/1999 | Withers, Jr., et al. |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller et al. |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |

(56) References Cited

U.S. PATENT DOCUMENTS

| | | |
|---|---|---|
| 6,034,288 A | 3/2000 | Scott et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,093,306 A | 7/2000 | Hanrahan et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson et al. |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |
| 6,342,200 B1 | 1/2002 | Rouleau et al. |
| 6,368,490 B1 | 4/2002 | Gestermann |
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,491,809 B1 | 12/2002 | Briot et al. |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,627,777 B2 | 9/2003 | Rossi et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,870 B2 | 10/2005 | Yan et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,111 B1 | 5/2006 | DeGroot et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |

(56) References Cited

U.S. PATENT DOCUMENTS

| | | |
|---|---|---|
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |
| 7,282,603 B2 | 10/2007 | Richards |
| 7,285,698 B2 | 10/2007 | Liu et al. |
| 7,304,193 B1 | 12/2007 | Frey et al. |
| 7,342,144 B2 | 3/2008 | Kaizik et al. |
| 7,348,295 B2 | 3/2008 | Zones et al. |
| 7,348,464 B2 | 3/2008 | Waycuilis |
| 7,357,904 B2 | 4/2008 | Zones et al. |
| 7,361,794 B2 | 4/2008 | Grosso |
| 7,365,102 B1 | 4/2008 | Weissman |
| 7,390,395 B2 | 6/2008 | Elomari |
| 7,560,607 B2 | 7/2009 | Waycuilis |
| 7,674,941 B2 | 3/2010 | Waycuilis et al. |
| 7,713,510 B2 | 5/2010 | Harrod et al. |
| 8,008,535 B2 | 8/2011 | Waycuilis |
| 8,173,851 B2 | 5/2012 | Waycuilis et al. |
| 8,198,495 B2 | 6/2012 | Waycuilis et al. |
| 8,232,441 B2 | 7/2012 | Waycuilis |
| 8,282,810 B2 | 10/2012 | Waycuilis |
| 8,367,884 B2 | 2/2013 | Waycuilis |
| 8,373,015 B2 | 2/2013 | Stark et al. |
| 8,415,517 B2 | 4/2013 | Gadewar et al. |
| 8,436,220 B2 | 5/2013 | Kurukchi et al. |
| 8,449,849 B2 | 5/2013 | Gadewar et al. |
| 8,642,822 B2 | 2/2014 | Brickey et al. |
| 2001/0051662 A1 | 12/2001 | Arcuri et al. |
| 2002/0102672 A1 | 8/2002 | Mizrahi |
| 2002/0193649 A1 | 12/2002 | O'Rear et al. |
| 2002/0198416 A1 | 12/2002 | Zhou et al. |
| 2003/0004380 A1 | 1/2003 | Grumann |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2004/0055955 A1 | 3/2004 | Davis |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0171779 A1 | 9/2004 | Matyjaszewski et al. |
| 2004/0187684 A1 | 9/2004 | Elomari |
| 2004/0188271 A1 | 9/2004 | Ramachandraiah et al. |
| 2004/0188324 A1 | 9/2004 | Elomari |
| 2004/0220433 A1 | 11/2004 | Van Der Heide |
| 2005/0027084 A1 | 2/2005 | Clarke |
| 2005/0038310 A1 | 2/2005 | Lorkovic et al. |
| 2005/0042159 A1 | 2/2005 | Elomari |
| 2005/0047927 A1 | 3/2005 | Lee et al. |
| 2005/0148805 A1 | 7/2005 | Jones |
| 2005/0171393 A1 | 8/2005 | Lorkovic |
| 2005/0192468 A1 | 9/2005 | Sherman et al. |
| 2005/0215837 A1 | 9/2005 | Hoffpauir |
| 2005/0218041 A1 | 10/2005 | Yoshida et al. |
| 2005/0234276 A1 | 10/2005 | Waycuilis |
| 2005/0234277 A1 | 10/2005 | Waycuilis |
| 2005/0245771 A1 | 11/2005 | Fong et al. |
| 2005/0245772 A1 | 11/2005 | Fong |
| 2005/0245777 A1 | 11/2005 | Fong |
| 2005/0267224 A1 | 12/2005 | Herling |
| 2006/0025617 A1 | 2/2006 | Begley |
| 2006/0100469 A1 | 5/2006 | Waycuilis |
| 2006/0135823 A1 | 6/2006 | Jun |
| 2006/0138025 A1 | 6/2006 | Zones |
| 2006/0138026 A1 | 6/2006 | Chen |
| 2006/0149116 A1 | 7/2006 | Slaugh |
| 2006/0229228 A1 | 10/2006 | Komon et al. |
| 2006/0229475 A1 | 10/2006 | Weiss et al. |
| 2006/0270863 A1 | 11/2006 | Reiling |
| 2006/0288690 A1 | 12/2006 | Elomari |
| 2007/0004955 A1 | 1/2007 | Kay |
| 2007/0078285 A1 | 4/2007 | Dagle |
| 2007/0100189 A1 | 5/2007 | Stauffer |
| 2007/0129584 A1 | 6/2007 | Basset |
| 2007/0142680 A1 | 6/2007 | Ayoub |
| 2007/0148067 A1 | 6/2007 | Zones |
| 2007/0148086 A1 | 6/2007 | Zones |
| 2007/0149778 A1 | 6/2007 | Zones |
| 2007/0149789 A1 | 6/2007 | Zones |
| 2007/0149819 A1 | 6/2007 | Zones |
| 2007/0149824 A1 | 6/2007 | Zones |
| 2007/0149837 A1 | 6/2007 | Zones |
| 2007/0149838 A1 | 6/2007 | Chretien |
| 2007/0197801 A1 | 8/2007 | Bolk |
| 2007/0197847 A1 | 8/2007 | Liu |
| 2007/0213545 A1 | 9/2007 | Bolk |
| 2007/0238905 A1 | 10/2007 | Arredondo |
| 2007/0238909 A1 | 10/2007 | Gadewar et al. |
| 2007/0276168 A1 | 11/2007 | Garel |
| 2007/0284284 A1 | 12/2007 | Zones |
| 2008/0022717 A1 | 1/2008 | Yoshida et al. |
| 2008/0152555 A1 | 6/2008 | Wang et al. |
| 2008/0171898 A1 | 7/2008 | Waycuilis |
| 2008/0183022 A1 | 7/2008 | Waycuilis |
| 2008/0188697 A1 | 8/2008 | Lorkovic |
| 2008/0200740 A1 | 8/2008 | Waycuilis |
| 2008/0210596 A1 | 9/2008 | Litt et al. |
| 2008/0275279 A1 | 11/2008 | Podkolzin et al. |
| 2008/0275284 A1 | 11/2008 | Waycuilis |
| 2008/0314758 A1 | 12/2008 | Grosso et al. |
| 2009/0005620 A1 | 1/2009 | Waycuilis et al. |
| 2009/0163749 A1 | 6/2009 | Li et al. |
| 2009/0247796 A1 | 10/2009 | Waycuilis et al. |
| 2009/0270655 A1 | 10/2009 | Fong et al. |
| 2009/0306443 A1 | 12/2009 | Stark et al. |
| 2009/0308759 A1 | 12/2009 | Waycuilis |
| 2009/0312586 A1 | 12/2009 | Waycuilis et al. |
| 2009/0326292 A1 | 12/2009 | Waycuilis |
| 2010/0030005 A1 | 2/2010 | Sauer et al. |
| 2010/0087686 A1 | 4/2010 | Fong et al. |
| 2010/0096588 A1 | 4/2010 | Gadewar et al. |
| 2010/0099929 A1 | 4/2010 | Gadewar et al. |
| 2010/0099930 A1 | 4/2010 | Stoimenov et al. |
| 2010/0105972 A1 | 4/2010 | Lorkovic |
| 2010/0234637 A1 | 9/2010 | Fong et al. |
| 2010/0270167 A1 | 10/2010 | McFarland |
| 2011/0015458 A1 | 1/2011 | Waycuilis et al. |
| 2011/0071326 A1 | 3/2011 | Waycuilis |
| 2011/0130597 A1 | 6/2011 | Miller et al. |
| 2011/0198285 A1 | 8/2011 | Wallace |
| 2011/0218372 A1 | 9/2011 | Waycuilis et al. |
| 2011/0218374 A1 | 9/2011 | Waycuilis |
| 2012/0053381 A1 | 3/2012 | Evans et al. |

(56) References Cited

U.S. PATENT DOCUMENTS

| | | | |
|---|---|---|---|
| 2012/0141356 A1 | 6/2012 | Brickey et al. |
| 2012/0245399 A1 | 9/2012 | Kurukchi et al. |
| 2012/0313034 A1 | 12/2012 | Kurukchi et al. |
| 2013/0006024 A1 | 1/2013 | Kurukchi et al. |
| 2013/0046121 A1 | 2/2013 | Kurukchi et al. |
| 2013/0079564 A1 | 3/2013 | Waycuilis |
| 2013/0090504 A1 | 4/2013 | Roscoe et al. |
| 2013/0102820 A1 | 4/2013 | Waycuilis et al. |
| 2013/0102821 A1 | 4/2013 | Waycuilis et al. |
| 2013/0156681 A1 | 6/2013 | Kurukchi et al. |
| 2013/0158324 A1 | 6/2013 | Waycuilis et al. |
| 2013/0178675 A1 | 7/2013 | Kurukchi et al. |
| 2013/0217938 A1 | 8/2013 | Waycuilis et al. |

FOREIGN PATENT DOCUMENTS

| | | |
|---|---|---|
| CA | 1202610 | 4/1986 |
| CA | 2542857 | 5/2005 |
| CA | 2236126 | 8/2006 |
| CA | 2203115 | 9/2006 |
| CA | 2510093 | 12/2006 |
| CA | 2641348 A1 | 8/2007 |
| CA | 2684765 A1 | 11/2008 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |
| EP | 0346612 B1 | 8/1993 |
| EP | 0560546 A1 | 9/1993 |
| EP | 0976705 A1 | 2/2000 |
| EP | 1186591 A2 | 3/2002 |
| EP | 1253126 A1 | 10/2002 |
| EP | 1312411 A2 | 5/2003 |
| EP | 1235769 B1 | 5/2004 |
| EP | 1435349 A2 | 7/2004 |
| EP | 1440939 A1 | 7/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 0/1912 |
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 A | 11/1961 |
| GB | 930341 A | 7/1963 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 | 2/1972 |
| GB | 1446803 | 8/1976 |
| GB | 1542112 | 3/1979 |
| GB | 2095243 A | 9/1982 |
| GB | 2095245 A | 9/1982 |
| GB | 2095249 A | 9/1982 |
| GB | 2116546 A | 9/1982 |
| GB | 2120249 A | 11/1983 |
| GB | 2185754 A | 7/1987 |
| GB | 2191214 A | 12/1987 |
| SU | 694483 A1 | 10/1979 |
| WO | 83/00859 | 3/1983 |
| WO | 85/04863 | 11/1985 |
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/06039 A1 | 4/1993 |
| WO | 93/16798 | 9/1993 |
| WO | 96/22263 | 7/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A1 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/104689 A2 | 11/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006/067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/083427 A2 | 8/2006 |
| WO | 2006/100312 A2 | 9/2006 |
| WO | 2006/104909 A2 | 10/2006 |
| WO | 2006/104914 A1 | 10/2006 |

(56) References Cited

FOREIGN PATENT DOCUMENTS

| WO | 2006/111997 | A1 | 10/2006 |
|---|---|---|---|
| WO | 2006/113205 | A2 | 10/2006 |
| WO | 2006/118935 | A2 | 11/2006 |
| WO | 2007/001934 | A2 | 1/2007 |
| WO | 2007/017900 | A2 | 2/2007 |
| WO | 2007/044139 | A1 | 4/2007 |
| WO | 2007/046986 | A2 | 4/2007 |
| WO | 2007/050745 | A1 | 5/2007 |
| WO | 2007/071046 | A1 | 6/2007 |
| WO | 2007/079038 | A2 | 7/2007 |
| WO | 2007/091009 | A2 | 8/2007 |
| WO | 2007/094995 | A2 | 8/2007 |
| WO | 2007/107031 | A1 | 9/2007 |
| WO | 2007/111997 | A2 | 10/2007 |
| WO | 2007/114479 | A1 | 10/2007 |
| WO | 2007/125332 | A1 | 11/2007 |
| WO | 2007/130054 | A1 | 11/2007 |
| WO | 2007/130055 | A1 | 11/2007 |
| WO | 2007/141295 | A1 | 12/2007 |
| WO | 2007/142745 | A1 | 12/2007 |
| WO | 2008/036562 | A1 | 3/2008 |
| WO | 2008/036563 | A2 | 3/2008 |
| WO | 2008/106318 | A1 | 9/2008 |
| WO | 2008/106319 | A1 | 9/2008 |
| WO | 2008/157043 | A1 | 12/2008 |
| WO | 2008/157044 | A1 | 12/2008 |
| WO | 2008/157045 | A1 | 12/2008 |
| WO | 2008/157046 | A1 | 12/2008 |
| WO | 2008/157047 | A1 | 12/2008 |
| WO | 2009/152403 | A1 | 12/2009 |
| WO | 2009/152405 | A1 | 12/2009 |
| WO | 2009/152408 | A1 | 12/2009 |
| WO | 2010/009376 | A1 | 1/2010 |
| WO | 2011/008573 | A1 | 1/2011 |

OTHER PUBLICATIONS

Abstract of JP 8266888, Method for decomposing aromatic halogen compound, Publication date: Oct. 15, 1996, Inventor: Yuuji et al., esp@cenet database—worldwide.
Abstract of JP 2001031605, Production of 3-hydroxy-1-cycloalkene, Publication date: Feb. 6, 2001, Inventor: Hideo et al., esp@cenet database—worldwide.
Abstract of JP 2004-529189.
Abstract of JP 2004075683, Method for producing optically active halogenohydroxypropyl compound and glycidyl compound, Publication date: Mar. 11, 2004, Inventor: Keisuke et al., esp@cenet database—worldwide.
Abstract of JP 2004189655, Method for fluorinating with microwave, Publication date: Jul. 8, 2004, Inventor: Masaharu et al., esp@cenet database—worldwide.
Abstract of JP 2005075798, Method for producing adamantyl ester compound, Publication date: Mar. 24, 2005, Inventor: Norihiro et al., esp@cenet database—worldwide.
Abstract of JP 2005082563, Method for producing 1,3-adamantanediol, Publication date: Mar. 31, 2005, Inventor: Norihiro et al., esp@cenet database—worldwide.
Abstract of JP 2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP 2005254092, Method of manufacturing alkynes, Publication date: Sep. 22, 2005, Inventor: Shirakawa Eiji, esp@cenet database—worldwide.
Abstract of JP 2006151892, Preparation method of alcohol derivative, Publication date: Jun. 15, 2006, Inventor: Baba Akio et al., esp@cenet database—worldwide.
Abstract of JP 2006152263, Organic-inorganic hybrid-type mesoporous material, method for producing the same, and solid catalyst, Publication date: Jun. 15, 2006, Inventor: Junko et al., esp@cenet database—worldwide.
Abstract of JP 2006193473, Aryl polyadamantane derivative having carboxy or acid anhydride group and method for producing the same, Publication date: Jul. 27, 2006, Inventor: Yasuto et al, esp@cenet database—worldwide.
Abstract of JP 2006231318, Phosphorus containing macromolecule immobilizing palladium catalyst and method for using the same, Publication date: Sep. 7, 2006, Inventor: Osamu et al., esp@cenet database—worldwide.
Abstract of JP 2006263567, Optical resolution method of optical isomer and optical resolution device, Publication date: Oct. 5, 2006, Inventor: Yoshikazu et al., esp@cenet database—worldwide.
Abstract of JP 2006265157, Method for catalytically activating silicated nucleating agent using phosphazene base, Publication date: Oct. 5, 2006, Inventor: Yoshinori et al., esp@cenet database—worldwide.
Abstract of JP 2006306758, Method for producing biaryl compound, Publication date: Nov. 9, 2006, Inventor: Yuji et al., esp@cenet database—worldwide.
Abstract of JP 2007001942, Production method of para-xylene, Publication date: Jan. 11, 2007, Inventor: Kazuyoshi, esp@cenet database—worldwide.
Abstract of JP 2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.
Abstract of JP 2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP 2007061594, Method for decomposing organohalogen compound and mobile decomposition system, Publication date: Mar. 15, 2007, Inventor: Koichi et al., esp@cenet database—worldwide.
Abstract of JP 2007099729, Method for producing alpha-methylstyrene or cumene, Publication date: Apr. 19, 2007, Inventor: Toshio, esp@cenet database—worldwide.
Abstract of RO 119778, Process for preparing perchloroethylene, Publication date: Mar. 30, 2005, Inventor: Horia et al., esp@cenet database—worldwide.
Abstract of WO 0105737, Method for preparing a carboxylic acid, Publication date: Jan. 25, 2001, Inventor: Pascal et al., esp@cenet database—worldwide.
Abstract of WO 0105738, Method for Preparing a carboxylic acid, Publication date: Jan. 25, 2001, Inventor: Pascal et al., esp@cenet database—worldwide.
Abstract of WO 9721656, Method for making fluoroalkanols, Publication date: Jun. 19, 1997, Inventor: Gillet, esp@cenet database—worldwide.
Abstract of WO 9950213, Method for producing dialkyl ethers, Publication date: Oct. 7, 1999, Inventor: Falkowski et al., esp@cenet database—worldwide.
Abstract of WO 2004092099, Method for producing cyclic enols, Publication date: Oct. 28, 2004, Inventor: Friedrich Marko et al., esp@cenet database—worldwide.
Abstract of WO 2006063852, Electroluminescent polymers and use thereof, Publication date: Jun. 22, 2006, Inventor: Buesing Arne et al., esp@cenet database—worldwide.
Abstract of WO 2006076942, Method for the production of synthetic fuels from oxygenates, Publication date: Jul. 27, 2006, Inventor: Rothaemel et al., esp@cenet database—worldwide.
Abstract of WO 2006136135, Method for decarboxylating C—C cross-linking of carboxylic acids with carbon electrophiles, Publication date: Dec. 28, 2006, Inventor: Goossen Lukas et al., esp@cenet database—worldwide.
Abstract of WO 2007028761, Method for chlorinating alcohols, Publication date: Mar. 15, 2007, Inventor: Rohde et al., esp@cenet database—worldwide.
Abstract of WO 2007128842, Catalytic transalkylation of dialkyl benzenes, Publication date: Nov. 15, 2007, Inventor: Goncalvesalmeida et al., esp@cenet database—worldwide.

(56) References Cited

OTHER PUBLICATIONS

Abstract of WO 2007137566, Method for catalytic conversion of organic oxygenated compounds from biomaterials, Publication date: Dec. 6, 2007, Inventor: Reschetilowski, esp@cenet database—worldwide.
Adachi et al., Synthesis of sialyl lewis X ganglioside analogs containing a variable length spacer between the sugar and lipophilic moieties, J. Carbohydrate Chemistry, vol. 17, No. 4-5, 1998, pp. 595-607, XP009081720.
Akhrem et al., Ionic Bromination of Ethane and other alkanes (cycloalkanes) with bromine catalyzed by the polyhalomethane-2AlBr3 aprotic organic superacids under mild conditions, Tetrahedron Letters, vol. 36, No. 51, 1995, pp. 9365-9368, Pergamon, Great Britain.
Bagno et al., Superacid-catalyzed carbonylation of methane, methyl halides, methyl alcohol, and dimethyl ether to methyl acetate and acetic acid, J. Org. Chem. 1990, 55, pp. 4284-4289, Loker Hydrocarbon Research Institute; University of Southern California.
Bakker et al., An exploratory study of the addition reactions of ethyleneglycol, 2-chloroethanol and 1,3-dichloro-2-propanol to 1-dodecene, J. Am. Oil Chem. Soc., vol. 44, No. 9, 1967, pp. 517-521, XP009081570.
Benizri et al., Study of the liquid-vapor equilibrium in the bromine-hydrobromic acid-water system, Hydrogen Energy Vector, 1980, pp. 101-116.
Bouzide et al., Highly selective silver (I) oxide mediated monoprotection of symmetrical diols, Tetrahedron Letters, Elsevier, vol. 38, No. 34, 1997, pp. 5945-5948, XP004094157.
Bradshaw et al., Production of hydrobromic acid from bromine and methane for hydrogen production, Proceedings of the 2001 DOE Hydrogen Program Review, NREL/CP-570-30535, 2001, pp. 1-8.
Chang et al., The conversion of methanol and other O-compounds to hydrocarbons over zeolite catalysts, Journal of Catalysis 47, 1977, Academic Press, Inc., pp. 249-259.
Claude et al., Monomethyl-branching of long n-alkanes in the range from decane to tetracosane on Pt/H-ZSM-22 bifunctional catalyst, Journal of Catalysis 190, 2000, pp. 39-48.
Combined International Search Report and Written Opinion dated Apr. 17, 2007 for PCT/US2006/013394, Applicant: GRT, Inc., pp. 1-13.
Driscoll, Direct methane conversion, Federal Energy Technology Center, U.S. Department of Energy, M970779, pp. 1-10.
Fenelonov, et al., Changes in texture and catalytic activity of nanocrystalline MgO during its transformation to MgCl2 in the reaction with 1-chlorobutane, J. Phys. Chem. B 2001, 105, 2001 American Chemical Society, pp. 3937-3941.
Final Report, Abstract, http://chemelab.ucsd.edu/methanol/memos/final.html, May 9, 2004, pp. 1-7.
Gibson, Phase-transfer synthesis of monoalkyl ethers of oligoethylene glycols, J. Org. Chem. 1980, vol. 45, No. 6, pp. 1095-1098, XP002427776.
http://webbook.nist.gov/, Welcome to the NIST chemistry webbook, Sep. 10, 2007, U.S. Secretary of Commerce on Behalf of the United States of America, pp. 1-2.
Ione, et al., Syntheses of hydrocarbons from compounds containing one carbon atom using bifunctional zeolite catalysts, Solid Fuel Chemistry, Khimiya Tverdogo Topliva, 1982, Allerton Press, Inc., vol. 16, No. 6, pp. 29-43.
Jaumain et al., Direct catalytic conversion of chloromethane to higher hydrocarbons over various protonic and cationic zeolite catalysts as studied by in-situ FTIR and catalytic testing, Studies in Surface Science and Catalysis 130, Elsevier Science B.V., 2000, pp. 1607-1612.
Abstract of BE 812868, Aromatic hydrocarbons prodn. from chlorinated hydrocarbons, Publication date: Sep. 27, 1974, esp@cenet database—worldwide.
Abstract of BE 814900, Volatile aramatic cpds. prodn., Publication date: Sep. 2, 1974, esp@cenet database—worldwide.
Abstract of BR 0210054, Oxidative halogenation of C1 hydrocarbons to halogenated C1 hydrocarbons and integrated processes related thereto, Publication date: Aug. 17, 2004, Inventor: Schweizer et al., esp@cenet database—worldwide.
Abstract of CA 2447761 A1, Oxidative halogenation of C1 hydrocarbons to halogenated C1 hydrocarbons and integrated processes related thereto, Publication date: Nov. 28, 2002, Inventor: Hickman, et al.
Abstract of CA 2471295 A1, Integrated process for synthesizing alcohols, ethers, and olefins from alkanes, Publication date: Jul. 31, 2003, Inventor: Sherman et al.
Abstract of CN 1199039, Pentanol and its production process, Publication date: Nov. 18, 1998, Inventor: Kailun, esp@cenet database—worldwide.
Abstract of CN 1210847, Process for producing low carbon alcohol by directly hydrating low carbon olefines, Publication date: Mar. 17, 1999, Inventor: Zhenguo et al., esp@cenet database—worldwide.
Abstract of CN 1321728, Method for preparing aromatic hydrocarbon and hydrogen gas by using law-pressure gas, Publication date: Nov. 14, 2001, Inventor: Jie et al., esp@cenet database—worldwide.
Abstract of CN 1451721, Process for non-catalytic combustion deoxidizing coal mine gas for producing methanol, Publication date: Oct. 29, 2003, Inventor: Pengwan et al., esp@cenet database—worldwide.
Abstract of CN 1623969, Method for preparing 1, 4-benzene dimethanol, Publication date: Jun. 8, 2005, Inventor: Jiarong et al., esp@cenet database—worldwide.
Abstract of CN 1657592, Method for converting oil to multiple energy fuel product, Publication date: Aug. 24, 2005, Inventor: Li, esp@cenet database—worldwide.
Abstract of CN 1687316, Method for producing biologic diesel oil from rosin, Publication date: Oct. 26, 2005, Inventor: Jianchun et al., esp@cenet database—worldwide.
Abstract of CN 1696248, Method for synthesizing biologic diesel oil based on ion liquid, Publication date: Nov. 16, 2005, Inventor: Sun, esp@cenet database—worldwide.
Abstract of CN 1699516, Process for preparing bio-diesel-oil by using miroalgae fat, Publication date: Nov. 23, 2005, Inventor: Miao, esp@cenet database—worldwide.
Abstract of CN 1704392, Process for producing alkylbenzene, Publication date: Dec. 7, 2005, Inventor: Gao, esp@cenet database—worldwide.
Abstract of CN 1724612, Biological diesel oil catalyst and method of synthesizing biological diesel oil using sai catalyst, Publication date: Jan. 25, 2006, Inventor: Gu, esp@cenet database—worldwide.
Abstract of CN 1986737, Process for producing biodiesel oil with catering waste oil, Publication date: Jun. 27, 2007, Inventor: Chen, esp@cenet database—worldwide.
Abstract of CN 100999680, Esterification reaction tech. of preparing biodiesel by waste oil, Publication date: Jul. 18, 2007, Inventor: Weiming, esp@cenet database—worldwide.
Abstract of CN 101016229, Refining method for bromomeoamyl alcohol, Publication date: Aug. 15, 2007, Inventor: Tian, esp@cenet database—worldwide.
Abstract of DE 3209964, Process for the preparation of chlorinated hydrocarbons, Publication date: Nov. 11, 1982, Inventor: Pyke et al., esp@cenet database—worldwide.
Abstract of DE 3210196, Process for the preparation of a monochlorinated olefin, Publication date: Jan. 5, 1983, Inventor: Pyke et al., esp@cenet database—worldwide.
Abstract of DE 3226028, Process for the preparation of monochlorinated olefin, Publication date: Feb. 3, 1983, Inventor: Pyke et al., esp@cenet database—worldwide.
Abstract of DE 3334225, Process for the preparation of 1,2-dichloroethane, Publication date: Apr. 4, 1985, Inventor: Hebgen et al., esp@cenet database—worldwide.
Abstract of DE 4232056, 2,5-Di:methyl-hexane-2,5-di:ol continuous prodn. from tert. butanol-by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE 4434823, Continuous prodn. of hydroxy-benzyl alkyl ether, Publication date: Apr. 4, 1996, Inventor: Stein et al., esp@cenet database—worldwide.

(56) References Cited

OTHER PUBLICATIONS

Abstract of EP 0021497 (A1), Synthesis of polyoxyalkylene glycol monoalkyl ethers., Publication date: Jan. 7, 1981, Inventor: Gibson, esp@cenet database—worldwide.
Abstract of EP 0039471, Process for the preparation of 2-chloro-1,1,1,2,3,3,3-heptafluoropropane., Publication date: Nov. 11, 1981, Inventor: Von Halasz, esp@cenet database—worldwide.
Abstract of EP 0101337, Process for the production of methylene chloride., Publication date: Feb. 22, 1984, Inventor: Olah et al., esp@cenet database—worldwide.
Abstract of EP 0235110, Process for the stabilization of silicalite catalysts., Publication date: Sep. 2, 1987, Inventor: Debras et al., esp@cenet database—worldwide.
Abstract of EP 0407989, Method for the production of 1,1,1-trifluoro-2,2-dichloroethane by photochlorination., Publication date: Jan. 16, 1991, Inventor: Cremer et al., esp@cenet database—worldwide.
Abstract of EP 0442258, Process for the preparation of a polyunsaturated olefin., Publication date: Aug. 21, 1991, Inventor: Gaudin et al., esp@cenet database, worldwide.
Abstract of EP 0465294, Process for the preparation of unsaturated bromides., Publication date: Jan. 8, 1992, Inventor: Decaudin et al., esp@cenet database—worldwide.
Abstract of EP 0549387, Synthesis of n-perfluorooctylbromide., Publication date: Jun. 30, 1993, Inventor: Drivon et al., esp@cenet database—worldwide.
Abstract of EP 0850906, Process and apparatus for the etherification of olefinic hydrocarbon feedstocks, Publication date: Jul. 1, 1998, Inventor: Masson, esp@cenet database—worldwide.
Abstract of EP 0858987, Process for conversion of lighter alkanes to higher hydrocarbons, Publication date: Aug. 19, 1998, Inventor: Amariglio, et al., esp@cenet database—worldwide.
Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.
Abstract of EP 1404636, Integrated process for synthesizing alcohols and ethers from alkanes, Publication date: Apr. 7, 2004, Inventor: Zhou et al., esp@cenet database—worldwide.
Abstract of EP 1435349 A2, Integrated process for synthesizing alcohols and ethers from alkanes, Publication date: Jul. 7, 2004, Inventor: Zhou et al.
Abstract of EP 1474371, Integrated process for synthesizing alcohols, ethers, and olefins from alkanes, Publication date: Nov. 10, 2004, Inventor: Zhou et al., esp@cenet database—worldwide.
Abstract of FR 2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR2880019, Manufacturing 1,2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR 2883870, Formation of 1,2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR 2883871, Preparing 1,2-dichloroethane comprises cracking hydrocarbon to form mixture, sending mixture into storage reservoir, supplying mixture into chlorination and/or oxychloration reactor, and separating 1,2- dichloroethane from reactor, Publication date: Oct. 6, 2006, Inventor: Balthasart et al., esp@cenet database—worldwide.
Abstract of IT 1255246, Process for the preparation of dinitrodiphenylmethanes, Publication date: Oct. 20, 1995, Applicant: Enichem Spa et al., esp@cenet database—worldwide.

Abstract of IT 1255358, Process for the synthesis of 1,4-butanediol, Publication date: Oct. 31, 1995, Inventor: Ricci Marco, esp@cenet database—worldwide.
Abstract of JP 2142740, Production of fluoroalcohol, Publication date: May 31, 1990, Inventor: Tsutomu et al., esp@cenet database—worldwide.
Abstract of JP 2144150, Chemical process and catalyst used therefore, Publication date: Jun. 1, 1990, Inventor: Deidamusu et al., esp@cenet database—worldwide.
Abstract of JP 4305542, Production of halogenated hydrocarbon compounds, Publication date: Oct. 28, 1992, Inventor: Shinsuke et al., esp@cenet database—worldwide.
Abstract of JP 6172225, Method for fluorinating halogenated hydrocarbon, Publication date: Jun. 21, 1994, Inventor: Takashi et al., esp@cenet database—worldwide.
Abstract of JP 6206834, Production of Tetrachloroethanes, Publication date: Jul. 26, 1994, Inventor: Toshiro et al., esp@cenet database—worldwide.
JLM Technology Ltd., The Miller GLS Technology for conversation of light hydrocarbons to alcohols, New Science for the Benefit of Humanity, May 31, 2000; pp. 1-10.
Kirk-Othmer, Encyclopedia of Chemical Technology, 4th Edition, vol. 1, A Wiley-Interscience Publication, John Wiley & Sons, 1991, pp. 946-997.
Liu et al., Higher hydrocarbons from methane condensation mediated by HBr, Journal of Molecular Catalysis A: Chemical 273, Elsevier B.V., 2007, pp. 14-20.
Loiseau et al., Multigram synthesis of well-defined extended bifunctional polyethylene glycol (PEG) chains, J. Org. Chem., vol. 69, No. 3, XO-002345040, 2004, pp. 639-647.
Lorkovic et al., A novel integrated process for the functionalization of methane and ethane: bromine as mediator, Catalysis Today 98, 2004, pp. 317-322.
Lorkovic et al., C1 oxidative coupling via bromine activation and tandem catalytic condensation and neutralization over CaO/zeolite composites II. Product distribution variation and full bromine confinement, Catalysis Today 98, 2004, pp. 589-594.
Lorkovic et al., C1 coupling via bromine activation and tandem catalytic condensation and neutralization over CaO/zeolite composites, Chem. Comm. 2004, pp. 566-567.
Mihai, et al., Application of Bronsted-type LFER in the study of the phospholipase C Mechanism, J. Am. Chem. Soc., vol. 125, No. 11, XP-002427777, 2003, pp. 3236-3242.
Mishakov et al., Nanocrystalline MgO as a dehydrohalogenation catalyst, Journal of Catalysis 206, Elsevier Science, USA, 2002, pp. 40-48.
Mochida, et al., The catalytic dehydrohalogenation of haloethanes on solid acids and bases, Bulletin of the Chemical Society of Japan, vol. 44, Dec. 1971, pp. 3305-3310.
Motupally et al., Recycling chlorine from hydrogen chloride, The Electrochemical Society Interface, Fall 1998, pp. 32-36.
Murray et al., Conversion of methyl halides to hydrocarbons on basic zeolites: a discovery by in situ NMR, J. Am. Chem. Soc., 1993, vol. 115, pp. 4732-4741.
Nishikawa et al., Ultrasonic relaxations in aqueous solutions of alcohols and the balance between hydrophobicity and hydrophilicity of the solutes, J. Phys. Chem., vol. 97, No. 14, XP-002427775, 1993, pp. 3539-3544.
Olah et al., Antimony pentafluoride/graphite catalyzed oxidative carbonylation of methyl halides with carbon monoxide and copper oxides (or copper/oxygen) to methyl acetate, J. Org. Chem. 1990, 55, pp. 4293-4297.
Olah et al., Antimony pentafluoride/graphite catalyzed oxidative conversion of methyl halides with copper oxides (or copper/oxygen) to dimethyl ether, J. Org. Chem. 1990, 55, pp. 4289-4293.
Olah, Electrophilic methane conversion, American Chemical Society, Acc. Chem. Res. 1987, 20, pp. 422-428.
Olah, Hydrocarbons through methane derivatives, Hydrocarbon Chemistry, 1995, pp. 89-90, John Wiley & Sons, Inc.
Olah et al., Hydrocarbons through methane derivatives, Hydrocarbon Chemistry, 2nd Edition, 2003, pp. 123, 149, and 153, John Wiley & Sons, Inc.

(56) References Cited

OTHER PUBLICATIONS

Olah et al., Onium Ylide Chemistry. 1. Bifunctional acid-base-catalyzed conversion of heterosubstituted methanes into ethylene and derived hydrocarbons. The Onium Ylide mechanism of the C1-C2 conversion. J. Am. Chem. Soc. 1984, 106, pp. 2143-2149.

Olah et al., Selective monohalogenation of methane over supported acid or platinum metal catalysts and hydrolysis of methyl halides over y-alumina-supported metal oxide/hydroxide catalysts. A feasible path for the oxidative conversion of methane into methyl alcohol/dimethyl ether., J. Am. Chem. Soc. 1985, 107, pp. 7097-7105.

Prelog et al., 234. Chirale 2, 2'-polyoxaalkano-9,9'-spirobifluorene, Helvetica Chimica ACTA, vol. 62, No. 7, 1979 pp. 2285-2302.

Rakoff et al., Quimica Organica Fundamental, Organic Chemistry, The Macmillan Company, 1966, pp. 58-63 and 76-77.

Richards, et al., Nanocrystalline ultra high surface area magnesium oxide as a selective base catalyst, Scripta Materialia, 44, 2001, pp. 1663-1666, Elsevier Science Ltd.

Shimizu et al., Gas-Phase electrolysis of hydrobromic acid using PTFE-bonded carbon electrode, Int. J. Hydrogen Energy, vol. 13, No. 6, pp. 345-349, 1988.

Smirnov et al., Selective bromination of alkanes and arylalkanes with CBr4, Mendeleev Commun., 2000, pp. 175-176.

Sun et al., Nanocrystal metal oxide—Chlorine adducts: selective catalysts for chlorination of alkanes, J. Am. Chem. Soc., 1999, 121, pp. 5587-5588.

Sun et al., A general integrated process for synthesizing olefin oxides, Chem. Commun., The Royal Society of Chemistry 2004, pp. 2100-2101.

Tamura et al., The reactions of grignard reagents with transition metal halides: Coupling, disproportionation, and exchange with olefins, Bulletin of the Chemical Society of Japan, vol. 44, Nov. 1971, pp. 3063-3073.

Taylor et al., Direct conversion of methane to liquid hydrocarbons through chlorocarbon intermediates, 1988, Elsevier Science Publishers B.V. Amsterdam, Netherlands, pp. 483-489.

Taylor, Conversion of substituted methanes over ZSM-catalysts, 2000, pp. 3633-3638, Studies in Surface Science and Catalysis 130, Elsevier Science B.V.

Taylor, PETC's on-site naural gas conversion efforts, Preprints of the Fuel Division, 208th National Meeting of the American Chemical Society, 39 (4), 1994, pp. 1228-1232.

Thomas et al., Catalytically active centres in porous oxides: design and performance of highly selective new catalysts, Chem. Commun., 2001, pp. 675-687.

Thomas et al., Synthesis and characterization of a catalytically active nickel-silicoaluminophosphate catalyst for the conversion of methanol to ethene, American Chemical Society, 1991, 3, pp. 667-672.

Van Velzen et al., HBr electrolysis in the Ispra mark 13A flue gas desulphurization process: electrolysis in a DEM cell, Journal of Applied Electrochemistry, 20, 1990, pp. 60-68.

Wagner et al., Reactions of VX, GD, and HD with nanosize CaO: autocatalytic dehydrohalogenation of HD, J. Phys. Chem. B 2000, 104, pp. 5118-5123, 2000 American Chemical Society.

Wauters et al., Electrolytic membrane recovery of bromine from waste hydrogen bromide streams, AIChE Journal, Oct. 1998, vol. 44, No. 10, pp. 2144-2148.

Weissermel et al., Industrial Organic Chemistry, 3rd Edition, 1997, pp. 160-162, and 208.

Whitesides et al., Nuclear magnetic resonance spectroscopy. The effect of structure on magnetic nonequivalence due to molecular asymmetry, J. Am. Chem. Soc., vol. 86, No. 13, 1964, pp. 2628-2634, XP002427774.

Yilmaz et al., Bromine mediated partial oxidation of ethane over nanostructured zirconia supported metal oxide/bromide, Microporous and Mesoporous Materials, 79, 2005, Science Direct, Elsevier, pp. 205-214.

Zhou et al., An integrated process for partial oxidation of alkanes, Chem. Commun., 2003, The Royal Society of Chemistry, pp. 2294-2295.

ZSM-5 Catalyst, http://chemelba.ucsd.edu/methanol/memos/ZSM-5.html, Nov. 6, 2003, p. 1.

Abstract of GB 998681(A), Improvements in or relating to the recovery of bromine from bromine-containing materials, Publication date: Jul. 21, 1965, Applicant: Electro Chimie Metal+, espacenet worldwide database.

Abstract of JP 55-073619, Condensation of methyl chloride through dehydrochlorination, Publication date: Jun. 3, 1980, Inventor: Shigeo et al., http://www19.ipdl.inpit.go.jp/PA1/result . . . .

Hannus, Adsorption and transformation of halogenated hydrocarbons over zeolites, Applied Catalysis A: General 189, 1999, XP-002634422, pp. 263-276.

Howe, Zeolite catalysts for dehalogenation processes, Applied Catalysis A: General 271, 2004, XP-002634421, pp. 3-11.

Li et al., Pyrolysis of Halon 1301 over zeolite catalysts, Microporous and Mesoporous Materials 35-36, 2000, XP-002634423, pp. 219-226.

Chretien; Process for the Adjustment of the HHV in the LNG Plants; 23rd World Gas Conference; Amsterdam 2006; Jun. 5-Sep. 2006; pp. 1-14.

Yang et al.; Maximising the Value of Surplus Ethane and Cost-Effective Design to Handle Rich LNG; publ. date Jun. 1, 2007; pp. 1-13.

Abstract of JP Publication No. 08-283182; Production of Hydrochloromethanes; Published Oct. 29, 1996; Inventor: Miyazaki Kojiro et al., http://www19/ipdl.inpit.go.jp . . . .

Abstract of WO 96/00696; Method and Apparatus for Recovering Bromine from a Liquid Effluent; Published Jun. 11, 1996; Inventor: Mulet, Jean-Charles et al.

Henshuiinkai, Kagaku Daijiten; Kagaku Daijiten 4, Japan, Kyoritsu Publisher, Oct. 15, 1963; pp. 652-654.

Jackisch, Philip F.; "Bromine" in Kirk-Othmer Encyclopedia of Chemical Technology, 4th Edition, vol. 4; pp. 536-537, 548-550, 560; Published 1992, John Wiley & Sons, Inc. USA.

Jacobson, C.A.; "Encyclopedia of Chemical Reactions"; vol. 1, 1946; p. 722.

Kesner, Miri; "How is Bromine Produced" in Bromine Compounds from the Dead Sea, Israel Products in the Service of People; pp. 3, 5, 78, 87; First published in Hebrew in Israel in 1999 by the Department of Science Teaching; The Weizmann Institute of Science.

Lewis, Sr., Richard J.; "Hawley's Condensed Chemical Dictionary", 15th Edition; Jan. 2007; John Wiley & Sons; p. 181.

Mills, Jack F.; "Bromine" in Ullmann's Encyclopedia of Industrial Chemistry, Fifth, Completely Revised Edition, vol. A4; pp. 391 and 397; Published 1985; VCH Verlagsgesellschaft mbH, Federal Republic of Germany.

U.S. Office Communication from U.S. Appl. No. 10/365,346 dated Jun. 12, 2006.

U.S. Office Communication from U.S. Appl. No. 10/826,885 dated Oct. 31, 2005.

U.S. Office Communication from U.S. Appl. No. 10/826,885 dated Apr. 19, 2006.

U.S. Office Communication from U.S. Appl. No. 10/826,885 dated Jul. 27, 2006.

U.S. Office Communication from U.S. Appl. No. 10/826,885 dated Nov. 2, 2006.

U.S. Office Communication from U.S. Appl. No. 10/826,885 dated Jan. 24, 2007.

U.S. Office Communication from U.S. Appl. No. 10/893,418 dated Jun. 14, 2007.

U.S. Office Communication from U.S. Appl. No. 10/893,418 dated Jan. 2, 2008.

U.S. Office Communication from U.S. Appl. No. 11/091,130 dated Oct. 3, 2007.

U.S. Office Communication from U.S. Appl. No. 11/101,886 dated Jan. 24, 2007.

U.S. Office Communication from U.S. Appl. No. 11/254,438 dated Jan. 24, 2007.

U.S. Office Communication from U.S. Appl. No. 11/254,438 dated Nov. 1, 2007.

U.S. Office Communication from U.S. Appl. No. 11/778,479 dated Feb. 22, 2010.

(56) References Cited

OTHER PUBLICATIONS

U.S. Office Communication from U.S. Appl. No. 12/112,926 dated Jan. 16, 2009.
U.S. Office Communication from U.S. Appl. No. 12/112,926 dated Sep. 14, 2009.
U.S. Office Communication from U.S. Appl. No. 12/112,926 dated Jan. 7, 2010.
U.S. Office Communication from U.S. Appl. No. 12/112,926 dated Jul. 22, 2010.
U.S. Office Communication from U.S. Appl. No. 12/112,926 dated Jan. 7, 2011.
U.S. Office Communication from U.S. Appl. No. 12/123,924 dated Mar. 19, 2010.
U.S. Office Communication from U.S. Appl. No. 12/123,924 dated Aug. 30, 2010.
U.S. Office Communication from U.S. Appl. No. 12/139,135 dated Nov. 24, 2010.
U.S. Office Communication from U.S. Appl. No. 12/139,135 dated Apr. 14, 2011.
U.S. Office Communication from U.S. Appl. No. 12/139,135 dated Oct. 14, 2011.
U.S. Office Communication from U.S. Appl. No. 12/139,135 dated Nov. 7, 2013.
U.S. Office Communication from U.S. Appl. No. 12/477,307 dated Oct. 7, 2011.
U.S. Office Communication from U.S. Appl. No. 12/477,307 dated Feb. 27, 2012.
U.S. Office Communication from U.S. Appl. No. 12/477,319 dated Jul. 22, 2011.
U.S. Office Communication from U.S. Appl. No. 12/502,024 dated Oct. 26, 2010.
U.S. Office Communication from U.S. Appl. No. 12/502,024 dated May 31, 2011.
U.S. Office Communication from U.S. Appl. No. 12/502,024 dated Sep. 16, 2011.
U.S. Office Communication from U.S. Appl. No. 12/715,526 dated Feb. 17, 2011.
U.S. Office Communication from U.S. Appl. No. 12/715,526 dated May 24, 2011.
U.S. Office Communication from U.S. Appl. No. 12/715,526 dated Jan. 4, 2012.
U.S. Office Communication from U.S. Appl. No. 12/792,335 dated Aug. 17, 2012.
U.S. Office Communication from U.S. Appl. No. 12/792,335 dated Jan. 2, 2013.
U.S. Office Communication from U.S. Appl. No. 12/957,036 dated Aug. 16, 2012.
U.S. Office Communication from U.S. Appl. No. 13/053,540 dated Aug. 6, 2013.
U.S. Office Communication from U.S. Appl. No. 13/053,540 dated Jan. 8, 2014.
U.S. Office Communication from U.S. Appl. No. 13/117,785 dated Mar. 14, 2013.
U.S. Office Communication from U.S. Appl. No. 13/117,785 dated Apr. 22, 2013.
U.S. Office Communication from U.S. Appl. No. 13/157,584 dated May 11, 2012.
U.S. Office Communication from U.S. Appl. No. 13/157,584 dated Aug. 29, 2012.
U.S. Office Communication from U.S. Appl. No. 13/173,847 dated Sep. 6, 2013.
U.S. Office Communication from U.S. Appl. No. 13/173,847 dated Jan. 21, 2014.
U.S. Office Communication from U.S. Appl. No. 13/212,291 dated May 10, 2013.
U.S. Office Communication from U.S. Appl. No. 13/269,683 dated Jun. 6, 2013.
U.S. Office Communication from U.S. Appl. No. 13/647,002 dated Jun. 5, 2013.
U.S. Office Communication from U.S. Appl. No. 13/679,600 dated Jan. 17, 2014.
U.S. Office Communication from U.S. Appl. No. 13/705,106 dated Feb. 3, 2014.
U.S. Office Communication from U.S. Appl. No. 13/713,926 dated Jan. 30, 2014.
U.S. Appl. No. 60/487,364, filed Jul. 15, 2003, Lorkovic et al.
U.S. Appl. No. 60/559,844, filed Apr. 6, 2004, Sherman et al.
U.S. Appl. No. 60/765,115, filed Feb. 3, 2006, Gadewar et al.
U.S. Office Communication from U.S. Appl. No. 12/139,135 dated Jun. 19, 2014.
U.S. Office Communication from U.S. Appl. No. 13/760,291 dated Apr. 4, 2014.

CH3Br CONVERSION & PRODUCT SELECTIVITY vs. TEMP
ZSM-5 CATALYST  GHSV 94 hr-1  CH3Br 27 mol%

◇ CH3Br CONV.
□ CH4 SELECT.
△ C3+ SELECT.

CH3Br CONVERSION & PRODUCT SELEVTIVITY
over ZSM-5

- CH3Br CONV.
- C2 SELECT.
- C3 SELECT.
- C4 SELECT.
- C5 SELECT.
- C6 SELECT.
- C7+ SELECT.

PROCESS FOR CONVERTING GASEOUS ALKANES TO LIQUID HYDROCARBONS

BACKGROUND OF THE INVENTION

1. Field of the Invention

The present invention relates to a process for converting lower molecular weight, gaseous alkanes to olefins, higher molecular weight hydrocarbons, or mixtures thereof that may be useful as fuels or monomers and intermediaries in the production of fuels or chemicals, such as lubricant and fuel additives, and more particularly, in one or more embodiments, to a process wherein a gas containing lower molecular weight alkanes is reacted with a dry bromine vapor to form alkyl bromides and hydrobromic acid which in turn are reacted over a crystalline alumino-silicate catalyst to form olefins, higher molecular weight hydrocarbons or mixtures thereof.

2. Description of Related Art

Natural gas, which is primarily composed of methane and other light alkanes, has been discovered in large quantities throughout the world. Many of the locales in which natural gas has been discovered are far from populated regions which have significant gas pipeline infrastructure or market demand for natural gas. Due to the low density of natural gas, transportation thereof in gaseous form by pipeline or as compressed gas in vessels is expensive. Accordingly, practical and economic limits exist to the distance over which natural gas may be transported in gaseous form. Cryogenic liquefaction of natural gas (LNG) is often used to more economically transport natural gas over large distances. However, this LNG process is expensive and there are limited regasification facilities in only a few countries that are equipped to import LNG Another use of methane is as feed to processes for the production of methanol. Methanol is made commercially via conversion of methane to synthesis gas (CO and $H_2$) at high temperatures (approximately 1000° C.) followed by synthesis at high pressures (approximately 100 atmospheres). There are several types of technologies for the production of synthesis gas from methane. Among these are steam-methane reforming (SMR), partial oxidation (POX), autothermal reforming (ATR), gas-heated reforming (GHR), and various combinations thereof. SMR and GHR operate at high pressures and temperatures, generally in excess of 600° C., and require expensive furnaces or reactors containing special heat and corrosion-resistant alloy tubes filled with expensive reforming catalyst. POX and ATR processes operate at high pressures and even higher temperatures, generally in excess of 1000° C. As there are no known practical metals or alloys that can operate at these temperatures, complex and costly refractory-lined reactors and high-pressure waste-heat boilers to quench and cool the synthesis gas effluent are required. Also, significant capital cost and large amounts of power are required for compression of oxygen or air to these high-pressure processes. Thus, due to the high temperatures and pressures involved, synthesis gas technology is expensive, resulting in a high cost methanol product which limits higher-value uses thereof, such as for chemical feedstocks and solvents. Furthermore production of synthesis gas is thermodynamically and chemically inefficient, producing large excesses of waste heat and unwanted carbon dioxide, which tends to lower the conversion efficiency of the overall process. Fischer-Tropsch Gas-to-Liquids (GTL) technology can also be used to convert synthesis gas to heavier liquid hydrocarbons, however investment cost for this process is even higher. In each case, the production of synthesis gas represents a large fraction of the capital costs for these methane conversion processes.

Numerous alternatives to the conventional production of synthesis gas as a route to methanol or synthetic liquid hydrocarbons have been proposed. However, to date, none of these alternatives has attained commercial status for various reasons. Some of the previous alternative prior-art methods, such as disclosed in U.S. Pat. No. 5,243,098 or 5,334,777 to Miller, teach reacting a lower alkane, such as methane, with a metallic halide to form a metal halide and hydrohalic acid which are in turn reduced with magnesium oxide to form the corresponding alkanol. However, halogenation of methane using chlorine as the preferred halogen results in poor selectivity to the monomethyl halide ($CH_3Cl$), resulting in unwanted by-products such as $CH_2Cl_2$ and $CHCl_3$ which are difficult to convert or require severe limitation of conversion per pass and hence very high recycle rates.

Other prior art processes propose the catalytic chlorination or bromination of methane as an alternative to generation of synthesis gas (CO and $H_2$). To improve the selectivity of a methane halogenation step in an overall process for the production of methanol, U.S. Pat. No. 5,998,679 to Miller teaches the use of bromine, generated by thermal decomposition of a metal bromide, to brominate alkanes in the presence of excess alkanes, which results in improved selectivity to mono-halogenated intermediates such as methyl bromide. To avoid the drawbacks of utilizing fluidized beds of moving solids, the process utilizes a circulating liquid mixture of metal chloride hydrates and metal bromides. Processes described in U.S. Pat. No. 6,462,243 B1, U.S. Pat. No. 6,472, 572 B1, and U.S. Pat. No. 6,525,230 to Grosso are also capable of attaining higher selectivity to mono-halogenated intermediates by the use of bromination. The resulting alkyl bromide intermediates such as methyl bromide, are further converted to the corresponding alcohols and ethers, by reaction with metal oxides in circulating beds of moving solids. Another embodiment of U.S. Pat. No. 6,525,230 avoids the drawbacks of moving beds by utilizing a zoned reactor vessel containing a fixed bed of metal bromide/oxide solids that is operated cyclically in four steps. While certain ethers, such as dimethyl ether ("DME") are a promising potential diesel engine fuel substitute, as of yet, there currently exists no substantial market for DME, and hence an expensive additional catalytic process conversion step would be required to convert DME into a currently marketable product. Other processes have been proposed which circumvent the need for production of synthesis gas, such as U.S. Pat. No. 4,467,130 to Olah in which methane is catalytically condensed into gasoline-range hydrocarbons via catalytic condensation using superacid catalysts. However, none of these earlier alternative approaches have resulted in commercial processes.

It is known that substituted alkanes, in particular methanol, can be converted to olefins and gasoline boiling-range hydrocarbons over various forms of crystalline alumino-silicates also known as zeolites. In the Methanol to Gasoline (MTG) process, a shape selective zeolite catalyst, ZSM-5, is used to convert methanol to gasoline. Coal or methane gas can thus be converted to methanol using conventional technology and subsequently converted to gasoline. However due to the high cost of methanol production, and at current or projected prices for gasoline, the MTG process is not considered economically viable. Thus, a need exists for an economic process for the conversion of methane and other alkanes found in natural gas to olefins, higher molecular weight hydrocarbons or mixtures thereof which, due to their higher density and value, are more economically transported thereby significantly aiding development of remote natural gas reserves. Further, a need exists for such a process that is relatively inexpensive, safe and simple.

SUMMARY OF THE INVENTION

To achieve the foregoing and other objects, and in accordance with the purposes of the present invention, as embodied and broadly described herein, one characterization of the present invention is a process comprising: separating hydrobromic acid from a gaseous stream comprising hydrobromic acid and hydrocarbons; converting said hydrobromic acid to at least bromine; and contacting said bromine with gaseous alkanes to form bromination products comprising alkyl bromides.

In another characterization of the present invention, a process is provided that comprises: contacting a gaseous stream comprising hydrobromic acid and hydrocarbons with an aqueous solution comprising a base selected from the group consisting of a metal hydroxide, a metal oxy-bromide species, and combinations thereof such that the hydrobromic acid is neutralized to form a metal bromide salt in the aqueous solution; oxidizing said aqueous solution containing said metal bromide salt to form oxidation products comprising bromine and said base; separating said bromine from said aqueous solution comprising said base; and contacting said bromine with gaseous alkanes to form alkyl bromides.

In another characterization of the present invention, a process is provided that comprises: contacting a gaseous stream comprising hydrobromic acid and hydrocarbons with water, wherein said hydrobromic acid dissolves in said water to form an aqueous solution comprising said water and said hydrobromic acid; neutralizing said hydrobromic acid to form a metal bromide salt; oxidizing said metal bromide salt to form an oxidation product comprising bromine; and contacting said bromine with gaseous alkanes to form bromination products comprising alkyl bromides.

In another characterization of the present invention, a process is provided that comprises: reacting hydrobromic acid with a metal oxide to form reaction products comprising a metal bromide and steam, wherein said hydrobromic acid is contained in a gaseous stream comprising said hydrobromic acid and hydrocarbons; reacting said metal bromide with a gas comprising oxygen to form reaction products comprising bromine and said metal oxide; and contacting said bromine with gaseous alkanes to form bromination products comprising alkyl bromides.

BRIEF DESCRIPTION OF THE DRAWINGS

The accompanying drawings, which are incorporated in and form a part of the specification, illustrate the embodiments of the present invention and, together with the description, serve to explain the principles of the invention.

In the drawings.

DETAILED DESCRIPTION OF THE PREFERRED EMBODIMENTS

Figure 2:
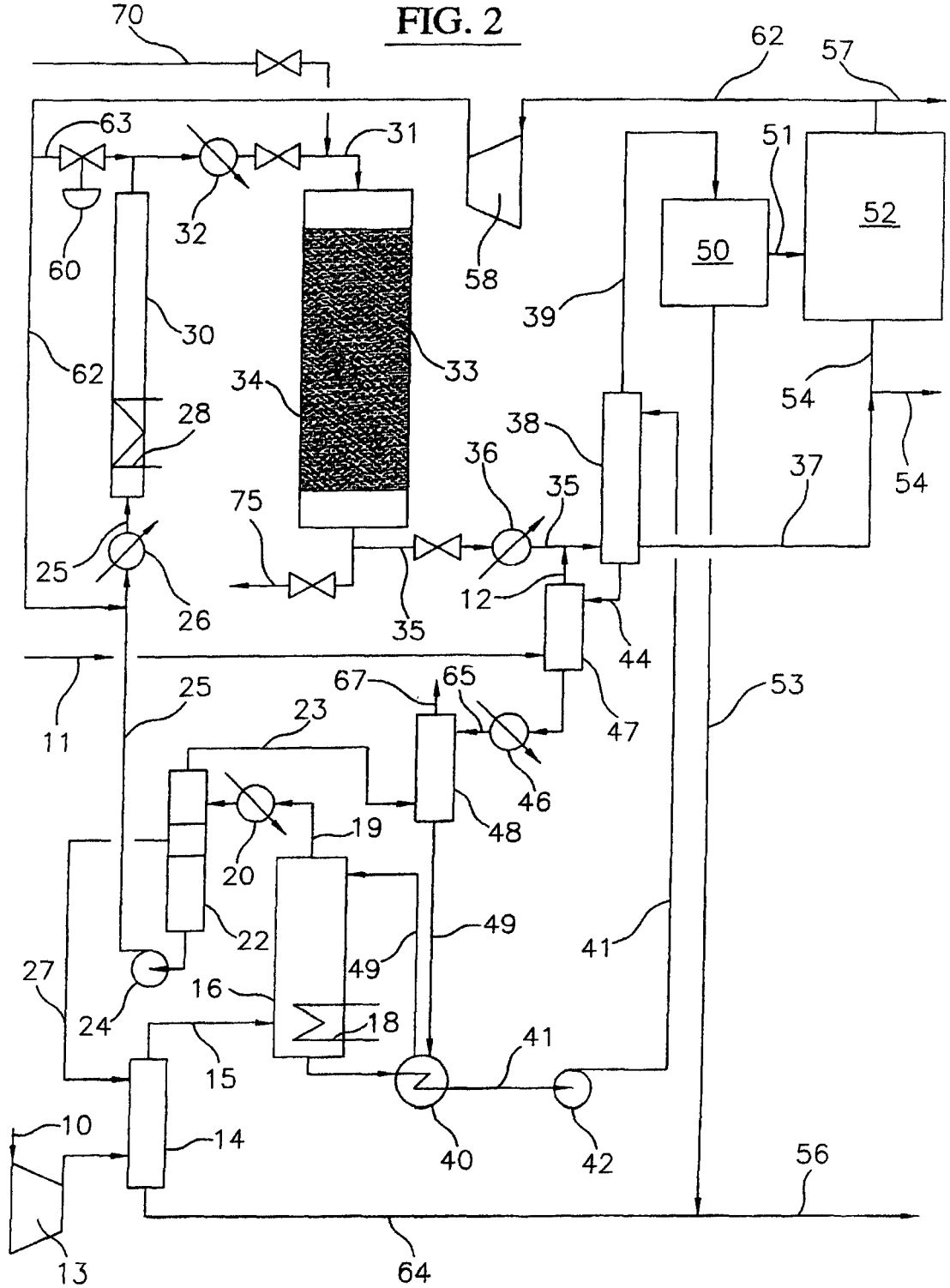
FIG. 2 is a schematic view of one embodiment of the process of the present invention.
Figure 3:
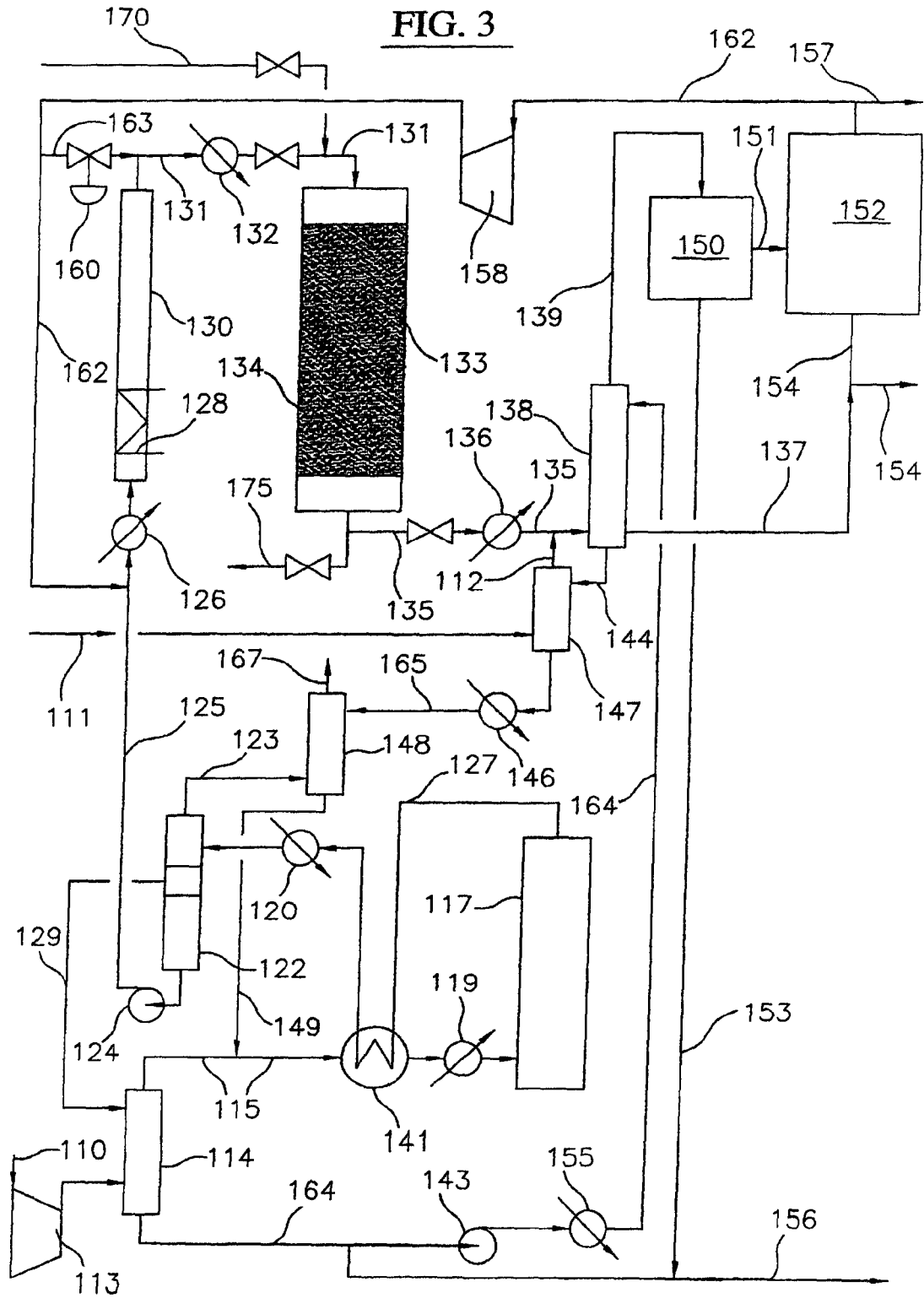
FIG. 3 is a schematic view of another embodiment of process of the present invention.

As utilized throughout this description, the term "lower molecular weight alkanes" refers to methane, ethane, propane, butane, pentane or mixtures thereof. As also utilized throughout this description, "alkyl bromides" refers to mono, di, and tri brominated alkanes. Also, the feed gas in lines 11 and 111 in the embodiments of the process of the present invention as illustrated in FIGS. 2 and 3, respectively, is preferably natural gas which may be treated to remove sulfur compounds and carbon dioxide. In any event, it is important to note that small amounts of carbon dioxide, e.g. less than about 2 mol %, can be tolerated in the feed gas to the process of the present invention.

Figure 1:
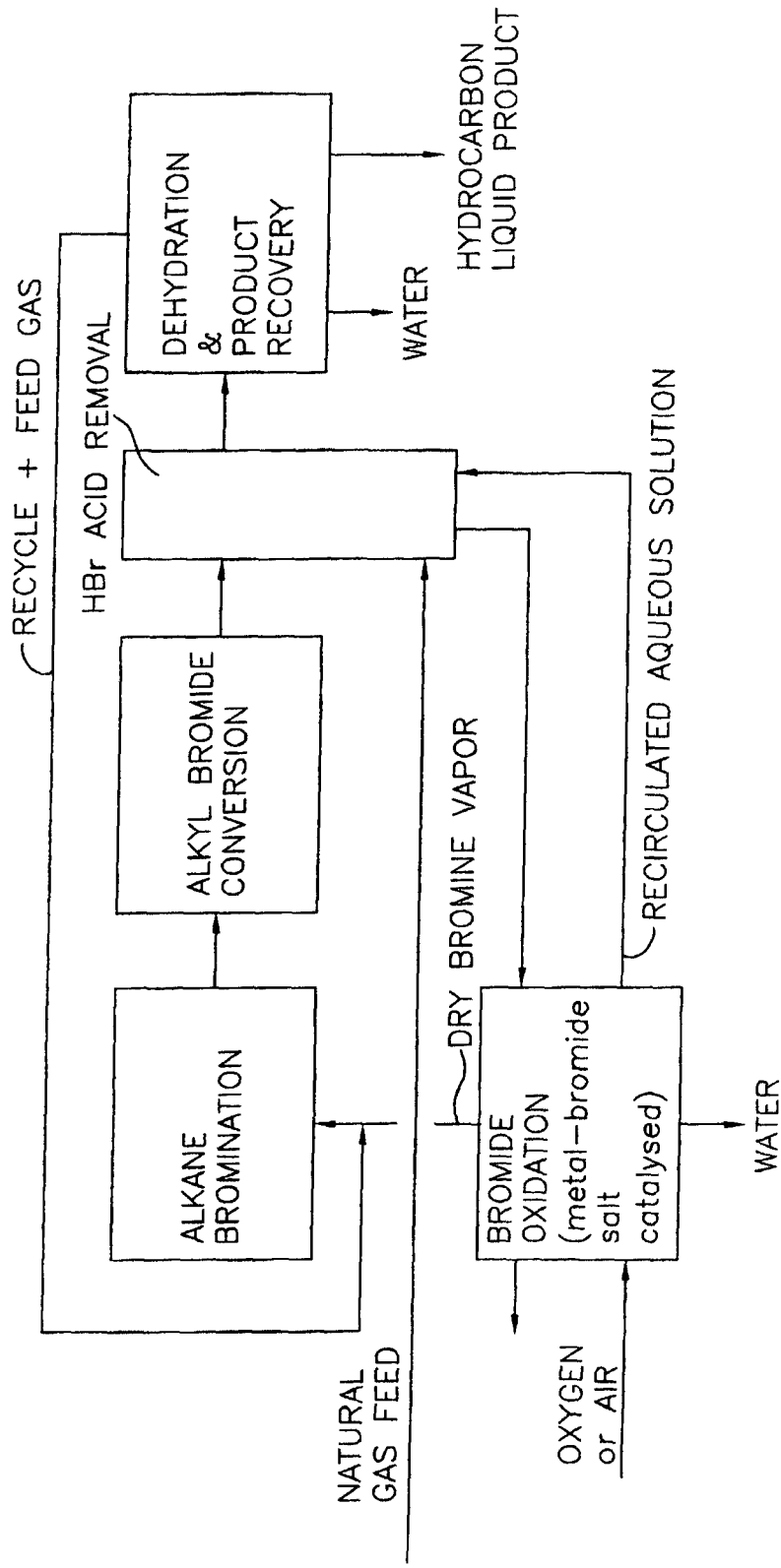
FIG. 1 is a simplified block flow diagram of an embodiment of the process of the present invention.

A block flow diagram generally depicting an embodiment of a process of the present invention is illustrated in FIG. 1, while specific embodiments of the process illustrated in FIG. 1 are illustrated in FIGS. 2 and 3. Referring to FIG. 1, a gas stream comprising recycle gas and a natural feed gas is combined with dry bromine vapor and fed to an alkane bromination reactor. The recycle gas and the natural gas feed may comprise lower molecular weight hydrocarbons. In the alkane bromination reactor, the gas stream and the dry bromine vapor are reacted to produce gaseous alkyl bromides and hydrobromic acid vapors. As illustrated, gaseous alkyl bromides and hydrobromic acid vapors are fed to the alkyl bromide conversion reactor. In the alkyl bromide conversion reactor, the gaseous alkyl bromides are reacted to form higher molecular weight hydrocarbons and additional hydrobromic acid vapors. In the illustrated embodiment, the hydrobromic acid vapors are then removed from the higher molecular hydrocarbons in the hydrobromic acid removal unit by a recirculated aqueous solution. As illustrated in FIG. 1, the recirculated aqueous solution carries the hydrobromic acid (or metal bromide salt if the acid is neutralized by the aqueous solution) to the bromide oxidation unit. As will be discussed in more detail below, the hydrobromic acid may be neutralized in the bromide oxidation unit to form a metal bromide salt. Oxygen or air is supplied to the bromide oxidation unit to oxidize the metal bromide salt to form the bromine, which is then recycled to the alkane bromination reactor.

In the illustrated embodiment, a natural gas feed is also introduced into the hydrobromic acid removal unit. From the hydrobromic acid removal unit, the natural gas feed and the higher molecular hydrocarbons are fed to the dehydration and product recovery unit. In the dehydration and product recovery unit, water is removed from the higher molecular weight hydrocarbons and a hydrocarbon liquid product is produced. In addition, a gas stream of recycle gas and the natural gas feed are conveyed to the alkane bromination reactor. Accordingly, the process illustrated in FIG. 1 may be used to produce a liquid hydrocarbon product from lower molecular hydrocarbons.

Referring to FIG. 2, a gas stream containing lower molecular weight alkanes, comprised of a mixture of a feed gas plus a recycled gas stream at a pressure in the range of about 1 bar to about 30 bar, is transported or conveyed via line, pipe or conduit 62, mixed with dry bromine liquid transported via line 25 and pump 24, and passed to heat exchanger 26 wherein the liquid bromine is vaporized. The mixture of lower molecular weight alkanes and dry bromine vapor is fed to reactor 30. Preferably, the molar ratio of lower molecular weight alkanes to dry bromine vapor in the mixture introduced into reactor 30 is in excess of 2.5:1. Reactor 30 has an inlet pre-heater zone 28 which heats the mixture to a reaction initiation temperature in the range of about 250° C. to about 400° C.

In first reactor 30, the lower molecular weight alkanes are reacted exothermically with dry bromine vapor at a relatively low temperature in the range of about 250° C. to about 600° C., and at a pressure in the range of about 1 bar to about 30 bar to produce gaseous alkyl bromides and hydrobromic acid vapors. The upper limit of the operating temperature range is greater than the upper limit of the reaction initiation temperature range to which the feed mixture is heated due to the exothermic nature of the bromination reaction. In the case of methane, the formation of methyl bromide occurs in accordance with the following general reaction:

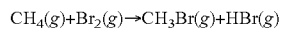

$$CH_4(g) + Br_2(g) \rightarrow CH_3Br(g) + HBr(g)$$

This reaction occurs with a significantly high degree of selectivity to methyl bromide. For example, in the case of bromination of methane, a methane to bromine ratio of about 4.5:1 increases the selectivity to the mono-halogenated methyl bromide to that obtained using smaller methane to bromine ratios. Small amounts of dibromomethane and tribromomethane are also formed in the bromination reaction. Higher alkanes, such as ethane, propane and butane, are also readily brominated resulting in mono and multiple brominated species such as ethyl bromides, propyl bromides and butyl bromides. If an alkane to bromine ratio of significantly less than about 2.5 to 1 is utilized, a lower selectivity to methyl bromide occurs and significant formation of undesirable carbon soot is observed. Further, the dry bromine vapor that is feed into first reactor 30 is substantially water-free. Applicant has discovered that elimination of substantially all water vapor from the bromination step in first reactor 30 substantially eliminates the formation of unwanted carbon dioxide thereby increasing the selectivity of alkane bromination to alkyl bromides and eliminating the large amount of waste heat generated in the formation of carbon dioxide from alkanes.

The effluent that contains alkyl bromides and hydrobromic acid is withdrawn from the first reactor via line 31 and is partially cooled in heat exchanger 32 before flowing to a second reactor 34. The temperature to which the effluent is partially cooled in heat exchanger 34 is in the range of about 150° C. to about 350° C. when it is desired to convert the alkyl bromides to higher molecular weight hydrocarbons in second reactor 34, or to range of about 150° C. to about 450° C. when it is desired to convert the alkyl bromides to olefins a second reactor 34. In second reactor 34, the alkyl bromides are reacted exothermically over a fixed bed 33 of crystalline alumino-silicate catalyst, preferably a zeolite catalyst. The temperature and pressure employed in second reactor, as well as the zeolite catalyst, will determine the product(s) that is formed from the reaction of alkyl bromides occurring in second reactor 34.

The crystalline alumino-silicate catalyst employed in second reactor 34 is preferably a zeolite catalyst and most preferably a ZSM-5 zeolite catalyst when it is desired to form higher molecular weight hydrocarbons, Although the zeolite catalyst is preferably used in the hydrogen, sodium or magnesium form, the zeolite may also be modified by ion exchange with other alkali metal cations, such as Li, Na, K or Cs, with alkali-earth metal cations, such as Mg, Ca, Sr or Ba, or with transition metal cations, such as Ni, Mn, V, W, or to the hydrogen form. Other zeolite catalysts having varying pore sizes and acidities, which are synthesized by varying the alumina-to-silica ratio may be used in the second reactor 34 as will be evident to a skilled artisan.

When it is desired to form olefins from the reaction of alkyl bromides in reactor 34, the crystalline alumino-silicate catalyst employed in second reactor 34 is preferably a zeolite catalyst, and most preferably an X type or Y type zeolite catalyst. A preferred zeolite is 10 X or Y type zeolite, although other zeolites with differing pore sizes and acidities, which are synthesized by varying the alumina-to-silica ratio may be used in the process of the present invention as will be evident to a skilled artisan. Although the zeolite catalyst is preferably used in a protonic form, a sodium form or a mixed protonic/sodium form, the zeolite may also be modified by ion exchange with other alkali metal cations, such as Li, K or Cs, with alkali-earth metal cations, such as Mg, Ca, Sr or Ba, or with transition metal cations, such as Ni, Mn, V, W, or to the hydrogen form. These various alternative cations have an effect of shifting reaction selectivity. Other zeolite catalysts having varying pore sizes and acidities, which are synthesized by varying the alumina-to-silica ratio may be used in the second reactor 34 as will be evident to a skilled artisan.

The temperature at which the second reactor 34 is operated is an important parameter in determining the selectivity of the reaction to higher molecular hydrocarbons or to olefins.

Where a catalyst is selected to form higher molecular weight hydrocarbons in reactor 34, it is preferred to operate second reactor 34 at a temperature within the range of about 150° to 450°. Temperatures above about 300° C. in the second reactor result in increased yields of light hydrocarbons, such as undesirable methane, whereas lower temperatures increase yields of heavier molecular weight hydrocarbon products. At the low end of the temperature range, with methyl bromide reacting over ZSM-5 zeolite at temperatures as low as 150° C. significant methyl bromide conversion on the order of 20% is noted, with a high selectivity towards $C_5+$ products. Notably, in the case of the alkyl bromide reaction over the preferred zeolite ZSM-5 catalyst, cyclization reactions also occur such that the C7+ fractions are composed primarily of substituted aromatics. At increasing temperatures approaching 300° C., methyl bromide conversion increases towards 90% or greater, however selectivity towards $C_5+$ products decreases and selectivity towards lighter products, particularly undesirable methane, increases. Surprisingly, very little ethane or $C_2$,-$C_3$ olefin components are formed. At temperatures approaching 450° C., almost complete conversion of methyl bromide to methane occurs. In the optimum operating temperature range of between about 300° C. and 400° C., as a byproduct of the reaction, a small amount of carbon will build up on the catalyst over time during operation, causing a decline in catalyst activity over a range of hours, up to hundreds of hours, depending on the reaction conditions and the composition of the feed gas. It is believed that higher reaction temperatures above about 400° C., associated with the formation of methane favor the thermal cracking of alkyl bromides and formation of carbon or coke and hence an increase in the rate of deactivation of the catalyst. Conversely, temperatures at the lower end of the range, particularly below about 300° C. may also contribute to coking due to a reduced rate of desorption of heavier products from the catalyst. Hence, operating temperatures within the range of about 150° C. to about 450° C., but preferably in the range of about 300° C. to about 400° C. in the second reactor 34 balance increased selectivity of the desired $C_5+$ products and lower rates of deactivation due to carbon formation, against higher conversion per pass, which minimizes the quantity of catalyst, recycle rates and equipment size required.

Where a catalyst is selected to form olefins in reactor 34, it is preferred to operate second reactor 34 at a temperature within the range of about 250° C. to 500° C. Temperatures above about 450° C. in the second reactor can result in increased yields of light hydrocarbons, such as undesirable methane and also deposition of coke, whereas lower temperatures increase yields of ethylene, propylene, butylene and heavier molecular weight hydrocarbon products. Notably, in the case of the alkyl bromide reaction over the preferred 10 X zeolite catalyst, it is believed that cyclization reactions also occur such that the C7+ fractions contain substantial substituted aromatics. At increasing temperatures approaching 400° C., it is believed that methyl bromide conversion increases towards 90% or greater, however selectivity towards $C_5+$ products decreases and selectivity towards lighter products, particularly olefins increases. At temperatures exceeding 550° C., it is believed that a high conversion of methyl bromide to methane and carbonaceous, coke occurs. In the preferred operating temperature range of between about 300° C. and 450° C., as a byproduct of the reaction, a lesser amount of coke probably will build up on the catalyst over time during operation, causing a decline in catalyst activity over a range of hours, up to hundreds of hours, depending on the reaction conditions and the composition of the feed gas. It is believed that higher reaction temperatures above about 400° C., associated with the formation of methane favor the thermal cracking of alkyl bromides and formation of carbon or coke and hence an increase in the rate of deactivation of the catalyst. Conversely, temperatures at the lower end of the range, particularly below about 300° C. may also contribute to coking due to a reduced rate of desorption of heavier products from the catalyst. Hence, operating temperatures within the range of about 250° C. to about 500° C., but preferably in the range of about 300° C. to about 450° C. in the second reactor 34 balance increased selectivity of the desired olefins and $C_5+$ products and lower rates of deactivation due to carbon formation, against higher conversion per pass, which minimizes the quantity of catalyst, recycle rates and equipment size required.

The catalyst may be periodically regenerated in situ, by isolating reactor 34 from the normal process flow, purging with an inert gas via line 70 at a pressure in a range from about 1 to about 5 bar at an elevated temperature in the range of about 400° C. to about 650° C. to remove unreacted material adsorbed on the catalyst insofar as is practical, and then subsequently oxidizing the deposited carbon to $CO_2$ by addition of air or inert gas-diluted oxygen to reactor 34 via line 70 at a pressure in the range of about 1 bar to about 5 bar at an elevated temperature in the range of about 400° C. to about 650° C. Carbon dioxide and residual air or inert gas is vented from reactor 34 via line 75 during the regeneration period.

The effluent which comprises hydrobromic acid and higher molecular weight hydrocarbons, olefins or mixtures thereof is withdrawn from the second reactor 34 via line 35 and is cooled to a temperature in the range of 0° C. to about 100° C. in exchanger 36 and combined with vapor effluent in line 12 from hydrocarbon stripper 47, which contains feed gas and residual higher molecular weight hydrocarbons stripped-out by contact with the feed gas in hydrocarbon stripper 47. The combined vapor mixture is passed to a scrubber 38 and contacted with a concentrated aqueous partially-oxidized metal bromide salt solution containing metal hydroxide, metal oxide, metal oxy-bromide or mixtures of these species, which is transported to scrubber 38 via line 41. The preferred metal of the bromide salt is Fe(III), Cu(II) or Zn(II), or mixtures thereof, as these are less expensive and readily oxidize at lower temperatures in the range of about 120° C. to about 180° C., allowing the use of glass-lined or fluorpolymer-lined equipment; although Co(II), Ni(II), Mn(II), V(II), Cr(II) or other transition-metals which form oxidizable bromide salts may be used in the process of the present invention. Alternatively, alkaline-earth metals which also form oxidizable bromide salts, such as Ca(II) or Mg(II) may be used. Any liquid hydrocarbons condensed in scrubber 38 may be skimmed and withdrawn in line 37 and added to liquid hydrocarbons exiting the product recovery unit 52 in line 54. Hydrobromic acid is dissolved in the aqueous solution and neutralized by the metal hydroxide, metal oxide, metal oxy-bromide or mixtures of these species to yield metal bromide salt in solution and water which is removed from the scrubber 38 via line 44.

The residual vapor phase containing olefins, higher molecular weight hydrocarbons or mixtures thereof that is removed as effluent from the scrubber 38 is forwarded via line 39 to dehydrator 50 to remove substantially all water via line 53 from the vapor stream. The water is then removed from the dehydrator 50 via line 53. The dried vapor stream containing olefins, higher molecular weight hydrocarbons or mixtures thereof is further passed via line 51 to product recovery unit 52 to recover olefins, the $C_5+$ gasoline-range hydrocarbon fraction or mixtures thereof as a liquid product in line 54. Any conventional method of dehydration and liquids recovery, such as solid-bed desiccant adsorption followed by refrigerated condensation, cryogenic expansion, or circulating absorption oil or other solvent, as used to process natural gas or refinery gas streams, and/or to recover olefinic hydrocarbons, as will be evident to a skilled artisan, may be employed in the process of the present invention. The residual vapor effluent from product recovery unit 52 is then split into a purge stream 57 which may be utilized as fuel for the process and a recycled residual vapor which is compressed via compressor 58. The recycled residual vapor discharged from compressor 58 is split into two fractions. A first fraction that is equal to at least 2.5 times the feed gas molar volume is transported via line 62 and is combined with dry liquid bromine conveyed by pump 24, heated in exchanger 26 to vaporize the bromine and fed into first reactor 30. The second fraction is drawn off of line 62 via line 63 and is regulated by control valve 60, at a rate sufficient to dilute the alkyl bromide concentration to reactor 34 and absorb the heat of reaction such that reactor 34 is maintained at the selected operating temperature, preferably in the range of about 300° C. to about 450° C. in order to maximize conversion versus selectivity and to minimize the rate of catalyst deactivation due to the deposition of carbon. Thus, the dilution provided by the recycled vapor effluent permits selectivity of bromination in the first reactor 30 to be controlled in addition to moderating the temperature in second reactor 34.

Water containing metal bromide salt in solution which is removed from scrubber 38 via line 44 is passed to hydrocarbon stripper 47 wherein residual dissolved hydrocarbons are stripped from the aqueous phase by contact with incoming feed gas transported via line 11. The stripped aqueous solution is transported from hydrocarbon stripper 47 via line 65 and is cooled to a temperature in the range of about 0° C. to about 70° C. in heat exchanger 46 and then passed to absorber 48 in which residual bromine is recovered from vent stream in line 67. The aqueous solution effluent from adsorber 48 is transported via line 49 to a heat exchanger 40 to be preheated to a temperature in the range of about 100° C. to about 600° C., and most preferably in the range of about 120° C. to about 180° C. and passed to third reactor 16. Oxygen or air is delivered via line 10 by blower or compressor 13 at a pressure in the range of about ambient to about 5 bar to bromine stripper 14 to strip residual bromine from water. Water is removed from stripper 14 in line 64 and combined with water stream 53 from dehydrator 50 to form water effluent stream in line 56 which is removed from the process. The oxygen or air leaving bromine stripper 14 is fed via line 15 to reactor 16 which operates at a pressure in the range of about ambient to about 5 bar and at a temperature in the range of about 100° C. to about 600° C., but most preferably in the range of about 120° C. to about 180° C. so as to oxidize an aqueous metal bromide salt solution to yield elemental bromine and metal hydroxide, metal oxide, metal oxy-bromide or mixtures of these species. As stated above, although Co(II), Ni(II), Mn(II), V(II), Cr(II) or other transition-metals which form oxidizable bromide salts can be used, the preferred metal of the bromide salt is Fe(III), Cu(II), or Zn(II), or mixtures thereof, as these are less expensive and readily oxidize at lower temperatures in the range of about 120° C. to about 180° C., which should allow the use of glass-lined or fluorpolymer-lined equipment. Alternatively, alkaline-earth metals which also form oxidizable bromide salts, such as Ca(II) or Mg(II) could be used.

Hydrobromic acid reacts with the metal hydroxide, metal oxide, metal oxy-bromide or mixtures of these species so formed to once again yield the metal bromide salt and water. Heat exchanger 18 in reactor 16 supplies heat to vaporize water and bromine. Thus, it is believed that the overall reactions result in the net oxidation of hydrobromic acid produced in first reactor 30 and second reactor 34 to elemental bromine and steam in the liquid phase catalyzed by the metal bromide/metal oxide or metal hydroxide operating in a catalytic cycle. In the case of the metal bromide being Fe(III)Br3, the reactions are believed to be:

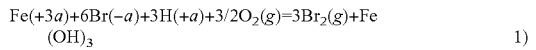

1)

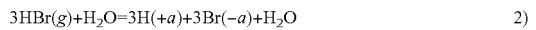

2)

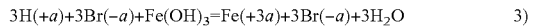

3)

In the case of the metal bromide being CU(II)Br2, the reactions are believed to be:

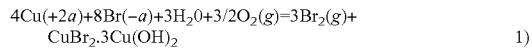

1)

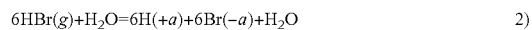

2)

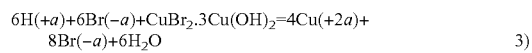

3)

The elemental bromine and water and any residual oxygen or nitrogen (if air is utilized as the oxidant) leaving as vapor from the outlet of third reactor 16 via line 19, are cooled in condenser 20 at a temperature in the range of about 0° C. to about 70° C. and a pressure in the range of about ambient to 5 bar to condense the bromine and water and passed to three-phase separator 22. In three-phase separator 22, since liquid water has a limited solubility for bromine, on the order of about 3% by weight, any additional bromine which is condensed forms a separate, denser liquid bromine phase. The liquid bromine phase, however, has a notably lower solubility for water, on the order of less than 0.1%. Thus a substantially dry bromine vapor can be easily obtained by condensing liquid bromine and water, decanting water by simple physical separation and subsequently re-vaporizing liquid bromine.

Liquid bromine is pumped in line 25 from three-phase separator 22 via pump 24 to a pressure sufficient to mix with vapor stream 62. Thus bromine is recovered and recycled within the process. The residual oxygen or nitrogen and any residual bromine vapor which is not condensed exits three-phase separator 22 and is passed via line 23 to bromine scrubber 48, wherein residual bromine is recovered by solution into and by reaction with reduced metal bromides in the aqueous metal bromide solution stream 65. Water is removed from separator 22 via line 27 and introduced into stripper 14.

In another embodiment of the invention, referring to FIG. 3, a gas stream containing lower molecular weight alkanes, comprised of mixture of a feed gas plus a recycled gas stream at a pressure in the range of about 1 bar to about 30 bar, is transported or conveyed via line, pipe or conduit 162, mixed with dry bromine liquid transported via pump 124 and passed to heat exchanger 126 wherein the liquid bromine is vaporized. The mixture of lower molecular weight alkanes and dry bromine vapor is fed to reactor 130. Preferably, the molar ratio of lower molecular weight alkanes to dry bromine vapor in the mixture introduced into reactor 130 is in excess of 2.5:1. Reactor 130 has an inlet pre-heater zone 128 which heats the mixture to a reaction initiation temperature in the range of about 250° C. to about 400° C. In first reactor 130, the lower molecular weight alkanes are reacted exothermically with dry bromine vapor at a relatively low temperature in the range of about 250° C. to about 600° C., and at a pressure in the range of about 1 bar to about 30 bar to produce gaseous alkyl bromides and hydrobromic acid vapors. The upper limit of the operating temperature range is greater than the upper limit of the reaction initiation temperature range to which the feed mixture is heated due to the exothermic nature of the bromination reaction. In the case of methane, the formation of methyl bromide occurs in accordance with the following general reaction:

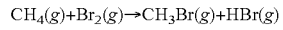

This reaction occurs with a significantly high degree of selectivity to methyl bromide. For example, in the case of bromination of methane, a methane to bromine ratio of about 4.5:1 increases the selectivity to the mono-halogenated methyl bromide. Small amounts of dibromomethane and tribromomethane are also formed in the bromination reaction.

Higher alkanes, such as ethane, propane and butane, are also readily brominated resulting in mono and multiple brominated species such as ethyl bromides, propyl bromides and butyl bromides. If an alkane to bromine ratio of significantly less than about 2.5 to 1 is utilized, a lower selectivity to methyl bromide occurs and significant formation of undesirable carbon soot is observed. Further, the dry bromine vapor that is feed into first reactor 30 is preferably substantially water-free. Applicant has discovered that elimination of substantially all water vapor from the bromination step in first reactor 30 substantially eliminates the formation of unwanted carbon dioxide thereby increasing the selectivity of alkane bromination to alkyl bromides and eliminating the large amount of waste heat generated in the formation of carbon dioxide from alkanes.

The effluent that contains alkyl bromides and hydrobromic acid is withdrawn from the first reactor via line 131 and is partially cooled in heat exchanger 132 before flowing to a second reactor 134. The temperature to which the effluent is partially cooled in heat exchanger 134 is in the range of about 150° C. to about 350° C. where it is desired to convert the alkyl bromides to higher molecular weight hydrocarbons in second reactor 134, or to range of about 150° C. to about 450° C. where it is desired to convert the alkyl bromides to olefins in second reactor 134. In second reactor 134, the alkyl bromides are reacted exothermically over a fixed bed 133 of crystalline alumino-silicate catalyst, preferably a zeolite catalyst. The temperature and pressure employed in second reactor 134, as well as the zeolite catalyst, will determine the product that is formed from the reaction of alkyl bromides occurring in second reactor 134.

The crystalline alumino-silicate catalyst employed in second reactor 134 is preferably a zeolite catalyst and most preferably a ZSM-5 zeolite catalyst when it is desired to form higher molecular weight hydrocarbons, Although the zeolite catalyst is preferably used in the hydrogen, sodium or magnesium form, the zeolite may also be modified by ion exchange with other alkali metal cations, such as Li, Na, K or Cs, with alkali-earth metal cations, such as Mg, Ca, Sr or Ba, or with transition metal cations, such as Ni, Mn, V, W, or to the hydrogen form. Other zeolite catalysts having varying pore sizes and acidities, which are synthesized by varying the alumina-to-silica ratio may be used in the second reactor 134 as will be evident to a skilled artisan.

When it is desired to form olefins from the reaction of alkyl bromides in reactor 134, the crystalline alumino-silicate catalyst employed in second reactor 134 is preferably a zeolite catalyst and most preferably an X type or Y type zeolite catalyst. A preferred zeolite is 10 X or Y type zeolite, although other zeolites with differing pore sizes and acidities, which are synthesized by varying the alumina-to-silica ratio may be used in the process of the present invention as will be evident to a skilled artisan. Although the zeolite catalyst is preferably used in a protonic form, a sodium form or a mixed protonic/sodium form, the zeolite may also be modified by ion exchange with other alkali metal cations, such as Li, K or Cs, with alkali-earth metal cations, such as Mg, Ca, Sr or Ba, or with transition metal cations, such as Ni, Mn, V, W, or to the hydrogen form. These various alternative cations have an effect of shifting reaction selectivity. Other zeolite catalysts having varying pore sizes and acidities, which are synthesized by varying the alumina-to-silica ratio may be used in the second reactor 134 as will be evident to a skilled artisan.

The temperature at which the second reactor 134 is operated is an important parameter in determining the selectivity of the reaction to higher molecular weight hydrocarbons or to olefins.

When a catalyst is selected to form higher molecular weight hydrocarbons in reactor 134, it is preferred to operate second reactor 134 at a temperature within the range of about 150° to 450°. Temperatures above about 300° C. in the second reactor result in increased yields of light hydrocarbons, such as undesirable methane, whereas lower temperatures increase yields of heavier molecular weight hydrocarbon products. At the low end of the temperature range, with methyl bromide reacting over ZSM-5 zeolite at temperatures as low as 150° C. significant methyl bromide conversion on the order of 20% is noted, with a high selectivity towards $C_5+$ products. Notably, in the case of the alkyl bromide reaction over the preferred zeolite ZSM-5 catalyst, cyclization reactions also occur such that the C7+ fractions are composed primarily of substituted aromatics. At increasing temperatures approaching 300° C., methyl bromide conversion increases towards 90% or greater, however selectivity towards $C_5+$ products decreases and selectivity towards lighter products, particularly undesirable methane, increases. Surprisingly, very little ethane or $C_2$,-$C_3$ olefin components are formed. At temperatures approaching 450° C., almost complete conversion of methyl bromide to methane occurs. In the optimum operating temperature range of between about 300° C. and 400° C., as a byproduct of the reaction, a small amount of carbon will build up on the catalyst over time during operation, causing a decline in catalyst activity over a range of hours, up to hundreds of hours, depending on the reaction conditions and the composition of the feed gas. It is believed that higher reaction temperatures above about 400° C., associated with the formation of methane favor the thermal cracking of alkyl bromides and formation of carbon or coke and hence an increase in the rate of deactivation of the catalyst. Conversely, temperatures at the lower end of the range, particularly below about 300° C. may also contribute to coking due to a reduced rate of desorption of heavier products from the catalyst. Hence, operating temperatures within the range of about 150° C. to about 450° C., but preferably in the range of about 300° C. to about 400° C. in the second reactor 134 balance increased selectivity of the desired $C_5+$ products and lower rates of deactivation due to carbon formation, against higher conversion per pass, which minimizes the quantity of catalyst, recycle rates and equipment size required.

When a catalyst is selected to form olefins in reactor 134, it is preferred to operate second reactor 134 at a temperature within the range of about 250° to 500° C. Temperatures above about 450° C. in the second reactor can result in increased yields of light hydrocarbons, such as undesirable methane and also deposition of coke, whereas lower temperatures increase yields of ethylene, propylene, butylene and heavier molecular weight hydrocarbon products. Notably, in the case of the alkyl bromide reaction over the preferred 10 X zeolite catalyst, it is believed that cyclization reactions also occur such that the C7+ fractions contain substantial substituted aromatics. At increasing temperatures approaching 400° C., it is believed that methyl bromide conversion increases towards 90% or greater, however selectivity towards $C_5+$ products decreases and selectivity towards lighter products, particularly olefins increases. At temperatures exceeding 550° C., it is believed that a high conversion of methyl bromide to methane and carbonaceous, coke occurs. In the preferred operating temperature range of between about 300° C. and 450° C., as a byproduct of the reaction, a lesser amount of coke probably will build up on the catalyst over time during operation, causing a decline in catalyst activity over a range of hours, up to hundreds of hours, depending on the reaction conditions and the composition of the feed gas. It is believed that higher reaction temperatures above about 400° C., associated with the formation of methane favor the thermal cracking of alkyl bromides and formation of carbon or coke and hence an increase in the rate of deactivation of the catalyst. Conversely, temperatures at the lower end of the range, particularly below about 300° C. may also contribute to coking due to a reduced rate of desorption of heavier products from the catalyst. Hence, operating temperatures within the range of about 250° C. to about 500° C., but preferably in the range of about 300° C. to about 450° C. in the second reactor 134 balance increased selectivity of the desired olefins and $C_5+$ products and lower rates of deactivation due to carbon formation, against higher conversion per pass, which minimizes the quantity of catalyst, recycle rates and equipment size required.

The catalyst may be periodically regenerated in situ, by isolating reactor 134 from the normal process flow, purging with an inert gas via line 170 at a pressure in the range of about 1 bar to about 5 bar and an elevated temperature in the range of 400° C. to 650° C. to remove unreacted material adsorbed on the catalyst insofar as is practical, and then subsequently oxidizing the deposited carbon to $CO_2$ by addition of air or inert gas-diluted oxygen via line 170 to reactor 134 at a pressure in the range of about 1 bar to about 5 bar and an elevated temperature in the range of 400° C. to 650° C. Carbon dioxide and residual air or inert gas are vented from reactor 134 via line 175 during the regeneration period.

The effluent which comprises hydrobromic acid and higher molecular weight hydrocarbons, olefins or mixtures thereof is withdrawn from the second reactor 134 via line 135, cooled to a temperature in the range of about 0° C. to about 100° C. in exchanger 136, and combined with vapor effluent in line 112 from hydrocarbon stripper 147. The mixture is then passed to a scrubber 138 and contacted with a stripped, recirculated water that is transported to scrubber 138 in line 164 by any suitable means, such as pump 143, and is cooled to a temperature in the range of about 0° C. to about 50° C. in heat exchanger 155. Any liquid hydrocarbon product condensed in scrubber 138 may be skimmed and withdrawn as stream 137 and added to liquid hydrocarbon product 154. Hydrobromic acid is dissolved in scrubber 138 in the aqueous solution which is removed from the scrubber 138 via line 144, and passed to hydrocarbon stripper 147 wherein residual hydrocarbons dissolved in the aqueous solution are stripped-out by contact with feed gas 111. The stripped aqueous phase effluent from hydrocarbon stripper 147 is cooled to a temperature in the range of about 0° C. to about 50° C. in heat exchanger 146 and then passed via line 165 to absorber 148 in which residual bromine is recovered from vent stream 167.

The residual vapor phase containing olefins, higher molecular weight hydrocarbons or mixtures thereof is removed as effluent from the scrubber 138 and forwarded to dehydrator 150 to remove substantially all water from the gas stream. The water is then removed from the dehydrator 150 via line 153. The dried gas stream containing olefins, higher molecular weight hydrocarbons or mixtures thereof is further passed via line 151 to product recovery unit 152 to recover olefins, the $C_5+$ gasoline range hydrocarbon fraction or mixtures thereof as a liquid product in line 154. Any conventional method of dehydration and liquids recovery such as solid-bed dessicant adsorption followed by, for example, refrigerated condensation, cryogenic expansion, or circulating absorption oil, or other solvents as used to process natural gas or refinery gas streams and recover olefinic hydrocarbons, as known to a skilled artisan, may be employed in the implementation of this invention. The residual vapor effluent from product recovery unit 152 is then split into a purge stream 157 that may be utilized as fuel for the process and a recycled residual vapor which is compressed via compressor 158. The recycled residual vapor discharged from compressor 158 is split into two fractions. A first fraction that is equal to at least 2.5 times the feed gas volume is transported via line 162, combined with the liquid bromine conveyed in line 125 and passed to heat exchanger 126 wherein the liquid bromine is vaporized and fed into first reactor 130. The second fraction which is drawn off line 162 via line 163 and is regulated by control valve 160, at a rate sufficient to dilute the alkyl bromide concentration to reactor 134 and absorb the heat of reaction such that reactor 134 is maintained at the selected operating temperature, preferably in the range of about 300° C. to about 450° C. in order to maximize conversion vs. selectivity and to minimize the rate of catalyst deactivation due to the deposition of carbon. Thus, the dilution provided by the recycled vapor effluent permits selectivity of bromination in the first reactor 130 to be controlled in addition to moderating the temperature in second reactor 134.

Oxygen, oxygen enriched air or air 110 is delivered via blower or compressor 113 at a pressure in the range of about ambient to about 5 bar to bromine stripper 114 to strip residual bromine from water which leaves stripper 114 via line 164 and is divided into two portions. The first portion of the stripped water is recycled via line 164, cooled in heat exchanger 155 to a temperature in the range of about 20° C. to about 50° C., and maintained at a pressure sufficient to enter scrubber 138 by any suitable means, such as pump 143. The portion of water that is recycled is selected such that the hydrobromic acid solution effluent removed from scrubber 138 via line 144 has a concentration in the range from about 10% to about 50% by weight hydrobromic acid, but more preferably in the range of about 30% to about 48% by weight to minimize the amount of water which must be vaporized in exchanger 141 and preheater 119 and to minimize the vapor pressure of HBr over the resulting acid. A second portion of water from stripper 114 is removed from line 164 and the process via line 156.

The dissolved hydrobromic acid that is contained in the aqueous solution effluent from adsorber 148 is transported via line 149 and is combined with the oxygen, oxygen enriched air or air leaving bromine stripper 114 in line 115. The combined aqueous solution effluent and oxygen, oxygen enriched air or air is passed to a first side of heat exchanger 141 and through preheater 119 wherein the mixture is preheated to a temperature in the range of about 100° C. to about 600° C. and most preferably in the range of about 120° C. to about 250° C. and passed to third reactor 117 that contains a metal bromide salt or metal oxide. The preferred metal of the bromide salt or metal oxide is Fe(III), Cu(II) or Zn(II) although Co(II), Ni(II), Mn(II), V(II), Cr(II) or other transition-metals which form oxidizable bromide salts can be used. Alternatively, alkaline-earth metals which also form oxidizable bromide salts, such as Ca (II) or Mg(II) could be used. The metal bromide salt in the oxidation reactor 117 can be utilized as a concentrated aqueous solution or preferably, the concentrated aqueous salt solution may be imbibed into a porous, high surface area, acid resistant inert support such as a silica gel. More preferably, the oxide form of the metal in a range of 10 to 20% by weight is deposited on an inert support such as alumina with a specific surface area in the range of 50 to 200 m2/g. The oxidation reactor 117 operates at a pressure in the range of about ambient to about 5 bar and at a temperature in the range of about 100° C. to about 600° C., but most preferably in the range of about 130° C. to 350° C.; therein, the metal bromide is oxidized by oxygen, yielding elemental bromine and metal hydroxide, metal oxide or metal oxy-bromide species or, metal oxides in the case of the supported metal bromide salt or metal oxide operated at higher temperatures and lower pressures at which water may primarily exist as a vapor. In either case, the hydrobromic acid reacts with the metal hydroxide, metal oxy-bromide or metal oxide species and is neutralized, restoring the metal bromide salt and yielding water. Thus, it is believed that the overall reaction results in the net oxidation of hydrobromic acid produced in first reactor 130 and second reactor 134 to elemental bromine and steam, catalyzed by the metal bromide/metal hydroxide or metal oxide operating in a catalytic cycle. In the case of the metal bromide being Fe(III)Br2 in an aqueous solution and operated in a pressure and temperature range in which water may exist as a liquid the reactions are believed to be:

$$Fe(+3a)+6Br(-a)+3H(+a)+3/2O_2(g)=3Br_2(g)+Fe(OH)3 \quad 1)$$

$$3HBr(g)+H_2O=3H(+a)+3Br(-a)+H_2O \quad 2)$$

$$3H(+a)+3Br(-a)+Fe(OH)3=Fe(+3a)+3Br(-a)+3H_2O \quad 3)$$

In the case of the metal bromide being CU(II)Br2, in an aqueous solution and operated in a pressure and temperature range in which water may exist as a liquid the reactions are believed to be:

$$4Cu(+2a)+8Br(-a)+3H_2O+3/2O_2(g)=3Br_2(g)+CuBr_2.3Cu(OH)_2 \quad 1)$$

$$6HBr(g)+H_2O=6H(+a)+6Br(-a)+H_2O \quad 2)$$

$$6H(+a)+6Br(-a)+CuBr_2.3Cu(OH)_2=4Cu(+2a)+8Br(-a)+6H_2O \quad 3)$$

In the case of the metal bromide being Cu(II)Br2 supported on an inert support and operated at higher temperature and lower pressure conditions at which water primarily exists as a vapor, the reactions are believed to be:

$$2Cu(II)Br2=2Cu(I)Br+Br_2(g) \quad 1)$$

$$2Cu(I)Br+O_2(g)=Br2(g)+2Cu(II)O \quad 2)$$

$$2HBr(g)+Cu(II)O=Cu(II)Br_2+H_2O(g) \quad 3)$$

The elemental bromine and water and any residual oxygen or nitrogen (if air or oxygen enriched air is utilized as the oxidant) leaving as vapor from the outlet of third reactor 117, are cooled in the second side of exchanger 141 and condenser 120 to a temperature in the range of about 0° C. to about 70° C. wherein the bromine and water are condensed and passed to three-phase separator 122. In three-phase separator 122, since liquid water has a limited solubility for bromine, on the order of about 3% by weight, any additional bromine which is condensed forms a separate, denser liquid bromine phase. The liquid bromine phase, however, has a notably lower solubility for water, on the order of less than 0.1%. Thus, a substantially dry bromine vapor can be easily obtained by condensing liquid bromine and water, decanting water by simple physical separation and subsequently re-vaporizing liquid bromine. It is important to operate at conditions that result in the near complete reaction of HBr so as to avoid significant residual HBr in the condensed liquid bromine and water, as HBr increases the miscibility of bromine in the aqueous phase, and at sufficiently high concentrations, results in a single ternary liquid phase.

Liquid bromine is pumped from three-phase separator 122 via pump 124 to a pressure sufficient to mix with vapor stream 162. Thus the bromine is recovered and recycled within the process. The residual air, oxygen enriched air or oxygen and any bromine vapor which is not condensed exits three-phase separator 122 and is passed via line 123 to bromine scrubber 148, wherein residual bromine is recovered by dissolution into hydrobromic acid solution stream conveyed to scrubber 148 via line 165. Water is removed from the three-phase separator 122 via line 129 and passed to stripper 114.

The elemental bromine vapor and steam are condensed and easily separated in the liquid phase by simple physical separation, yielding substantially dry bromine. The absence of significant water allows selective bromination of alkanes, without production of $CO_2$ and the subsequent efficient and selective reactions of alkyl bromides to primarily $C_2$ to $C_4$ olefins, heavier products, the $C_5$+ fraction of which contains substantial branched alkanes and substituted aromatics, or mixtures thereof. Byproduct hydrobromic acid vapor from the bromination reaction and subsequent reaction in reactor 134 are readily dissolved into an aqueous phase and neutralized by the metal hydroxide or metal oxide species resulting from oxidation of the metal bromide.

Figure 4A:
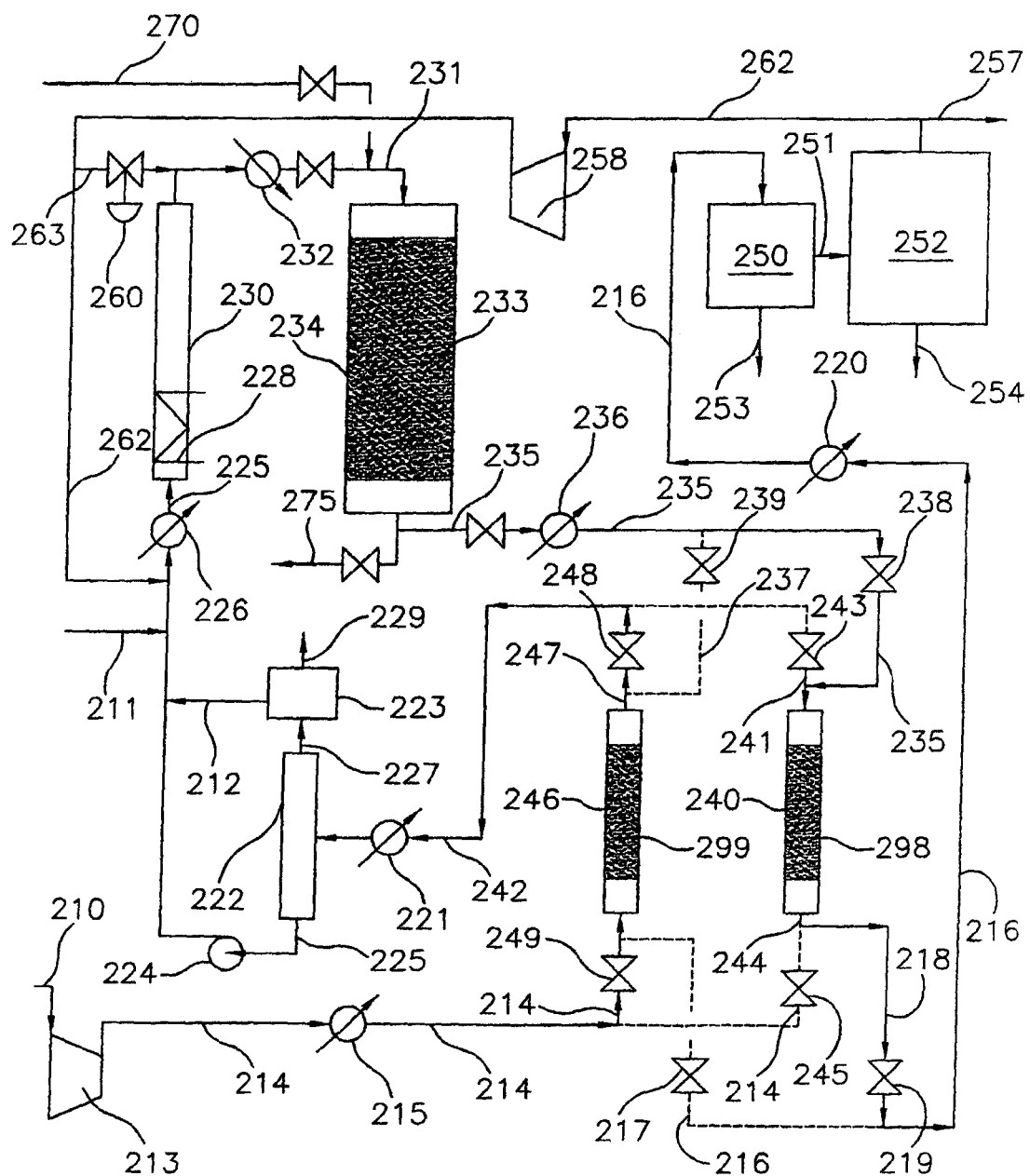
FIG. 4A is schematic view of another embodiment of the process of the present invention.

In accordance with another embodiment of the process of the present invention illustrated in FIG. 4A, the alkyl bromination and alkyl bromide conversion stages are operated in a substantially similar manner to those corresponding stages described with respect to FIGS. 2 and 3 above. More particularly, a gas stream containing lower molecular weight alkanes, comprised of mixture of a feed gas and a recycled gas stream at a pressure in the range of about 1 bar to about 30 bar, is transported or conveyed via line, pipe or conduits 262 and 211, respectively, and mixed with dry bromine liquid in line 225. The resultant mixture is transported via pump 224 and passed to heat exchanger 226 wherein the liquid bromine is vaporized. The mixture of lower molecular weight alkanes and dry bromine vapor is fed to reactor 230. Preferably, the molar ratio of lower molecular weight alkanes to dry bromine vapor in the mixture introduced into reactor 230 is in excess of 2.5:1. Reactor 230 has an inlet pre-heater zone 228 which heats the mixture to a reaction initiation temperature in the range of 250° C. to 400° C. In first reactor 230, the lower molecular weight alkanes are reacted exothermically with dry bromine vapor at a relatively low temperature in the range of about 250° C. to about 600° C., and at a pressure in the range of about 1 bar to about 30 bar to produce gaseous alkyl bromides and hydrobromic acid vapors. The upper limit of the operating temperature range is greater than the upper limit of the reaction initiation temperature range to which the feed mixture is heated due to the exothermic nature of the bromination reaction. In the case of methane, the formation of methyl bromide occurs in accordance with the following general reaction:

$$CH_4(g)+Br_2(g) \rightarrow CH_3Br(g)+HBr(g)$$

This reaction occurs with a significantly high degree of selectivity to methyl bromide. For example, in the case of bromine reacting with a molar excess of methane at a methane to bromine ratio of 4.5:1, a high selectivity to the mono-halogenated methyl bromide occurs. Small amounts of dibromomethane and tribromomethane are also formed in the bromination reaction. Higher alkanes, such as ethane, propane and butane, are also readily brominated resulting in mono and multiple brominated species such as ethyl bromides, propyl bromides and butyl bromides. If an alkane to bromine ratio of significantly less than 2.5 to 1 is utilized, substantially lower selectivity to methyl bromide occurs and significant formation of undesirable carbon soot is observed. Further, the dry bromine vapor that is feed into first reactor 230 is substantially water-free. Applicant has discovered that elimination of substantially all water vapor from the bromination step in first reactor 230 substantially eliminates the formation of unwanted carbon dioxide thereby increasing the selectivity of alkane bromination to alkyl bromides and eliminating the large amount of waste heat generated in the formation of carbon dioxide from alkanes.

The effluent that contains alkyl bromides and hydrobromic acid is withdrawn from the first reactor via line 231 and is partially cooled in heat exchanger 232 before flowing to a second reactor 234. The temperature to which the effluent is partially cooled in heat exchanger 234 is in the range of about 150° C. to about 350° C. when it is desired to convert the alkyl bromides to higher molecular weight hydrocarbons in second reactor 234, or to range of about 150° C. to about 450° C. when it is desired to convert the alkyl bromides to olefins a second reactor 234. In second reactor 234, the alkyl bromides are reacted exothermically over a fixed bed 233 of crystalline alumino-silicate catalyst, preferably a zeolite catalyst. The temperature and pressure employed in second reactor, as well as the zeolite catalyst, will determine the product that is formed from the reaction of alkyl bromides occurring in second reactor 234.

The crystalline alumino-silicate catalyst employed in second reactor 234 is preferably a zeolite catalyst and most preferably a ZSM-5 zeolite catalyst when it is desired to form higher molecular weight hydrocarbons, Although the zeolite catalyst is preferably used in the hydrogen, sodium or magnesium form, the zeolite may also be modified by ion exchange with other alkali metal cations, such as Li, Na, K or Cs, with alkali-earth metal cations, such as Mg, Ca, Sr or Ba, or with transition metal cations, such as Ni, Mn, V, W, or to the hydrogen form. Other zeolite catalysts having varying pore sizes and acidities, which are synthesized by varying the alumina-to-silica ratio may be used in the second reactor 234 as will be evident to a skilled artisan.

When it is desired to form olefins from the reaction of alkyl bromides in reactor 234, the crystalline alumino-silicate catalyst employed in second reactor 234 is preferably a zeolite catalyst, and most preferably an X type or Y type zeolite catalyst. A preferred zeolite is 10 X or Y type zeolite, although other zeolites with differing pore sizes and acidities, which are synthesized by varying the alumina-to-silica ratio may be used in the process of the present invention as will be evident to a skilled artisan. Although the zeolite catalyst is preferably used in a protonic form, a sodium form or a mixed protonic/sodium form, the zeolite may also be modified by ion exchange with other alkali metal cations, such as Li, K or Cs, with alkali-earth metal cations, such as Mg, Ca, Sr or Ba, or with transition metal cations, such as Ni, Mn, V, W, or to the hydrogen form. These various alternative cations have an effect of shifting reaction selectivity. Other zeolite catalysts having varying pore sizes and acidities, which are synthesized by varying the alumina-to-silica ratio may be used in the second reactor 234 as will be evident to a skilled artisan.

The temperature at which the second reactor 234 is operated is an important parameter in determining the selectivity of the reaction to higher molecular hydrocarbons, or to olefins.

Where a catalyst is selected to form higher molecular weight hydrocarbons in reactor 234, it is preferred to operate second reactor 234 at a temperature within the range of about 150° to 450°. Temperatures above about 300° C. in the second reactor result in increased yields of light hydrocarbons, such as undesirable methane, whereas lower temperatures increase yields of heavier molecular weight hydrocarbon products. At the low end of the temperature range, with methyl bromide reacting over ZSM-5 zeolite at temperatures as low as 150° C. significant methyl bromide conversion on the order of 20% is noted, with a high selectivity towards $C_5+$ products. Notably, in the case of the alkyl bromide reaction over the preferred zeolite ZSM-5 catalyst, cyclization reactions also occur such that the C7+ fractions are composed primarily of substituted aromatics. At increasing temperatures approaching 300° C., methyl bromide conversion increases towards 90% or greater, however selectivity towards $C_5+$ products decreases and selectivity towards lighter products, particularly undesirable methane, increases. Surprisingly, very little ethane or $C_2$,-$C_3$ olefin components are formed. At temperatures approaching 450° C., almost complete conversion of methyl bromide to methane occurs. In the optimum operating temperature range of between about 300° C. and 400° C., as a byproduct of the reaction, a small amount of carbon will build up on the catalyst over time during operation, causing a decline in catalyst activity over a range of hours, up to hundreds of hours, depending on the reaction conditions and the composition of the feed gas. It is believed that higher reaction temperatures above about 400° C., associated with the formation of methane favor the thermal cracking of alkyl bromides and formation of carbon or coke and hence an increase in the rate of deactivation of the catalyst. Conversely, temperatures at the lower end of the range, particularly below about 300° C. may also contribute to coking due to a reduced rate of desorption of heavier products from the catalyst. Hence, operating temperatures within the range of about 150° C. to about 450° C., but preferably in the range of about 300° C. to about 400° C. in the second reactor 234 balance increased selectivity of the desired $C_5+$ products and lower rates of deactivation due to carbon formation, against higher conversion per pass, which minimizes the quantity of catalyst, recycle rates and equipment size required.

Where a catalyst is selected to form olefins in reactor 234, it is preferred to operated second reactor 234 at a temperature within the range of about 250° to 500° C. Temperatures above about 450° C. in the second reactor can result in increased yields of light hydrocarbons, such as undesirable methane and also deposition of coke, whereas lower temperatures increase yields of ethylene, propylene, butylene and heavier molecular weight hydrocarbon products. Notably, in the case of the alkyl bromide reaction over the preferred 10 X zeolite catalyst, it is believed that cyclization reactions also occur such that the C7+ fractions contain substantial substituted aromatics. At increasing temperatures approaching 400° C., it is believed that methyl bromide conversion increases towards 90% or greater, however selectivity towards $C_5+$ products decreases and selectivity towards lighter products, particularly olefins increases. At temperatures exceeding 550° C., it is believed that a high conversion of methyl bromide to methane and carbonaceous, coke occurs. In the preferred operating temperature range of between about 300° C. and 450° C., as a byproduct of the reaction, a lesser amount of coke probably will build up on the catalyst over time during operation, causing a decline in catalyst activity over a range of hours, up to hundreds of hours, depending on the reaction conditions and the composition of the feed gas. It is believed that higher reaction temperatures above about 400° C., associated with the formation of methane favor the thermal cracking of alkyl bromides and formation of carbon or coke and hence an increase in the rate of deactivation of the catalyst. Conversely, temperatures at the lower end of the range, particularly below about 300° C. may also contribute to coking due to a reduced rate of desorption of heavier products from the catalyst. Hence, operating temperatures within the range of about 250° C. to about 500° C., but preferably in the range of about 300° C. to about 450° C. in the second reactor 234 balance increased selectivity of the desired olefins and $C_5+$ products and lower rates of deactivation due to carbon formation, against higher conversion per pass, which minimizes the quantity of catalyst, recycle rates and equipment size required.

The catalyst may be periodically regenerated in situ, by isolating reactor 234 from the normal process flow, purging with an inert gas via line 270 at a pressure in the range of about 1 bar to about 5 bar and an elevated temperature in the range of about 400° C. to about 650° C. to remove unreacted material adsorbed on the catalyst insofar as is practical, and then subsequently oxidizing the deposited carbon to $CO_2$ by addition of air or inert gas-diluted oxygen via line 270 to reactor 234 at a pressure in the range of about 1 bar to about 5 bar and an elevated temperature in the range of about 400° C. to about 650° C. Carbon dioxide and residual air or inert gas are vented from reactor 234 via line 275 during the regeneration period.

The effluent which comprises hydrobromic acid and higher molecular weight hydrocarbons, olefins or mixtures thereof is withdrawn from the second reactor 234 via line 235 and cooled to a temperature in the range of about 100° C. to about 600° C. in exchanger 236. As illustrated in FIG. 4A, the cooled effluent is transported via lines 235 and 241 with valve 238 in the opened position and valves 239 and 243 in the closed position and introduced into a vessel or reactor 240 containing a bed 298 of a solid phase metal oxide. The metal of the metal oxide is selected form magnesium (Mg), calcium (Ca), vanadium (V), chromium (Cr), manganese (Mn), iron (Fe), cobalt (Co), nickel (Ni), copper (Cu), zinc (Sn), or tin (Sn). The metal is selected for the impact of its physical and thermodynamic properties relative to the desired temperature of operation, and also for potential environmental and health impacts and cost. Preferably, magnesium, copper and iron are employed as the metal, with magnesium being the most preferred. These metals have the property of not only forming oxides but bromide salts as well, with the reactions being reversible in a temperature range of less than about 500° C. The solid metal oxide is preferably immobilized on a suitable attrition-resistant support, for example a synthetic amorphous silica, such as Davicat Grade 57, manufactured by Davison Catalysts of Columbia, Md. Or more preferably, an alumina support with a specific surface area of about 50 to 200 m2/g. In reactor 240, hydrobromic acid is reacted with the metal oxide at temperatures below about 600° C. and preferably between about 100° C. to about 500° C. in accordance with the following general formula wherein M represents the metal:

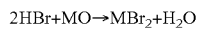

$$2HBr + MO \rightarrow MBr_2 + H_2O$$

The steam resulting from this reaction is transported together with olefins and/or the high molecular hydrocarbons in line 244, 218 and 216 via opened valve 219 to heat exchanger 220 wherein the mixture is cooled to a temperature in the range of about 0° C. to about 70° C. This cooled mixture is forwarded to dehydrator 250 to remove substantially all water from the gas stream. The water is then removed from the dehydrator 250 via line 253. The dried gas stream containing olefins, higher molecular weight hydrocarbons or mixtures thereof is further passed via line 251 to product recovery unit 252 to recover olefins, the $C_5+$ fraction, or mixtures thereof as a liquid product in line 254. Any conventional method of dehydration and liquids recovery such as solid-bed dessicant adsorption followed by, for example, refrigerated condensation, cryogenic expansion, or circulating absorption oil or other solvent, as used to process natural gas or refinery gas streams and recover olefinic hydrocarbons, as known to a skilled artisan, may be employed in the implementation of this invention. The residual vapor effluent from product recovery unit 252 is then split into a purge stream 257 that may be utilized as fuel for the process and a recycled residual vapor which is compressed via compressor 258. The recycled residual vapor discharged from compressor 258 is split into two fractions. A first fraction that is equal to at least 1.5 times the feed gas volume is transported via line 262, combined with the liquid bromine and feed gas conveyed in line 225 and passed to heat exchanger 226 wherein the liquid bromine is vaporized and fed into first reactor 230 in a manner as described above. The second fraction which is drawn off line 262 via line 263 and is regulated by control valve 260, at a rate sufficient to dilute the alkyl bromide concentration to reactor 234 and absorb the heat of reaction such that reactor 234 is maintained at the selected operating temperature, preferably in the range of about 300° C. to about 450° C. in order to maximize conversion vs. selectivity and to minimize the rate of catalyst deactivation due to the deposition of carbon. Thus, the dilution provided by the recycled vapor effluent permits selectivity of bromination in the first reactor 230 to be controlled in addition to moderating the temperature in second reactor 234.

Oxygen, oxygen enriched air or air 210 is delivered via blower or compressor 213 at a pressure in the range of about ambient to about 10 bar to bromine via line 214, line 215 and valve 249 through heat exchanger 215, wherein oxygen, oxygen enriched air or air is preheated to a temperature in the range of about 100° C. to about 500° C. to a second vessel or reactor 246 containing a bed 299 of a solid phase metal bromide. Oxygen reacts with the metal bromide in accordance with the following general reaction wherein M represents the metal:

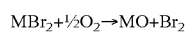

$$MBr_2 + \tfrac{1}{2}O_2 \rightarrow MO + Br_2$$

In this manner, a dry, substantially HBr free bromine vapor is produced thereby eliminating the need for subsequent separation of water or hydrobromic acid from the liquid bromine. Reactor 246 is operated below 600° C., and more preferably between about 300° C. to about 500° C. The resultant bromine vapor is transported from reactor 246 via line 247, valve 248 and line 242 to heat exchanger or condenser 221 where the bromine is condensed into a liquid. The liquid bromine is transported via line 242 to separator 222 wherein liquid bromine is removed via line 225 and transported via line 225 to heat exchanger 226 and first reactor 230 by any suitable means, such as by pump 224. The residual air or unreacted oxygen is transported from separator 222 via line 227 to a bromine scrubbing unit 223, such as venturi scrubbing system containing a suitable solvent, or suitable solid adsorbant medium, as selected by a skilled artisan, wherein the remaining bromine is captured. The captured bromine is desorbed from the scrubbing solvent or adsorbant by heating or other suitable means and the thus recovered bromine transported via line 212 to line 225. The scrubbed air or oxygen is vented via line 229. In this manner, nitrogen and any other substantially non-reactive components are removed from the system of the present invention and thereby not permitted to enter the hydrocarbon-containing portion of the process; also loss of bromine to the surrounding environment is avoided.

One advantage of removing the HBr by chemical reaction in accordance with this embodiment, rather than by simple physical solubility, is the substantially complete scavenging of the HBr to low levels at higher process temperatures. Another distinct advantage is the elimination of water from the bromine removed thereby eliminating the need for separation of bromine and water phases and for stripping of residual bromine from the water phase.

Figure 5A:
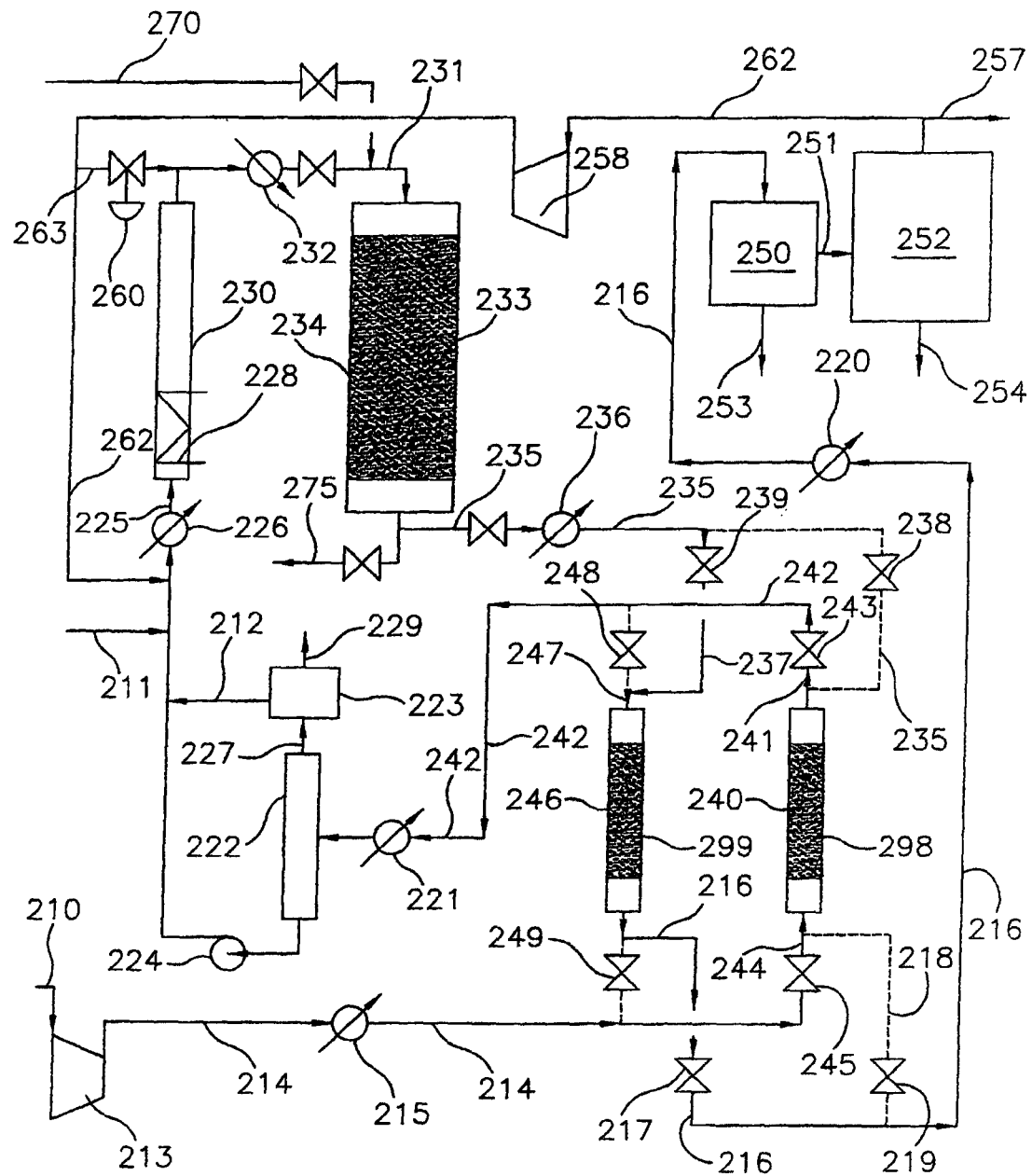
FIG. 5A is a schematic view of the embodiment of the process of the present invention illustrated in FIG. 4A with the flow through the metal oxide beds being reversed.

Reactors 240 and 246 may be operated in a cyclic fashion. As illustrated in FIG. 4A, valves 238 and 219 are operated in the open mode to permit hydrobromic acid to be removed from the effluent that is withdrawn from the second reactor 234, while valves 248 and 249 are operated in the open mode to permit air, oxygen enriched air or oxygen to flow through reactor 246 to oxidize the solid metal bromide contained therein. Once significant conversion of the metal oxide and metal bromide in reactors 240 and 246, respectively, has occurred, these valves are closed. At this point, bed 299 in reactor 246 is a bed of substantially solid metal bromide, while bed 298 in reactor 240 is substantially solid metal oxide. As illustrated in FIG. 5A, valves 245 and 243 are then opened to permit oxygen, oxygen enriched air or air to flow through reactor 240 to oxidize the solid metal bromide contained therein, while valves 239 and 217 are opened to permit effluent which comprises olefins, the higher molecular weight hydrocarbons and/or hydrobromic acid that is withdrawn from the second reactor 234 to be introduced into reactor 246. The reactors are operated in this manner until significant conversion of the metal oxide and metal bromide in reactors 246 and 240, respectively, has occurred and then the reactors are cycled back to the flow schematic illustrated in FIG. 4A by opening and closing valves as previously discussed.

Figure 4B:
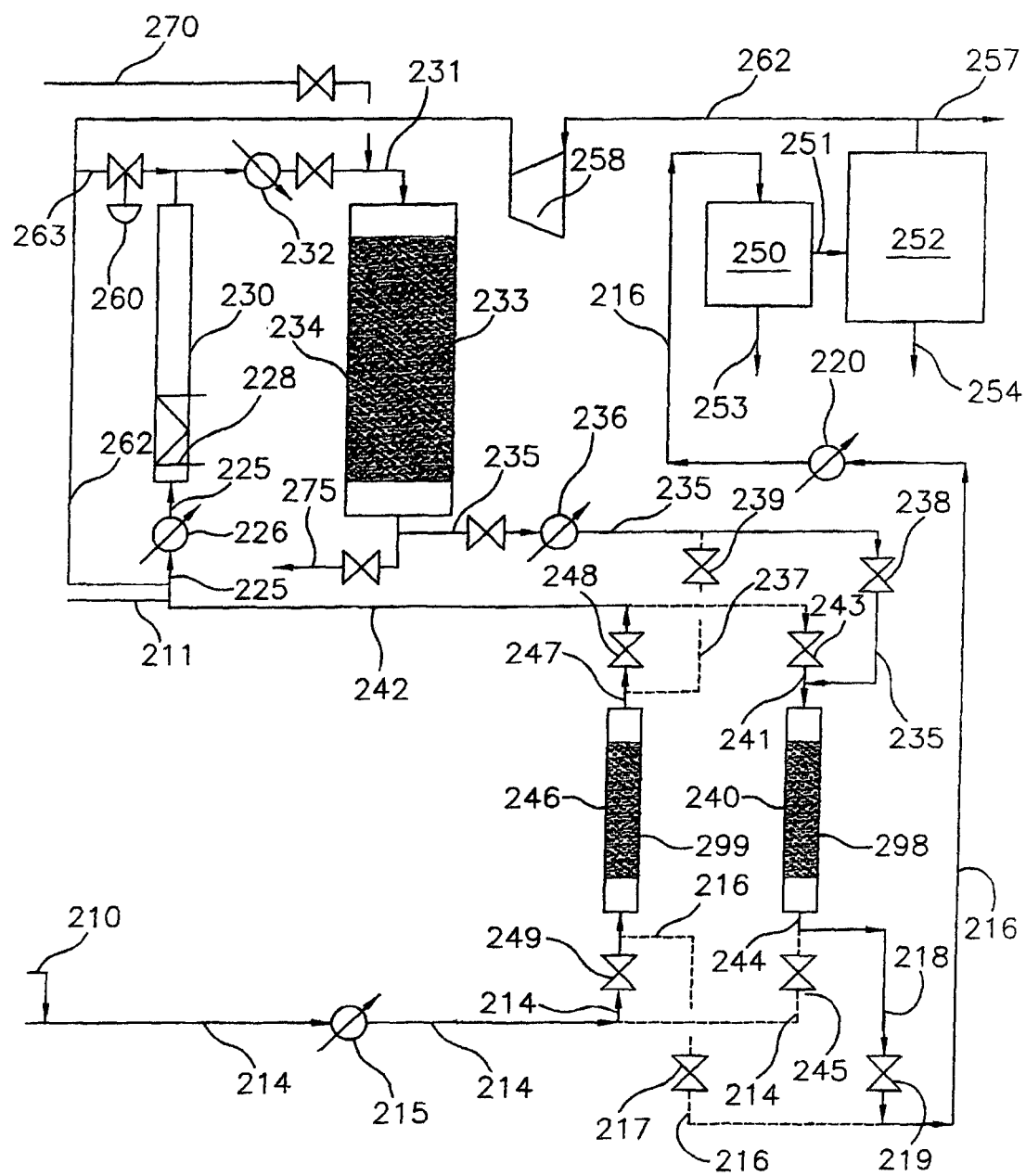
FIG. 4B is a schematic view of the embodiment of the process of the present invention illustrated in FIG. 4A depicting an alternative processing scheme which may be employed when oxygen is used in lieu of air in the oxidation stage.
Figure 5B:
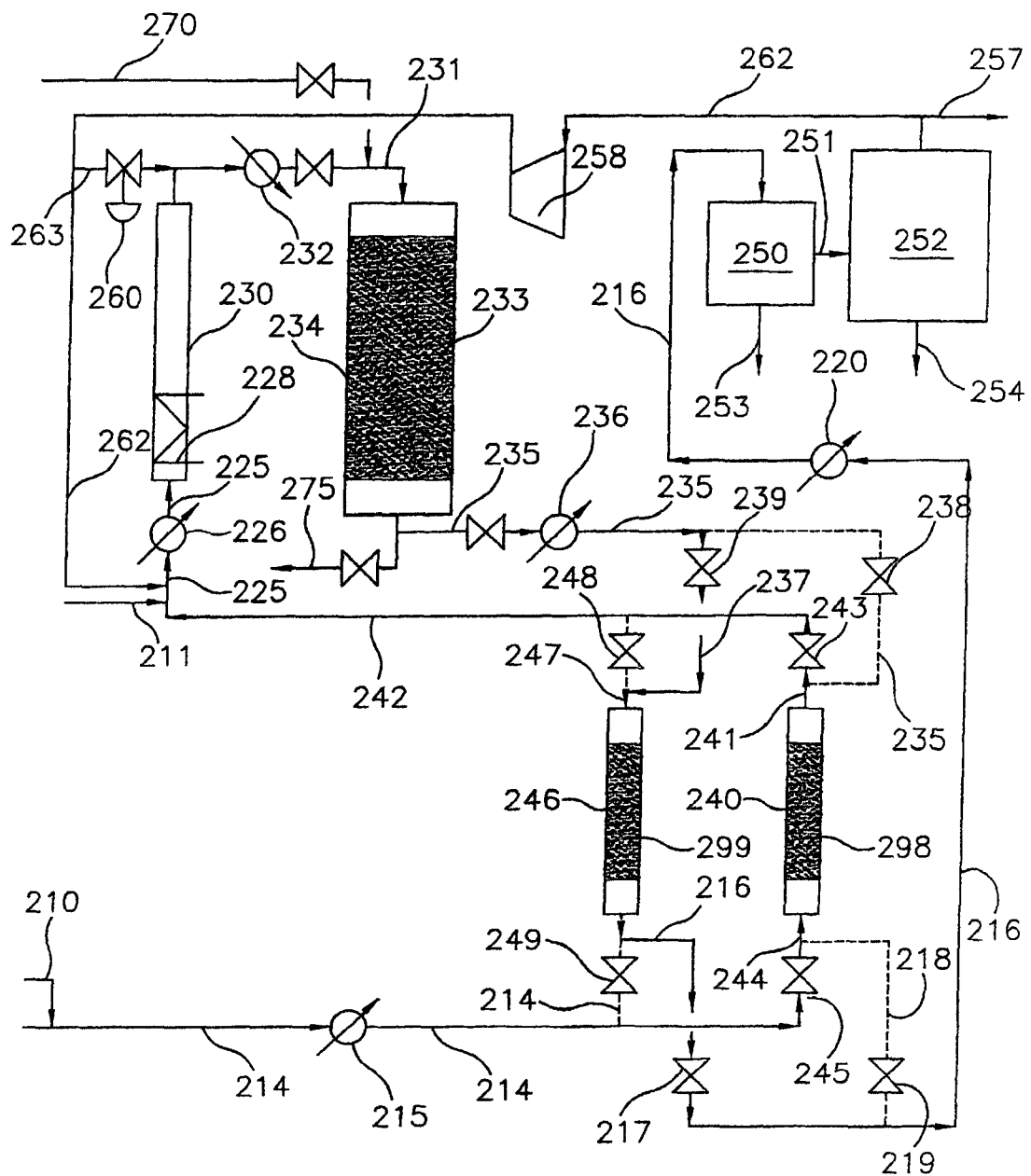
FIG. 5B is a schematic view of the embodiment of the process of the present invention illustrated in FIG. 5A depicting an alternative processing scheme which may be employed when oxygen is used in lieu of air in the oxidation stage.

When oxygen is utilized as the oxidizing gas transported in via line 210 to the reactor being used to oxidize the solid metal bromide contained therein, the embodiment of the process of the present invention illustrated in FIGS. 4A and 5A can be modified such that the bromine vapor produced from either reactor 246 (FIG. 4B) or 240 (FIG. 5B) is transported via lines 242 and 225 directly to first reactor 230. Since oxygen is reactive and will not build up in the system, the need to condense the bromine vapor to a liquid to remove unreactive components, such as nitrogen, is obviated. Compressor 213 is not illustrated in FIGS. 4B and 5B as substantially all commercial sources of oxygen, such as a commercial air separator unit, will provide oxygen to line 210 at the required pressure. If not, a compressor 213 could be utilized to achieve such pressure as will be evident to a skilled artisan.

Figure 6A:
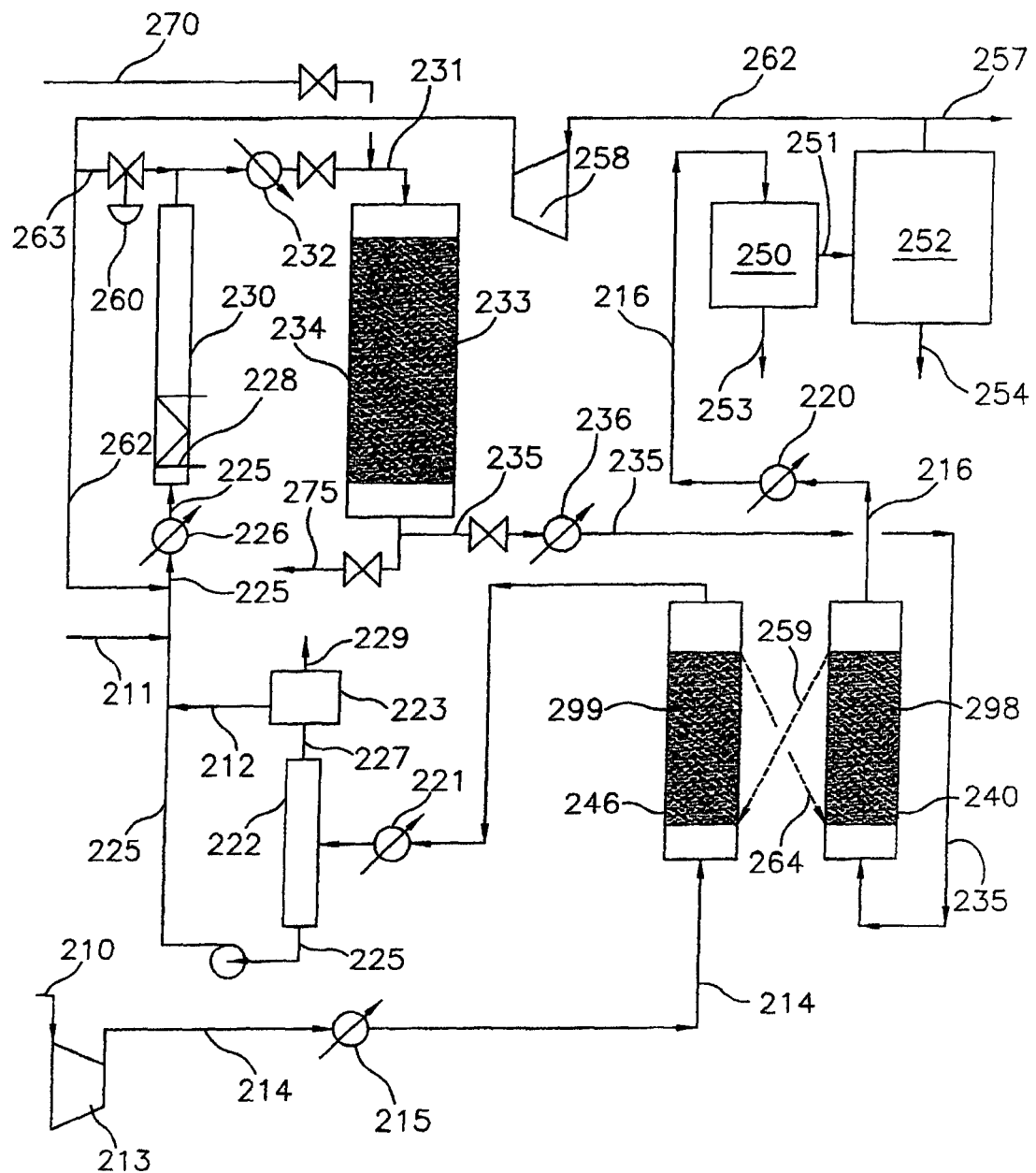
FIG. 6A is a schematic view of another embodiment of the process of the present invention.

In the embodiment of the present invention illustrated in FIG. 6A, the beds of solid metal oxide particles and solid metal bromide particles contained in reactors 240 and 246, respectively, are fluidized and are connected in the manner described below to provide for continuous operation of the beds without the need to provide for equipment, such as valves, to change flow direction to and from each reactor. In accordance with this embodiment, the effluent which comprises olefins, the higher molecular weight hydrocarbons and/ or hydrobromic acid is withdrawn from the second reactor 234 via line 235, cooled to a temperature in the range of about 100° C. to about 500° C. in exchanger 236, and introduced into the bottom of reactor 240 which contains a bed 298 of solid metal oxide particles. The flow of this introduced fluid should induce the particles in bed 298 to move upwardly within reactor 240 as the hydrobromic acid is reacted with the metal oxide in the manner as described above with respect to FIG. 4A. At or near the top of the bed 298, the particles which contain substantially solid metal bromide on the attrition-resistant support due to the substantially complete reaction of the solid metal oxide with hydrobromic acid in reactor 240 are withdrawn via a weir or cyclone or other conventional means of solid/gas separation, flow by gravity down line 259 and are introduced at or near the bottom of the bed 299 of solid metal bromide particles in reactor 246. In the embodiment illustrated in FIG. 6A, oxygen, oxygen enriched air or air 210 is delivered via blower or compressor 213 at a pressure in the range of about ambient to about 10 bar, transported via line 214 through heat exchanger 215, wherein the oxygen, oxygen enriched air or air is preheated to a temperature in the range of about 100° C. to about 500° C. and introduced into second vessel or reactor 246 below bed 299 of a solid phase metal bromide. Oxygen reacts with the metal bromide in the manner described above with respect to FIG. 4A to produce a dry, substantially HBr free bromine vapor. The flow of this introduced gas should induce the particles in bed 299 to flow upwardly within reactor 246 as oxygen is reacted with the metal bromide. At or near the top of the bed 298, the particles which contain substantially solid metal oxide on the attrition-resistant support due to the substantially complete reaction of the solid metal bromide with oxygen in reactor 246 are withdrawn via a weir or cyclone or other conventional means of solid/gas separation, flow by gravity down line 264 and are introduced at or near the bottom of the bed 298 of solid metal oxide particles in reactor 240. In this manner, reactors 240 and 246 may be operated continuously without changing the parameters of operation.

Figure 6B:
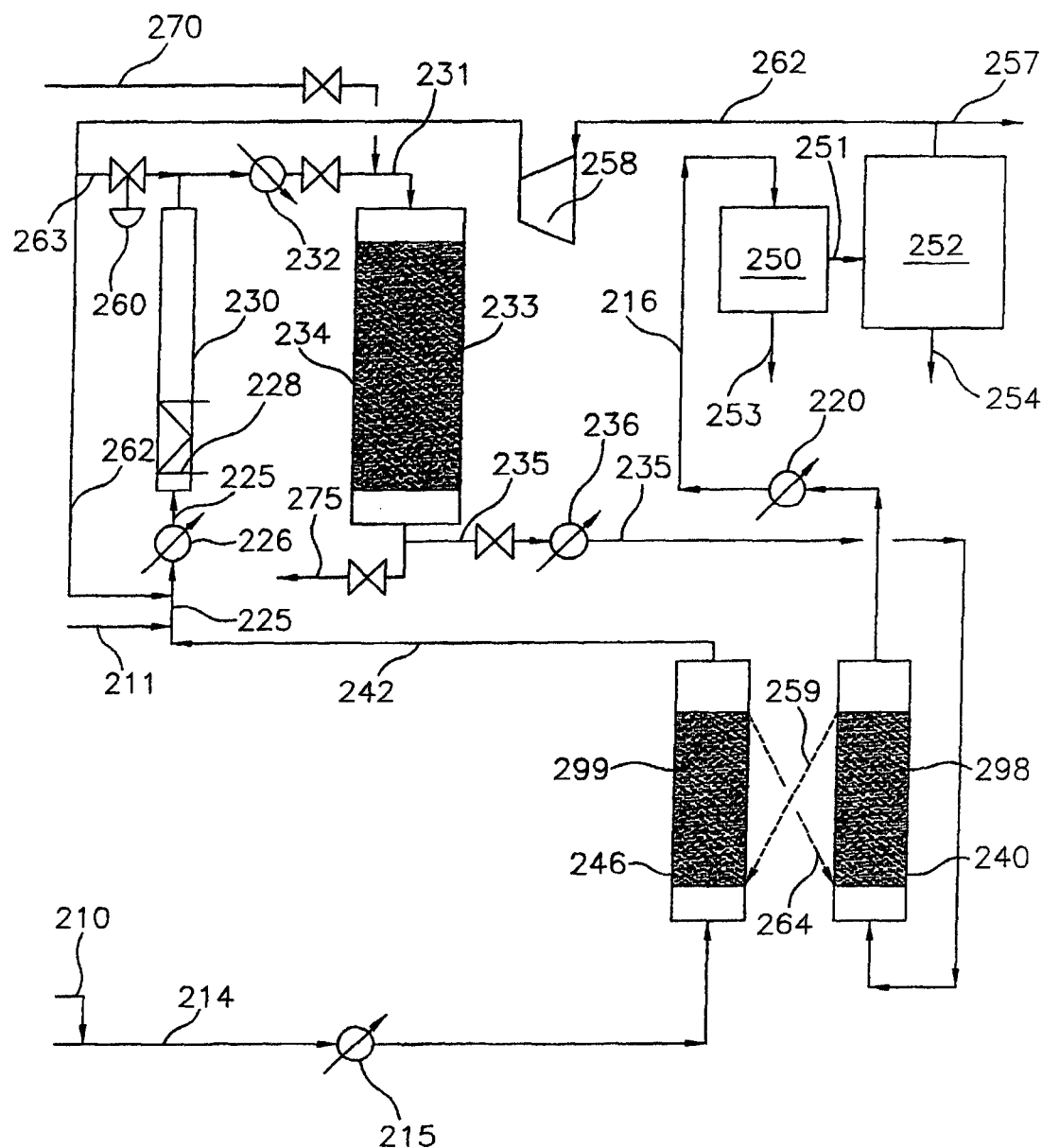
FIG. 6B is a schematic view of the embodiment of the process of the present invention illustrated in FIG. 6A depicting an alternative processing scheme which may be employed when oxygen is used in lieu of air in the oxidation stage.

In the embodiment illustrated in FIG. 6B, oxygen is utilized as the oxidizing gas and is transported in via line 210 to reactor 246. Accordingly, the embodiment of the process of the present invention illustrated in FIG. 6A is modified such that the bromine vapor produced from reactor 246 is transported via lines 242 and 225 directly to first reactor 230. Since oxygen is reactive and will not build up in the system, it is believed that the need to condense the bromine vapor to a liquid to remove unreactive components, such as nitrogen, should be obviated. Compressor 213 is not illustrated in FIG. 6B as substantially all commercial sources of oxygen, such as a commercial air separator unit, will provide oxygen to line 210 at the required pressure. If not, a compressor 213 could be utilized to achieve such pressure as will be evident to a skilled artisan.

Figure 7:
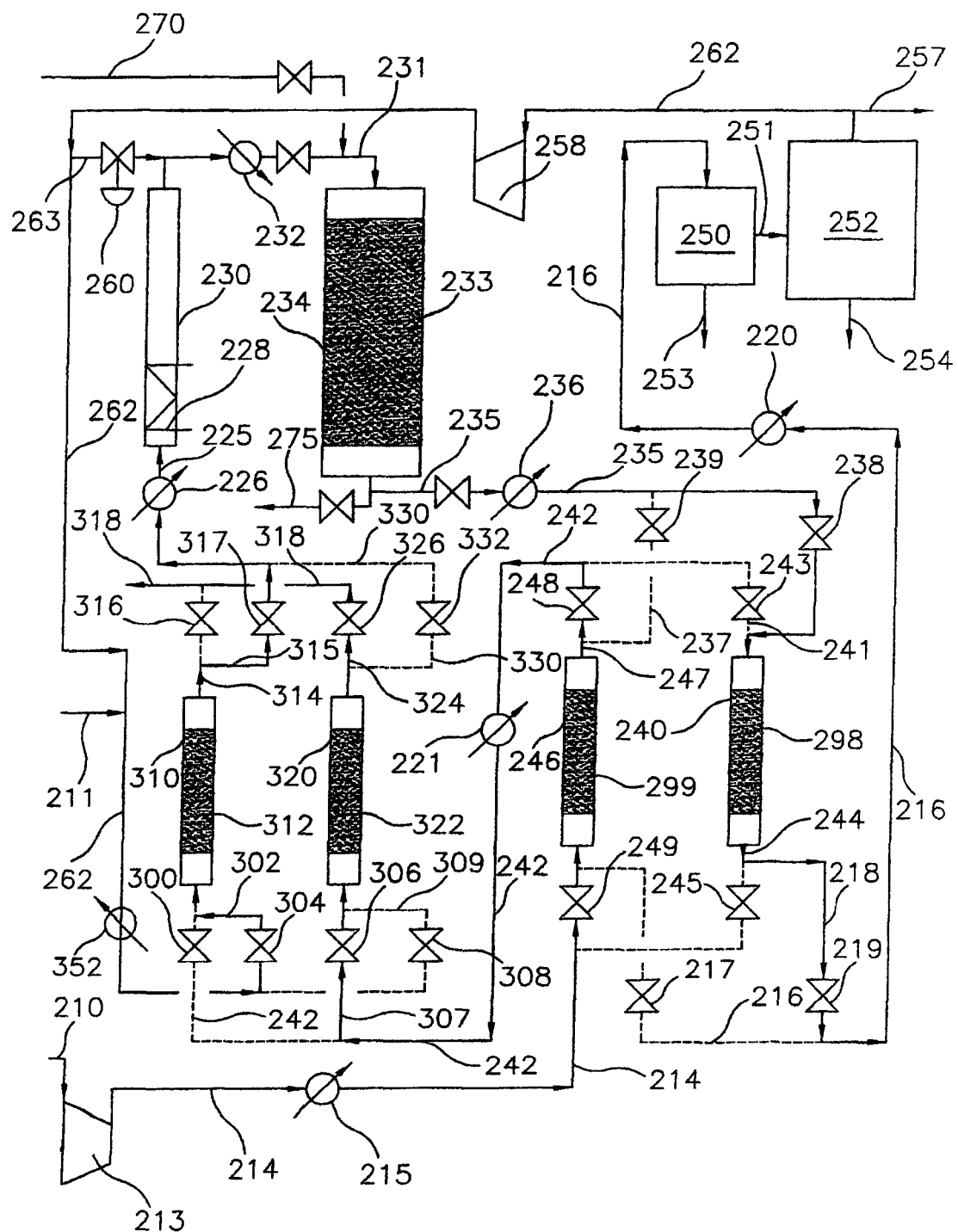
FIG. 7 is a schematic view of another embodiment of the process of the present invention.

In accordance with another embodiment of the process of the present invention that is illustrated in FIG. 7, the alkyl bromination and alkyl bromide conversion stages are operated in a substantially similar manner to those corresponding stages described in detail with respect to FIG. 4A except as discussed below. Residual air or oxygen and bromine vapor emanating from reactor 246 is transported via line 247, valve 248 and line 242 and valve 300 to heat exchanger or condenser 221 wherein the bromine-containing gas is cooled to a temperature in the range of about 30° C. to about 300° C. The bromine-containing vapor is then transported via line 242 to vessel or reactor 320 containing a bed 322 of a solid phase metal bromide in a reduced valence state. The metal of the metal bromide in a reduced valence state is selected from copper (Cu), iron (Fe), or molybdenum (Mo). The metal is selected for the impact of its physical and thermodynamic properties relative to the desired temperature of operation, and also for potential environmental and health impacts and cost. Preferably, copper or iron are employed as the metal, with copper being the most preferred. The solid metal bromide is preferably immobilized on a suitable attrition-resistant support, for example a synthetic amorphous silica, such as Davicat Grade 57, manufactured by Davison Catalysts of Columbia, Md. More preferably the metal is deposited in oxide form in a range of about 10 to 20 wt % on an alumina support with a specific surface area in the range of about 50 to 200 m2/g, In reactor 320, bromine vapor is reacted with the solid phase metal bromide, preferably retained on a suitable attrition-resistant support at temperatures below about 300° C. and preferably between about 30° C. to about 200° C. in accordance with the following general formula wherein $M^2$ represents the metal:

$$2M^2Br_n + Br_2 \rightarrow 2M^2Br_{n+1}$$

In this manner, bromine is stored as a second metal bromide, i.e. $2M^2Br_{n+1}$, in reactor 320 while the resultant vapor containing residual air or oxygen is vented from reactor 320 via line 324, valve 326 and line 318.

The gas stream containing lower molecular weight alkanes, comprised of mixture of a feed gas (line 211) and a recycled gas stream, is transported or conveyed via line 262, heat exchanger 352, wherein the gas stream is preheated to a temperature in the range of about 150° C. to about 600° C., valve 304 and line 302 to a second vessel or reactor 310 containing a bed 312 of a solid phase metal bromide in an oxidized valence state. The metal of the metal bromide in an oxidized valence state is selected from copper (Cu), iron (Fe), or molybdenum (Mo). The metal is selected for the impact of its physical and thermodynamic properties relative to the desired temperature of operation, and also for potential environmental and health impacts and cost. Preferably, copper or iron are employed as the metal, with copper being the most preferred. The solid metal bromide in an oxidized state is preferably immobilized on a suitable attrition-resistant support, for example a synthetic amorphous silica such as Davicat Grade 57, manufactured by Davison Catalysts of Columbia, Md. More preferably the metal is deposited in an oxide state in a range of 10 to 20 wt % supported on an alumina support with a specific surface area of about 50 to 200 m2/g. The temperature of the gas stream is from about 150° C. to about 600° C., and preferably from about 200° C. to about 450° C. In second reactor 310, the temperature of the gas stream thermally decomposes the solid phase metal bromide in an oxidized valence state to yield elemental bromine vapor and a solid metal bromide in a reduced state in accordance with the following general formula wherein $M^2$ represents the metal:

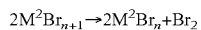

$$2M^2Br_{n+1} \rightarrow 2M^2Br_n + Br_2$$

The resultant bromine vapor is transported with the gas stream containing lower molecular weight alkanes via lines 314, 315, valve 317, line 330, heat exchanger 226 prior to being introduced into alkyl bromination reactor 230.

Figure 8:
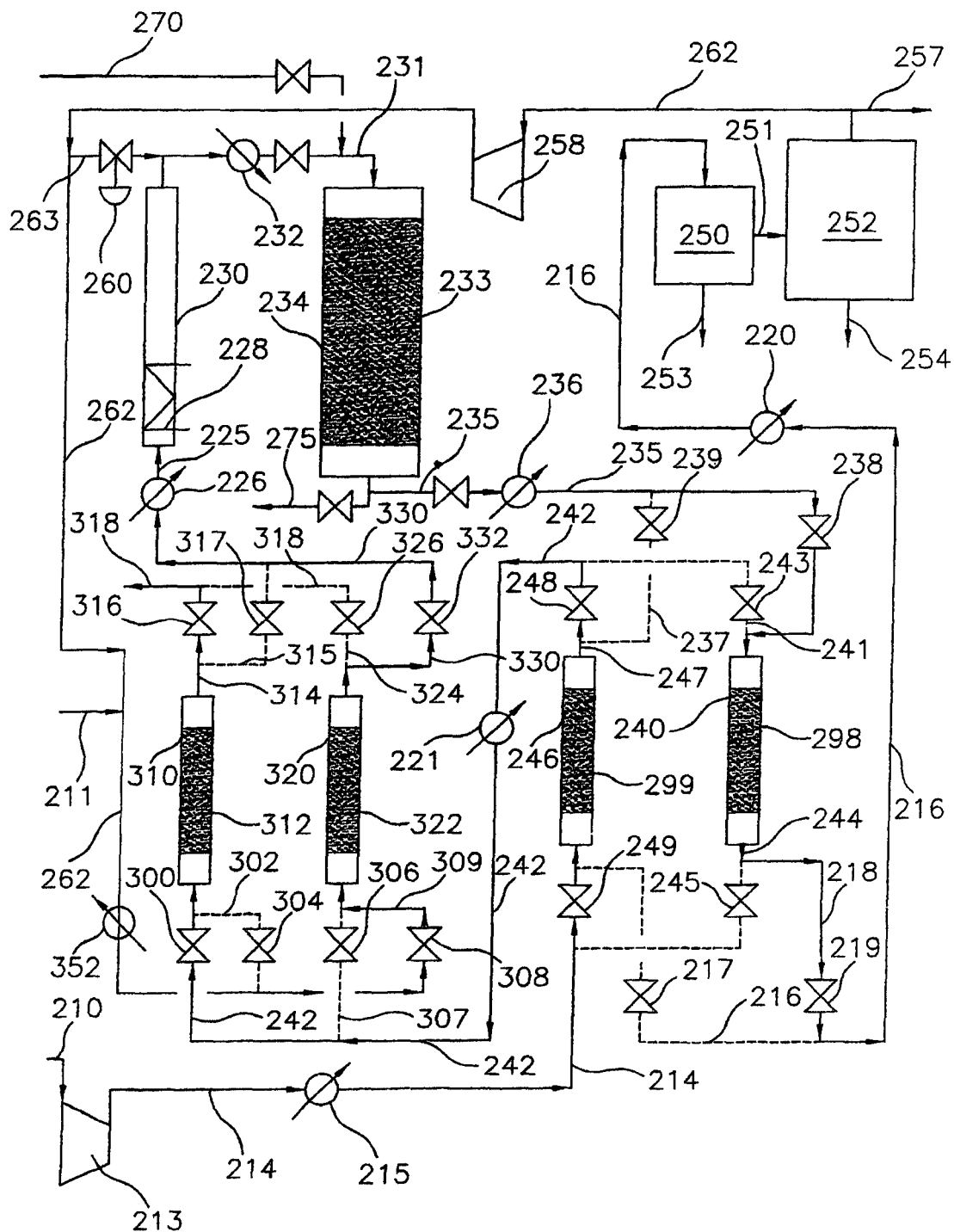
FIG. 8 is a schematic view of the embodiment of the process of the present invention illustrated in FIG. 7 with the flow through the metal oxide beds being reversed.

Reactors 310 and 320 may be operated in a cyclic fashion. As illustrated in FIG. 7, valve 304 is operated in the open mode to permit the gas stream containing lower molecular weight alkanes to be transported to the second reactor 310, while valve 317 is operated in the open mode to permit this gas stream with bromine vapor that is generated in reactor 310 to be transported to alkyl bromination reactor 230. Likewise, valve 306 is operated in the open mode to permit bromine vapor from reactor 246 to be transported to reactor 320, while valve 326 is operated in the open mode to permit residual air or oxygen to be vented from reactor 320. Once significant conversion of the reduced metal bromide and oxidized metal bromide in reactors 320 and 310, respectively, to the corresponding oxidized and reduced states has occurred, these valves are closed as illustrated in FIG. 8. At this point, bed 322 in reactor 320 is a bed of substantially metal bromide in an oxidized state, while bed 312 in reactor 310 is substantially metal bromide in a reduced state. As illustrated in FIG. 8, valves 304, 317, 306 and 326 are closed, and then valves 308 and 332 are opened to permit the gas stream containing lower molecular weight alkanes to be transported or conveyed via lines 262, heat exchanger 352, wherein gas stream is heated to a range of about 150° C. to about 600° C., valve 308 and line, 309 to reactor 320 to thermally decompose the solid phase metal bromide in an oxidized valence state to yield elemental bromine vapor and a solid metal bromide in a reduced state. Valve 332 is also opened to permit the resultant bromine vapor to be transported with the gas stream containing lower molecular weight alkanes via lines 324 and 330 and heat exchanger 226 prior to being introduced into alkyl bromination reactor 230. In addition, valve 300 is opened to permit. bromine vapor emanating from reactor 246 to be transported via line 242 through exchanger 221 into reactor 310 wherein the solid phase metal bromide in a reduced valence state reacts with bromine to effectively store bromine as a metal bromide. In addition, valve 316 is opened to permit the resulting gas, which is substantially devoid of bromine to be vented via lines 314 and 318. The reactors are operated in this manner until significant conversion of the beds of reduced metal bromide and oxidized metal bromide in reactors 310 and 320, respectively, to the corresponding oxidized and reduced states has occurred and then the reactors are cycled back to the flow schematic illustrated in FIG. 7 by opening and closing valves as previously discussed.

Figure 9:
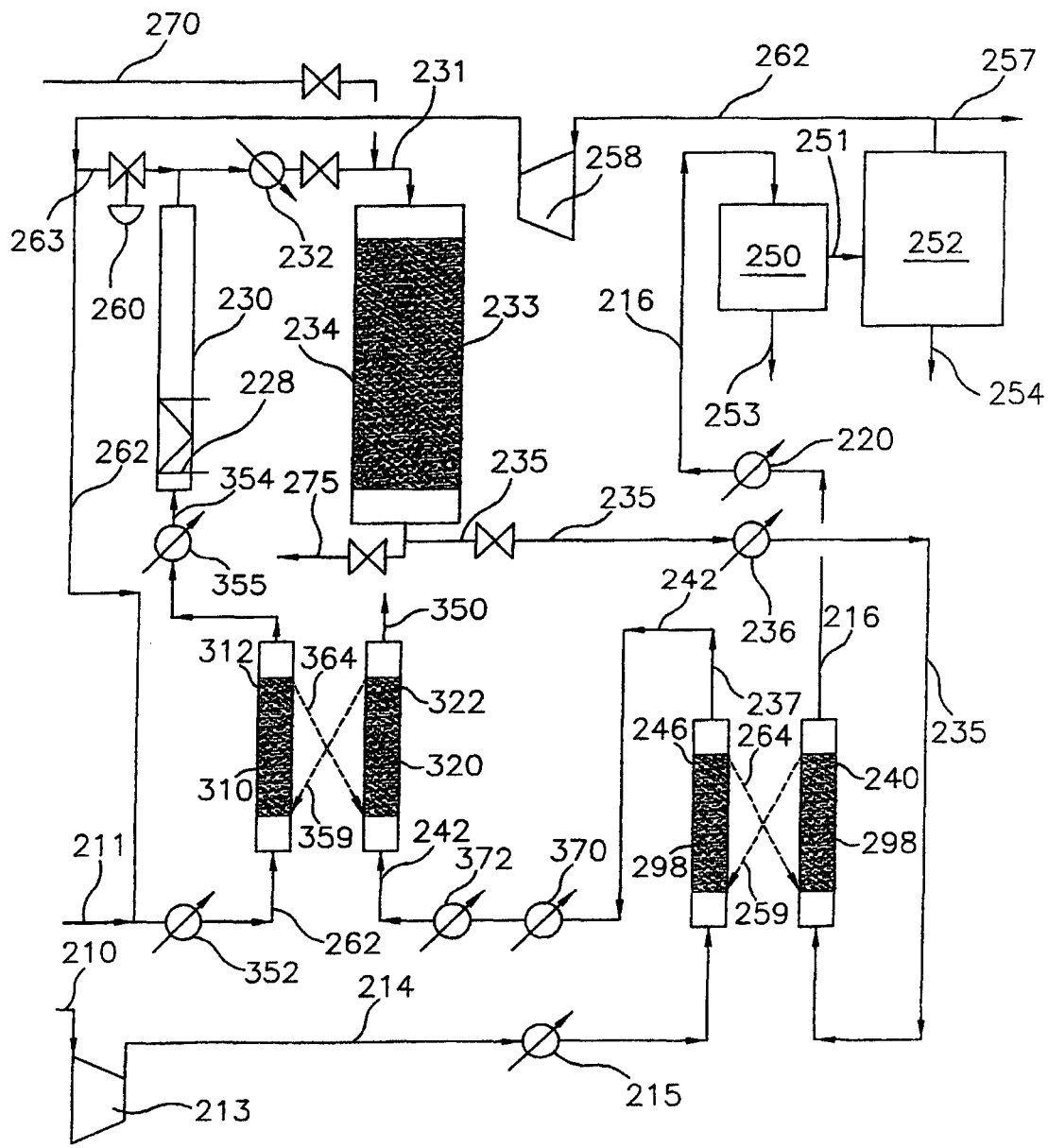
FIG. 9 is a schematic view of another embodiment of the process of the present invention.

In the embodiment of the present invention illustrated in FIG. 9, the beds 312 and 322 contained in reactors 310 and 320, respectively, are fluidized and are connected in the manner described below to provide for continuous operation of the beds without the need to provide for equipment, such as valves, to change flow direction to and from each reactor. In accordance with this embodiment, the bromine-containing gas withdrawn from the reactor 246 via line 242 is cooled to a temperature in the range of about 30° C. to about 300° C. in exchangers 370 and 372, and introduced into the bottom of reactor 320 which contains a moving solid bed 322 in a fluidized state. The flow of this introduced fluid should induce the particles in bed 322 to flow upwardly within reactor 320 as the bromine vapor is reacted with the reduced metal bromide entering the bottom of bed 322 in the manner as described above with respect to FIG. 7. At or near the top of the bed 322, the particles which contain substantially oxidized metal bromide on the attrition-resistant support due to the substantially complete reaction of the reduced metal bromide with bromine vapor in reactor 320 are withdrawn via a weir, cyclone or other conventional means of solid/gas separation, flow by gravity down line 359 and are introduced at or near the bottom of the bed 312 in reactor 310. In the embodiment illustrated in FIG. 9, the gas stream containing lower molecular weight alkanes, comprised of mixture of a feed gas (line 211) and a recycled gas stream, is transported or conveyed via line 262 and heat exchanger 352 wherein the gas stream is heated to a range of about 150° C. to about 600° C. and introduced into reactor 310. The heated gas stream thermally decomposes the solid phase metal bromide in an oxidized valence state present entering at or near the bottom of bed 312 to yield elemental bromine vapor and a solid metal bromide in a reduced state. The flow of this introduced gas should induce the particles in bed 312 to flow upwardly within reactor 310 as the oxidized metal bromide is thermally decomposed. At or near the top of the bed 312, the particles which contain substantially reduced solid metal bromide on the attrition-resistant support due to the substantially complete thermal decomposition in reactor 310 are withdrawn via a weir or cyclone or other conventional means of gas/solid separation and flow by gravity down line 364 and introduced at or near the bottom of the bed 322 of particles in reactor 310. In this manner, reactors 310 and 320 may be operated continuously with changing the parameters of operation.

It is believed that the process of the present invention should be less expensive than conventional process since it operates at low pressures in the range of about 1 bar to about 30 bar and at relatively low temperatures in the range of about 20° C. to about 600° C. for the gas phase, and preferably about 20° C. to about 180° C. for the liquid phase. It is believed that these operating conditions should permit the use of less expensive equipment of relatively simple design that are constructed from readily available metal alloys or glass-lined equipment for the gas phase and polymer-lined or glass-lined vessels, piping and pumps for the liquid phase. It is believed that the process of the present invention also should be more efficient because less energy should be required for operation and the production of excessive carbon dioxide as an unwanted byproduct is minimized. The process is capable of directly producing a mixed hydrocarbon product containing various molecular-weight components in the liquefied petroleum gas (LPG), olefin and motor gasoline fuels range that have substantial aromatic content thereby significantly increasing the octane value of the gasoline-range fuel components.

The following examples demonstrate the practice and utility of the present invention, but are not to be construed as limiting the scope thereof.

EXAMPLE 1

Various mixtures of dry bromine and methane are reacted homogeneously at temperatures in the range of 459° C. to 491° C. at a Gas Hourly Space Velocity (GHSV which is defined as the gas flow rate in standard liters per hour divided by the gross reactor catalyst-bed volume, including catalyst-bed porosity, in liters) of approximately 7200 $hr^{-1}$. The results of this example indicate that for molar ratios of methane to bromine greater than 4.5:1 selectivity to methyl bromide is in the range of 90 to 95%, with near-complete conversion of bromine.

EXAMPLE 2

Figure 13:
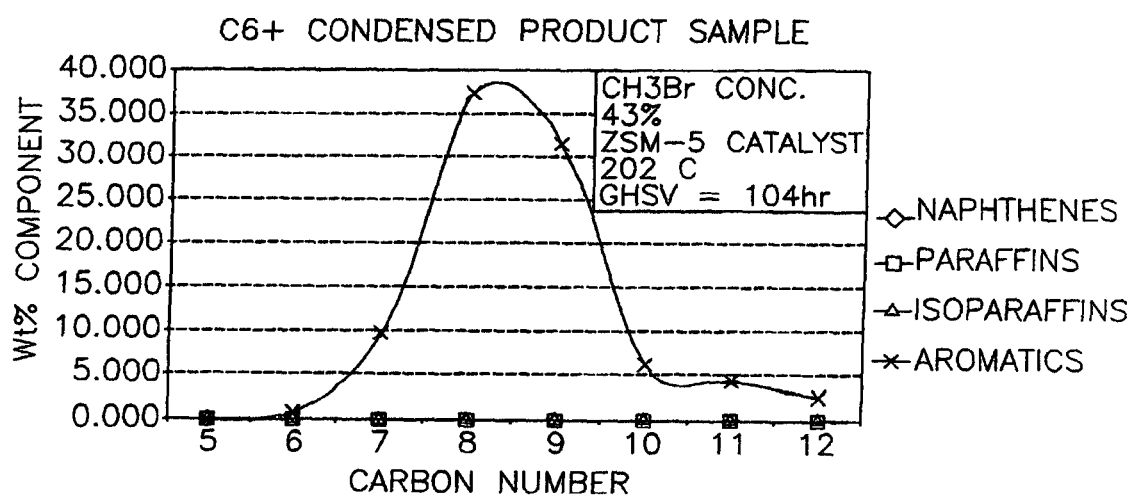
FIG. 13 is a graph of a Paraffinic Olefinic Napthenic and Aromatic (PONA) analysis of a typical condensed product sample of the process of the present invention.
Figure 14:
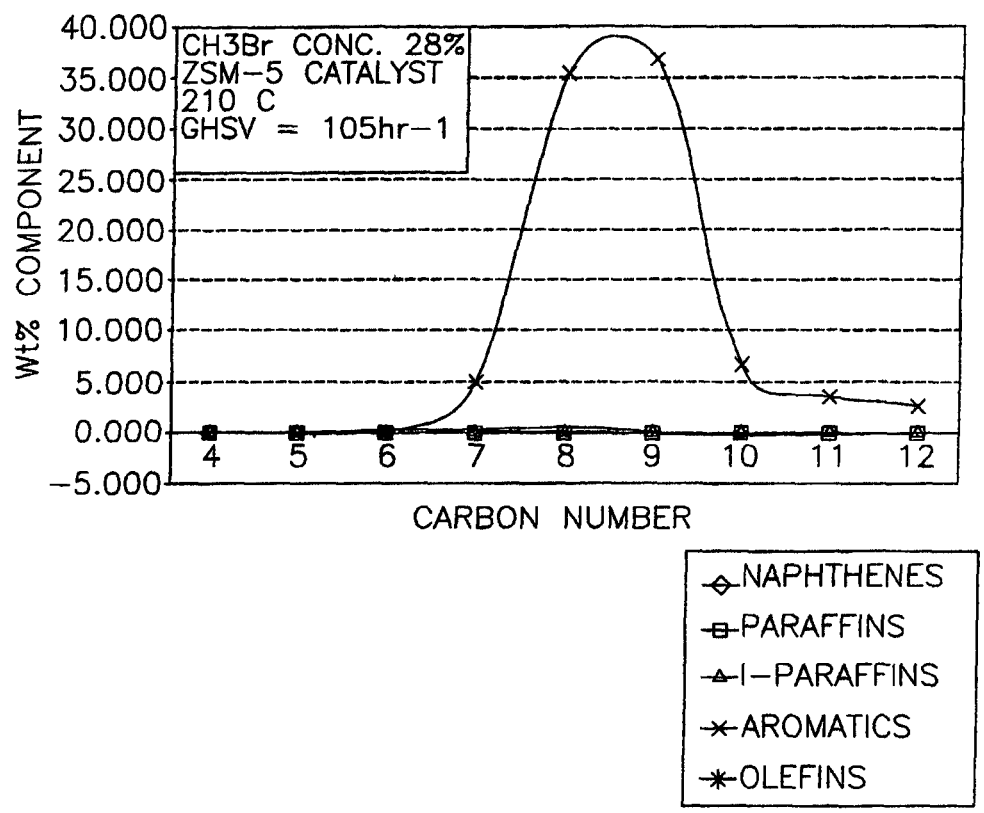
FIG. 14 is a graph of a PONA analysis of another typical condensed product sample of the present invention.

FIG. 13 and FIG. 14 illustrate two exemplary PONA analyses of two $C_6$+ liquid product samples that are recovered during two test runs with methyl bromide and methane reacting over ZSM-5 zeolite catalyst. These analyses show the substantially aromatic content of the $C_6$+ fractions produced.

EXAMPLE 3

Figure 10:
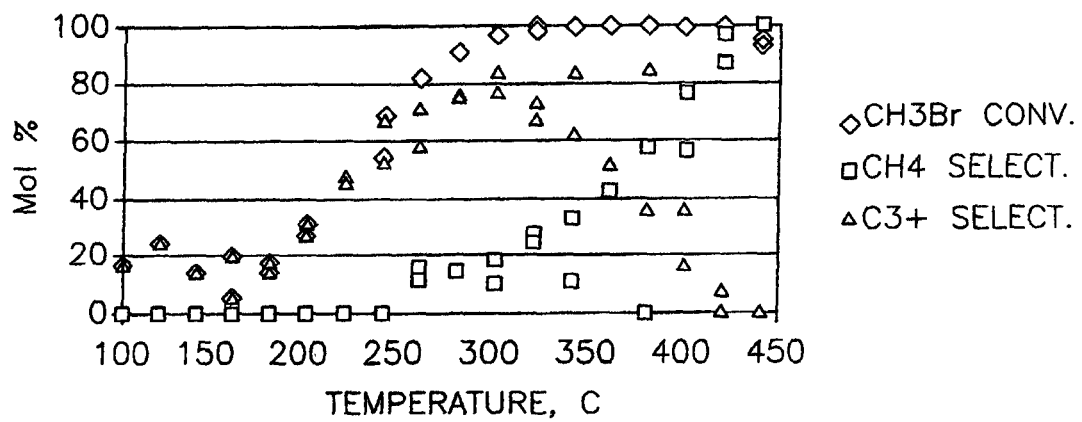
FIG. 10 is a graph of methyl bromide conversion and product selectivity for the oligomerization reaction of the process of the present invention as a function of temperature.

Methyl bromide is reacted over a ZSM-5 zeolite catalyst at a Gas Hourly Space Velocity (GHSV) of approximately 94 $hr^{-1}$ over a range of temperatures from about 100° C. to about 460° C. at approximately 2 bar pressure. As illustrated in FIG. 10, which is a graph of methyl bromide conversion and product selectivity for the oligimerization reaction as a function of temperature, methyl bromide conversion increases rapidly in the range of about 200° C. to about 350° C. Lower temperatures in the range of about 100° C. to about 250° C. favor selectivity towards higher molecular weight products however conversion is low. Higher temperatures in the range of about 250° C. to about 350° C. show higher conversions in the range of 50% to near 100%, however increasing selectivity to lower molecular weight products, in particular undesirable methane is observed. At higher temperatures above 350° C. selectivity to methane rapidly increases. At about 450° C., almost complete conversion to methane occurs.

EXAMPLE 4

Figure 11:
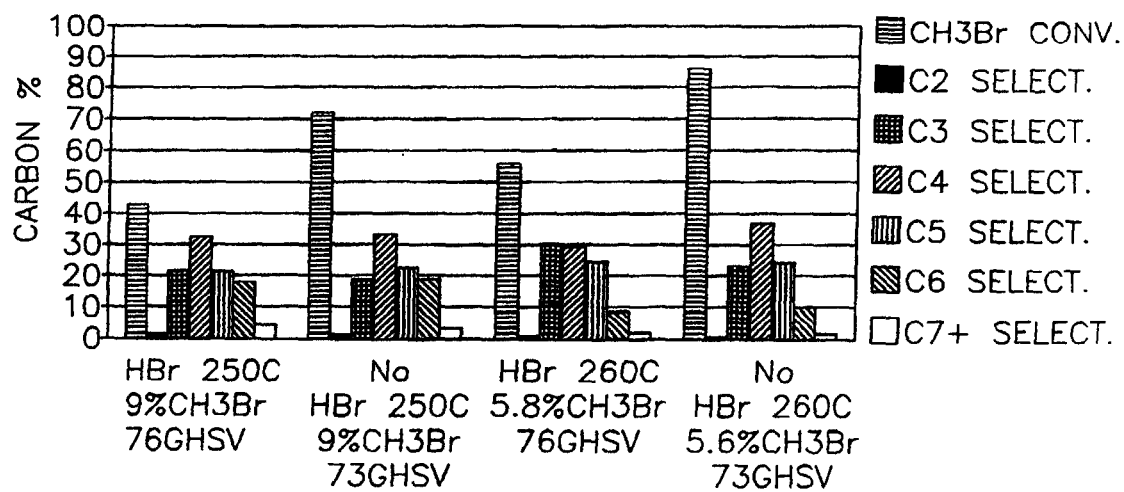
FIG. 11 is a graph comparing conversion and selectivity for the example of methyl bromide, dry hydrobromic acid and methane versus only methyl bromide plus methane.

Methyl bromide, hydrogen bromide and methane are reacted over a ZSM-5 zeolite catalyst at approximately 2 bar pressure at about 250° C. and also at about 260° C. at a GHSV of approximately 76 $hr^{-1}$. Comparison tests utilizing a mixture of only methyl bromide and methane without hydrogen bromide over the same ZSM-5 catalyst at approximately the same pressure at about 250° C. and at about 260° C. at a GHSV of approximately 73 $hr^{-1}$ were also run. FIG. 11, which is a graph that illustrates the comparative conversions and selectivities of several example test runs, shows only a very minor effect due to the presence of HBr on product selectivities. Because hydrobromic acid has only a minor effect on conversion and selectivity, it is not necessary to remove the hydrobromic acid generated in the bromination reaction step prior to the conversion reaction of the alkyl bromides, in which additional hydrobromic acid is formed in any case. Thus, the process can be substantially simplified.

EXAMPLE 5

Figure 12:
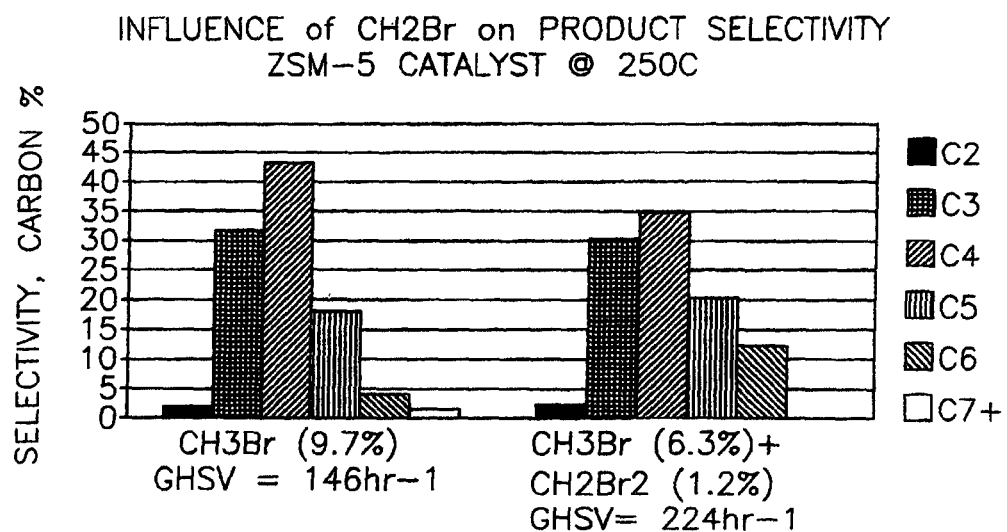
FIG. 12 is a graph of product selectivity from reaction of methyl bromide and dibromomethane vs. product selectivity from reaction of methyl bromide only.

Methyl bromide is reacted over a ZSM-5 zeolite catalyst at 230° C. Dibromomethane is added to the reactor. FIG. 12, which is a graph of product selectivity, indicates that reaction of methyl bromide and dibromomethane results in a shift in selectivity towards $C_5$+ products versus. methyl bromide alone. Thus, these results demonstrate that dibromomethane is also reactive and therefore very high selectivity to bromomethane in the bromination step is not required in the process of the present invention. It has been observed, however, that the presence of dibromomethane increases the rate of catalyst deactivation, requiring a higher operating temperature to optimize the tradeoff between selectivity and deactivation rate, as compared to pure methyl bromide.

EXAMPLE 6

A mixture of 12.1 mol % methyl bromide and 2.8 mol % propyl bromide in methane are reacted over a ZSM-5 zeolite catalyst at 295 C and a GHSV of approximately 260 $hr^{-1}$. A methyl bromide conversion of approximately 86% and a propyl bromide conversion of approximately 98% is observed.

Thus, in accordance with all embodiments of the present invention set forth above, the metal bromide/metal hydroxide, metal oxy-bromide or metal oxide operates in a catalytic cycle allowing bromine to be easily recycled within the process. The metal bromide is readily oxidized by oxygen, oxygen enriched air or air either in the aqueous phase or the vapor phase at temperatures in the range of about 100° C. to about 600° C. and most preferably in the range of about 120° C. to about 180° C. to yield elemental bromine vapor and metal hydroxide, metal oxy-bromide or metal oxide. Operation at temperatures below about 180° C. is advantageous, thereby allowing the use of low-cost corrosion-resistant fluoropolymer-lined equipment. Hydrobromic acid is neutralized by reaction with the metal hydroxide or metal oxide yielding steam and the metal bromide.

While the foregoing preferred embodiments of the invention have been described and shown, it is understood that the alternatives and modifications, such as those suggested and others, may be made thereto and fall within the scope of the invention.

I claim:
1. A process comprising:
    separating hydrobromic acid from a gaseous stream comprising hydrobromic acid and hydrocarbons;
    converting said hydrobromic acid to at least bromine;
    contacting said bromine with gaseous alkanes, in a first reactor, to form bromination products comprising alkyl bromides;
    reacting said alkyl bromides in a second reactor to convert at least a portion of said alkyl bromides to synthesis products comprising hydrocarbon products and additional hydrobromic acid, wherein the hydrocarbon prod- ucts comprise hydrocarbons selected from the group consisting of olefins, C5+ hydrocarbons, and combinations thereof;

withdrawing effluent from the second reactor comprising the hydrocarbon products and additional hydrobromic acid; and converting the additional hydrobromic acid in the effluent withdrawn from the second reactor to at least bromine.

2. The process of claim 1 wherein said step of separating said hydrobromic acid from said hydrocarbons comprises:
contacting said gaseous stream with water.

3. The process of claim 2 wherein said step of contacting said gaseous stream with said water comprises:
neutralizing said hydrobromic acid to form an aqueous solution comprising said water and a metal bromide salt, the metal of said metal bromide salt being selected from Cu, Zn, Fe, Co, Ni, Mn, Ca or Mg bromide.

4. The process of claim 3 wherein said step of converting comprises:
oxidizing said aqueous solution containing said metal bromide salt to form at least said bromine and a reaction product selected from the group consisting of a metal hydroxide, a metal oxy-bromide species and combinations thereof; and
separating said bromine from said reaction product.

5. The process of claim 4 wherein said water that contacts said gaseous stream comprises said reaction product.

6. The process of claim 2 wherein said hydrobromic acid dissolves into said water forming a hydrobromic acid solution, said process further comprising:
vaporizing said hydrobromic acid solution; and
reacting said vaporized hydrobromic acid solution with a metal oxide to form a reaction product comprising a metal bromide salt, the metal of said metal bromide salt being selected from the group of Cu, Zn, Fe, Co, Ni, Mn, Ca or Mg.

7. The process of claim 6 wherein said step of converting comprises:
oxidizing said metal bromide salt to form oxidation products comprising said bromine and said metal oxide; and
separating said bromine from said metal oxide.

8. The process of claim 6 wherein said metal bromide salt is contained on a porous support.

9. The process of claim 1 wherein said step of separating hydrobromic acid from hydrocarbons comprises reacting said hydrobromic acid with a metal oxide to form reaction products comprising a metal bromide and steam.

10. The process of claim 9 wherein the metal of said metal oxide is magnesium, calcium, vanadium, chromium, manganese, iron, cobalt, nickel, copper, zinc or tin.

11. The process of claim 10 wherein said metal oxide is supported on a solid carrier.

12. The process of claim 11 wherein said metal oxide is contained in a bed in a vessel.

13. The process of claim 9 wherein said step of converting comprises:
reacting said metal bromide with an oxygen containing gas to obtain reaction products comprising said metal oxide and said bromine.

14. The process of claim 1 wherein said bromine from the reaction of said metal bromide with said oxygen containing gas is recycled to said step of contacting said gaseous alkanes to form alkyl bromides.

15. The process of claim 1 wherein the step of reacting said alkyl bromides is in the presence a synthetic crystalline alumino-silicate catalyst.

16. A process comprising:
contacting a gaseous stream comprising hydrobromic acid and hydrocarbons with an aqueous solution comprising a base selected from the group consisting of a metal hydroxide, a metal oxy-bromide species, and combinations thereof such that the hydrobromic acid is neutralized to form a metal bromide salt in the aqueous solution;
oxidizing said aqueous solution containing said metal bromide salt to form oxidation products comprising bromine and said base;
separating said bromine from said aqueous solution comprising said base; and
contacting said bromine with gaseous alkanes to form alkyl bromides.

17. The process of claim 16 further comprising:
reacting said alkyl bromides in the presence of said hydrobromic acid and a synthetic crystalline alumino-silicate catalyst to form said hydrocarbons.

18. A process comprising:
contacting a gaseous stream comprising hydrobromic acid and hydrocarbons with water, wherein said hydrobromic acid dissolves in said water to form an aqueous solution comprising said water and said hydrobromic acid;
neutralizing said hydrobromic acid to form a metal bromide salt;
oxidizing said metal bromide salt to form an oxidation product comprising bromine; and
contacting said bromine with gaseous alkanes to form bromination products comprising alkyl bromides.

19. The process of claim 18 further comprising:
reacting said alkyl bromides in the presence of said hydrobromic acid and a synthetic crystalline alumino-silicate catalyst to form reaction products comprising said hydrocarbons.

20. A process comprising:
reacting hydrobromic acid with a metal oxide to form reaction products comprising a metal bromide and steam, wherein said hydrobromic acid is contained in a gaseous stream comprising said hydrobromic acid and hydrocarbons;
reacting said metal bromide with a gas comprising oxygen to form reaction products comprising bromine and said metal oxide;
contacting said bromine with gaseous alkanes, in a first reactor, to form bromination products comprising alkyl bromides,
reacting said alkyl bromides in a second reactor to convert at least a portion of said alkyl bromides to synthesis products comprising hydrocarbon products and additional hydrobromic acid, wherein the hydrocarbon products comprise hydrocarbons selected from the group consisting of olefins, C5+ hydrocarbons, and combinations thereof;
withdrawing effluent from the second reactor comprising the hydrocarbon products and additional hydrobromic acid; and
reacting the additional hydrobromic acid in the effluent withdrawn from the second reactor with a metal oxide.

21. The process of claim 19 wherein the step of reacting said alkyl bromides is in the presence of a synthetic crystalline alumino-silicate catalyst.

* * * * *